United States Patent
Quay

(10) Patent No.: US 6,887,210 B2
(45) Date of Patent: *May 3, 2005

(54) DEVICES AND METHODS FOR OBTAINING MAMMARY FLUID SAMPLES FOR EVALUATING BREAST DISEASES, INCLUDING CANCER

(75) Inventor: Steven C. Quay, Edmonds, WA (US)

(73) Assignee: Atossa Healthcare, Inc., Edmonds, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/002,540

(22) Filed: Nov. 13, 2001

(65) Prior Publication Data

US 2002/0072702 A1 Jun. 13, 2002

Related U.S. Application Data

(60) Provisional application No. 60/248,134, filed on Nov. 13, 2000, and provisional application No. 60/248,136, filed on Nov. 13, 2000.

(51) Int. Cl.$^7$ .............................. A61B 5/00; B65D 81/00
(52) U.S. Cl. .......................... 600/573; 604/74; 422/102
(58) Field of Search ...................... 600/573; 604/73–76, 604/319, 320, 346; 422/100, 101, 104; 435/6, 7, 7.1, 7.2, 7.21, 7.23, 24, 29, 30, 296, 810, 975; 436/64, 161, 162, 177, 178, 807–810, 813, 510, 574, 576, 523–531

(56) References Cited

U.S. PATENT DOCUMENTS

| | | | | |
|---|---|---|---|---|
| 3,786,801 A | * | 1/1974 | Sartorius | 600/573 |
| 4,929,229 A | * | 5/1990 | Larsson | 604/74 |
| 5,295,957 A | * | 3/1994 | Aida et al. | 604/74 |
| 6,287,521 B1 | * | 9/2001 | Quay et al. | 422/101 |
| 6,471,660 B1 | * | 10/2002 | Covington | 600/584 |
| 6,517,513 B1 | * | 2/2003 | Covington et al. | 604/74 |

* cited by examiner

*Primary Examiner*—Charles Marmor
(74) *Attorney, Agent, or Firm*—Graybeal Jackson Haley

(57) ABSTRACT

Biological samples of mammary fluid or components thereof are obtained using a breast pump device coupled with a solid phase sample collection medium, alternatively facilitated by administering oxytocin to the subject. The breast pump device stimulates expression of mammary fluid and provides for collection of diagnostic samples to evaluate breast disease, including cancer. The biological sample may include whole cells or cellular components, purified or bulk proteins, glycoproteins, peptides, nucleotides or other desired constituents comprising a breast disease marker. Methods, kits and adapter devices relating to the breast pump device are also provided. Yet additional methods, devices, accessories, and materials are provided for laboratory handling and processing of breast fluid samples and for related diagnostic methods.

36 Claims, 9 Drawing Sheets

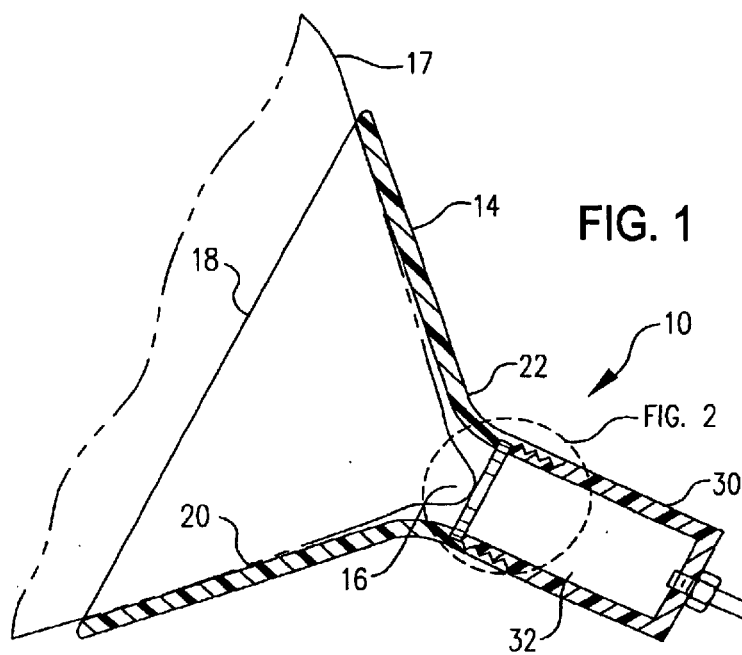
FIG. 1
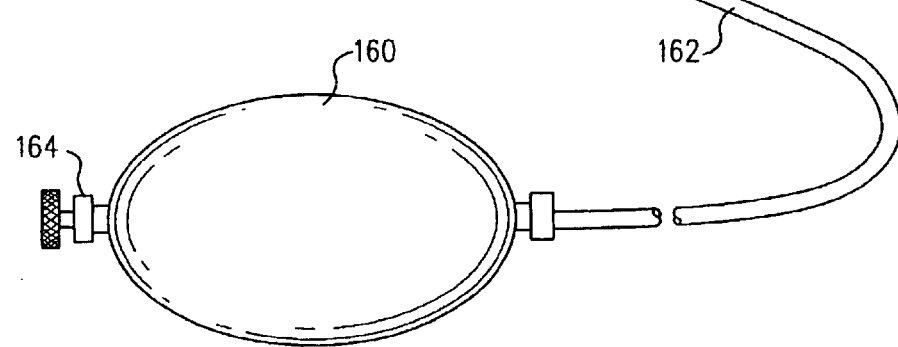
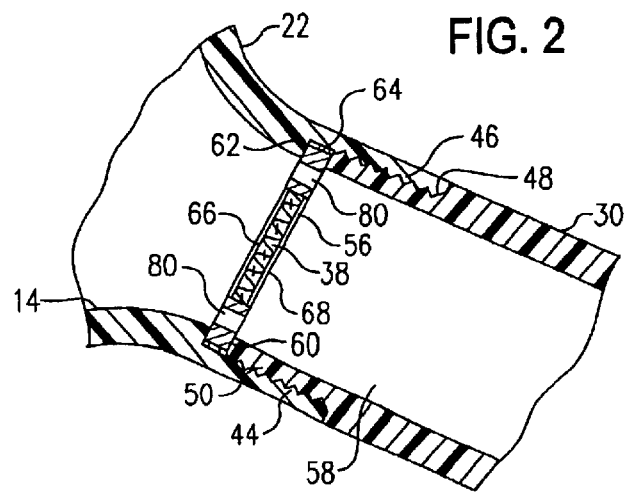
FIG. 2

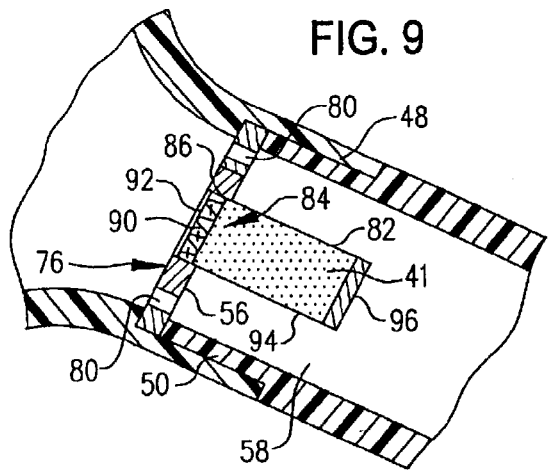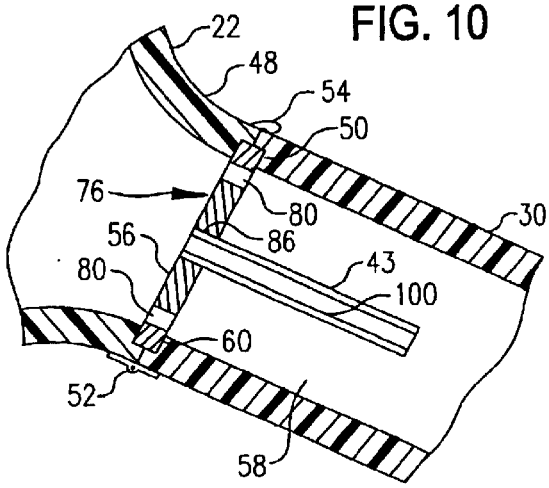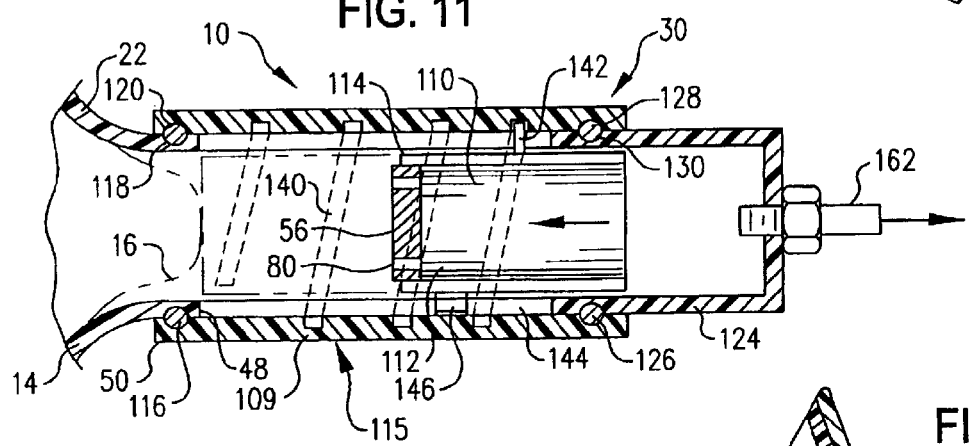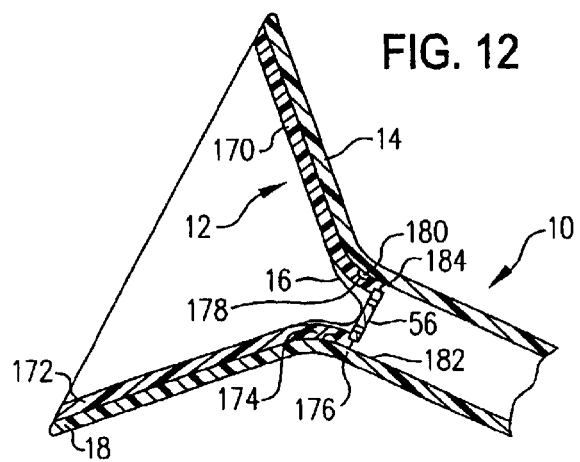

DEVICES AND METHODS FOR OBTAINING MAMMARY FLUID SAMPLES FOR EVALUATING BREAST DISEASES, INCLUDING CANCER

RELATED APPLICATIONS

This application claims the priority benefits of U.S. Provisional Patent Application No. 60/248,134, filed by Quay on Nov. 13, 2000 and U.S. Provisional Patent Application No. 60/248,136, filed by Quay on Nov. 13, 2000. The disclosures of each of the foregoing priority applications are incorporated herein by reference in their entirety.

TECHNICAL FIELD OF INVENTION

The invention relates to methods, devices, and kits for obtaining and assaying biological samples from mammary fluid. More specifically, the invention relates to methods, devices, and kits for obtaining and assaying fluid and cytological samples from the mammary glands of a mammalian subject for evaluating, diagnosing and managing breast disease, including infections, pre-cancerous conditions, cancer susceptibility and cancer.

BACKGROUND OF THE INVENTION

Breast cancer is by far the most common form of cancer in women, and is the second leading cause of cancer death in humans. Despite many recent advances in diagnosing and treating breast cancer, the prevalence of this disease has been steadily rising at a rate of about 1% per year since 1940. Today, the likelihood that a women living in North America will develop breast cancer during her lifetime is one in eight.

The current widespread use of mammography has resulted in improved detection of breast cancer. Nonetheless, the death rate due to breast cancer has remained unchanged at about 27 deaths per 100,000 women. All too often, breast cancer is discovered at a stage that is too far advanced, when therapeutic options and survival rates are severely limited. Accordingly, more sensitive and reliable methods are needed to detect small (less than 2 cm diameter), early stage, in situ carcinomas of the breast. Such methods should significantly improve breast cancer survival, as suggested by the successful employment of Papinicolou smears for early detection and treatment of cervical cancer.

In addition to the problem of early detection, there remain serious problems in distinguishing between malignant and benign breast disease, in staging known breast cancers, and in differentiating between different types of breast cancers (e.g. estrogen dependent versus non-estrogen dependent tumors). Recent efforts to develop improved methods for breast cancer detection, staging and classification have focused on a promising array of so-called cancer "markers." Cancer markers are typically proteins that are uniquely expressed (e.g. as a cell surface or secreted protein) by cancerous cells, or are expressed at measurably increased or decreased levels by cancerous cells compared to normal cells. Other cancer markers can include specific DNA or RNA sequences marking deleterious genetic changes or alterations in the patterns or levels of gene expression associated with particular forms of cancer.

A large number and variety of breast cancer markers have been identified to date, and many of these have been shown to have important value for determining prognostic and/or treatment-related variables. Prognostic variables are those variables that serve to predict disease outcome, such as the likelihood or timing of relapse or survival. Treatment-related variables predict the likelihood of success or failure of a given therapeutic plan. Certain breast cancer markers clearly serve both functions. For example, estrogen receptor levels are predictive of relapse and survival for breast cancer patients, independent of treatment, and are also predictive of responsiveness to endocrine therapy. Pertschuk et al., *Cancer* 66:1663–1670, 1990; Parl and Posey, *Hum. Pathol.* 19:960–966, 1988; Kinsel et al., *Cancer Res.* 49:1052–1056, 1989; Anderson and Poulson *Cancer* 65:1901–1908, 1989.

The utility of specific breast cancer markers for screening and diagnosis, staging and classification, monitoring and/or therapy purposes depends on the nature and activity of the marker in question. For general reviews of breast cancer markers, see Porter-Jordan et al., *Hematol. Oncol. Clin. North Amer.* 8:73–100, 1994; and Greiner, *Pharmaceutical Tech.*, May, 1993, pp. 28–44. As reflected in these reviews, a primary focus for developing breast cancer markers has centered on the overlapping areas of tumorigenesis, tumor growth and cancer invasion. Tumorigenesis and tumor growth can be assessed using a variety of cell proliferation markers (for example Ki67, cyclin D1 and proliferating cell nuclear antigen (PCNA)), some of which may be important oncogenes as well. Tumor growth can also be evaluated using a variety of growth factor and hormone markers (for example estrogen, epidermal growth factor (EGF), erbB-2, transforming growth factor (TGF), which may be overexpressed, underexpressed or exhibit altered activity in cancer cells. By the same token, receptors of autocrine or exocrine growth factors and hormones (for example insulin growth factor (IGF) receptors, and EGF receptor) may also exhibit changes in expression or activity associated with tumor growth. Lastly, tumor growth is supported by angiogenesis involving the elaboration and growth of new blood vessels and the concomitant expression of angiogenic factors that can serve as markers for tumorigenesis and tumor growth.

In addition to tumorigenic, proliferation and growth markers, a number of markers have been identified that can serve as indicators of invasiveness and/or metastatic potential in a population of cancer cells. These markers generally reflect altered interactions between cancer cells and their surrounding microenvironment. For example, when cancer cells invade or metastasize, detectable changes may occur in the expression or activity of cell adhesion or motility factors, examples of which include the cancer markers Cathepsin D, plasminogen activators, collagenases and other factors. In addition, decreased expression or overexpression of several putative tumor "suppressor" genes (for example nm23, p53 and rb) has been directly associated with increased metastatic potential or deregulation of growth predictive of poor disease outcome.

Additional representative breast disease markers within these various classes include prostaglandin E2 (PGE2); estrogen-regulated proteins such as pS2; interleukins (e.g., IL-10); S-100 protein; vimentin; epithelial membrane antigen; prostate specific antigen (PSA); bcl-2; CA15-3 (an aberrant form of polymorphic epithelial mucin (PEM)); CA 19-9; mucin core carbohydrates (e.g., Tn antigen and Tn-like antigens); alpha-lactalbumin; lipid-associated sialic acid (LASA); galactose-N-acetylgalactosamine (Gal-GalNAC); GCDFP-15; Le(y)-related carbohydrate antigen; CA 125; urokinase-type plasminogen activator (uPA) and uPA related antigens and complexes (e.g., LMW-uPA, HMW-uPA, uPA aminoterminal fragment (ATF), uPA receptor (uPAR) and complexes with inhibitors such as PAl-1 and PAl-2); beta-glucuronidase; CD31; CD44 splice variants; blood group antigens (e.g., ABH, Lewis, and MN); and genetic lesions or altered expression levels of CCND1, EMS1, BRCA1 and BRCA2 genes.

In summary, the evaluation of proliferation markers, oncogenes, growth factors and growth factor receptors, angiogenic factors, proteases, adhesion factors and tumor suppressor genes, among other cancer markers, can provide important information concerning the risk, presence, status or future behavior of cancer in a patient. Determining the presence or level of expression or activity of one or more of these cancer markers can aid in the differential diagnosis of patients with uncertain clinical abnormalities, for example by distinguishing malignant from benign abnormalities. Furthermore, in patients presenting with established malignancy, cancer markers can be useful to predict the risk of future relapse, or the likelihood of response in a particular patient to a selected therapeutic course. Even more specific information can be obtained by analyzing highly specific cancer markers, or combinations of markers, which may predict responsiveness of a patient to specific drugs or treatment options.

Methods for detecting and measuring cancer markers have been recently revolutionized by the development of immunological assays, particularly by assays that utilize monoclonal antibody technology. Previously, many cancer markers could only be detected or measured using conventional biochemical assay methods, which generally require large test samples and are therefore unsuitable in most clinical applications. In contrast, modern immunoassay techniques can detect and measure cancer markers in relatively much smaller samples, particularly when monoclonal antibodies that specifically recognize a targeted marker protein are used. Accordingly, it is now routine to assay for the presence or absence, level, or activity of selected cancer markers by immunohistochemically staining breast tissue specimens obtained via conventional biopsy methods. Because of the highly sensitive nature of immunohistochemical staining, these methods have also been successfully employed to detect and measure cancer markers in smaller, needle biopsy specimens which require less invasive sample gathering procedures compared to conventional biopsy specimens. In addition, other immunological methods have been developed and are now well known in the art which allow for detection and measurement of cancer markers in non-cellular samples such as serum and other biological fluids from patients. The use of these alternative sample sources substantially reduces the morbidity and costs of assays compared to procedures employing conventional biopsy samples, which allows for application of cancer marker assays in early screening and low risk monitoring programs where invasive biopsy procedures are not indicated.

For the purpose of breast cancer evaluation, the use of conventional or needle biopsy samples for cancer marker assays is often undesirable, because a primary goal of such assays is to detect the cancer before it progresses to a palpable or mammographically detectable tumor stage. Prior to this stage, biopsies are generally contraindicated, making early screening and low risk monitoring procedures employing such samples untenable. Therefore, there is general need in the art to obtain samples for breast cancer marker assays by less invasive means than biopsy, for example by serum withdrawal.

Efforts to utilize serum samples for breast cancer marker assays have met with limited success, largely because the targeted markers are either not detectable in serum, or because telltale changes in the levels or activity of the markers cannot be monitored in serum. In addition, the presence of breast cancer markers in serum probably occurs at the time of micro-metastasis, making serum assays less useful for detecting pre-metastatic disease. In contrast, fluid within the mammary glands themselves is expected to contain much higher and more biologically relevant levels of breast cancer markers than serum, particularly in view of the fact that 80%–90% of all breast cancers occur within the intraductal epithelium of these glands. Fluid within the breast ducts is expected to contain an assemblage and concentration of hormones, growth factors and other potential markers comparable to those secreted by, or acting upon, the surrounding cells of the alveolar-ductal system. Likewise, mammary fluid is expected to contain cells and solid cellular debris or products that can be used in cytological or immunological assays to evaluate intracellular or cell surface markers that may not be detectable in the liquid fraction of mammary fluid.

Previous attempts to develop non-invasive breast cancer marker assays utilizing mammary fluid samples have included studies of mammary fluid obtained from patients presenting with spontaneous nipple discharge. In one of these studies, conducted by Inaji et al., *Cancer* 60:3008–3013, 1987, levels of the breast cancer marker carcinoembryonic antigen (CEA) were measured using conventional, enzyme linked immunoassay (ELISA) and sandwich-type, monoclonal immunoassay methods. These methods successfully and reproducibly demonstrated that CEA levels in spontaneously discharged mammary fluid provide a sensitive indicator of nonpalpable breast cancer. In a subsequent study, also by Inaji et al., *Jpn. J. Clin. Oncol.* 19:373–379, 1989, these results were expanded using a more sensitive, dry chemistry, dot-immunobinding assay for CEA determination. This latter study reported that elevated CEA levels occurred in 43% of patients tested with palpable breast tumors, and in 73% of patients tested with nonpalpable breast tumors. CEA levels in the discharged mammary fluid were highly correlated with intratumoral CEA levels, indicating that the level of CEA expression by breast cancer cells is closely reflected in the mammary fluid CEA content. Based on these results, the authors concluded that immunoassays for CEA in spontaneously discharged mammary fluid are useful for screening nonpalpable breast cancer.

Although the evaluation of mammary fluid has been shown to be a useful method for screening nonpalpable breast cancer in women who experience spontaneous nipple discharge, the rarity of this condition renders the methods of Inaji et al, inapplicable to the majority of women who are candidates for early breast cancer screening. In addition, the first Inaji report cited above determined that certain patients suffering spontaneous nipple discharge secrete less than 10 μl of mammary fluid, which is a critically low level for the ELISA and sandwich immunoassays employed in that study. It is likely that other antibodies used to assay other cancer markers may exhibit even lower sensitivity than the anti-CEA antibodies used by Inaji and coworkers, and may therefore not be adaptable or sensitive enough to be employed even in dry chemical immunoassays of small samples of spontaneously discharged mammary fluid.

In view of the above, an important need exists in the art for more widely applicable, non-invasive methods and materials to obtain biological samples for use in evaluating, diagnosing and managing breast disease including cancer, particularly for screening early stage, nonpalpable breast tumors. A related need exists for methods and materials that utilize such readily obtained biological samples to evaluate, diagnose and manage breast disease, particularly by detecting or measuring selected breast cancer markers, or panels of breast cancer markers, to provide highly specific, cancer prognostic and/or treatment-related information, and to diagnose and manage pre-cancerous conditions, cancer susceptibility, breast infections and other breast diseases.

SUMMARY OF THE INVENTION

It is therefore an object of the present invention to provide non-invasive methods and kits for obtaining biological samples that can be employed in assays for evaluating, diagnosing and managing breast disease, particularly cancer.

It is a further object of the invention to achieve the above object in assay methods and kits that are widely applicable to a broad range of patients, and that include useful assays and kits for screening early stage, nonpalpable mammary tumors.

It is yet another object of the invention to provide methods and kits that utilize the aforementioned biological samples to evaluate, diagnose and manage breast disease, preferably breast cancer, by detecting and/or measuring selected breast disease markers such as breast cancer markers, or panels of breast cancer markers, to provide highly specific prognostic and/or treatment-related information to the clinician.

The invention achieves these objects and other objects and advantages that will become apparent from the description which follows by providing non-invasive methods and devices for obtaining biological samples from a mammary organ of a mammalian patient. Through the use of novel, specialized breast pump devices of the invention, which are fluidly connected with (i.e., by direct or indirect coupling) a solid phase sample collection medium, the physician can rapidly and non-invasively collect mammary fluid samples from lactating or non-lactating female patients without additional intervention. Alternate methods of the invention for mammary fluid sample collection may involve administration of oxytocin, or an oxytocin analog, in an amount effective to stimulate or increase expression of mammary fluid induced in conjunction with employment of the breast pump device. The oxytocin or oxytocin analog (for example a long-acting oxytocin analog such as carbetocin) is administered in a manner (e.g., intranasally) and amount sufficient to reach and stimulate a target alveolar-ductal tissue of the breast, whereby the oxytocin stimulates myoepithelial contraction of the alveolarductal tissue to induce or facilitate mammary fluid expression. Alternatively, an intramuscular or intravascular injection of oxytocin can effect the same myoepithelial contraction response as the intranasal administration route. The amount, timing and/or mode of oxytocin administration may be adjusted on an individual basis depending on such factors as menstrual cycle stage, use of birth control or hormone replacement therapy, pregnancy history, age of onset of menarche, ethnicity and other factors known to affect an individual's propensity for breast fluid expression.

Mammary fluid collection devices of the invention are effective to induce mammary fluid expression for sample collection, alone or in conjunction with oxytocin stimulation. These devices are typically provided as a specialized breast pump which can be applied to the breast covering the nipple, and which typically directly receives the expressed mammary fluid. In preferred methods involving use of a breast pump, negative pressure is generated on the breast to induce expression of mammary fluid, optionally facilitated by prior or concurrent administration of oxytocin. In yet additional alternative methods, mammary fluid can be expressed and collected without the aid of a breast pump, which may require an increase of oxytocin dosage or lengthening of the post administration time period before the mammary fluid is fully expressed from the nipple.

During or after mammary fluid expression, a biological sample is collected from the expressed mammary fluid, which sample may consist of whole mammary fluid, whole cells, cell fragments, cell membranes, selected liquid, cellular or other solid fractions of the mammary fluid, as well as proteins, glycoproteins, peptides, nucleotides (including DNA and RNA polynucleotides) and other like biochemical and molecular constituents of the mammary fluid.

Sample collection can be achieved simply by receiving the expressed mammary fluid within any suitable reservoir, such as an ordinary sample storage container or assay vessel. In preferred embodiments of the invention, the expressed mammary fluid is exposed to a solid phase sample collection medium, simultaneous with or subsequent to the time of breast fluid expression. Suitable solid phase media in this context include microscopic glass slides, capillary tubes, coated tubes, microtiter wells or plates, membranes, filters, affinity columns, dot blot matrices, beads, microspheres, resins, and other like media that will selectively adsorb, bind, filter, partition or otherwise process desired components of the mammary fluid for convenient incorporation into a desired assay. Often it will be desirable to combine a plurality of solid phase media for sample collection, e.g., a filter and membrane, a membrane and a particulate medium, etc., for example to differentially partition and adsorb selected components of the breast fluid.

In conjunction with sample collection, the sample may be exposed to other agents such as buffers, diluents, extraction or chromatographic media, cross-linking agents, denaturing agents, etc., to stabilize or otherwise prepare the sample for processing within a desired assay.

Thus provided within the invention are methods and devices for obtaining a biological sample from a patient and/or determining the amount of a breast disease marker in a biological sample from breast fluid, which employ a novel breast pump or breast pump adapter. The breast pump functions in a similar fashion as a conventional breast pump but also provides a solid phase sample collection medium in fluid connection with the pump. The solid phase sample collection medium may be integrated within the breast pump or otherwise fluidly connected therewith, so that a sample of expressed mammary fluid contacts the collection medium, typically while the pump remains applied to the breast. In more detailed aspects of the invention, methods for employing the novel breast pump include a step of applying the breast pump to stimulate breast fluid expression, with or without prior oxytocin or carbetocin induction, wherein the solid phase sample collection medium is fluidly connected with a breast engaging portion or member of the breast pump.

According to these methods, operation of the pump results in an expressed breast fluid sample contacting the solid phase sample collection medium, typically while the pump remains applied to the breast. Within the foregoing methods, additional methods are provided which employ a novel, hand-held breast pump device, wherein a doctor, technician or patient collecting a breast fluid specimen can grasp and operate the hand-held pump to stimulate expression of breast fluid and collect a specimen thereof while keeping one hand free for additional tasks. The compact hand-held pump design allows the device to be picked up and manipulated with one hand, to seat the breast engaging element against the breast, apply vacuum pressure to the breast by manual operation of the vacuum pump to cause a suitable volume of breast fluid to be expressed at or near the nipple, and to simultaneously collect at least a primary sample of expressed breast fluid onto, or within, the solid phase sample collection medium without additional manual steps or a need to remove the device from the breast or engage two hands in the operation.

In certain collection methods of the invention, breast fluid expressed by use of the general purpose or hand-held breast pump is simultaneously or subsequently diluted, filtered, washed, admixed with fixative or other processing agents, or otherwise processed or modified to yield a collected fluid sample partially or completely devoid of cells, proteins and/or other selected components originally present in the expressed fluid, to provide a processed fluid sample for laboratory analysis. In other embodiments, particulate components of the breast fluid, for example, cells, cellular components and/or cellular debris, are collected after processing and/or modification, e.g., for cytological examination. Often, primary sample collection and/or processing in this context is coincident with the fluid contacting one or more solid phase collection medium(a) fluidly connected with the breast engaging member. Depending on the type(s) of medium(a) used, preliminary sample processing can also be achieved directly by simple operation of the hand-held pump, without the need for additional processing steps or removal of the breast engaging member from the subject's breast.

In other alternative methods within the invention, preliminary sample processing involves additional steps following breast fluid expression. In certain embodiments, the breast engaging member is removed from the breast after the breast fluid is expressed and the fluid is transferred to a first solid phase sample collection medium, typically a membrane or filter. This initial or primary stage of sample collection may be followed by washing or by manual transfer of selected breast fluid components (e.g., proteins, carbohydrates, cells, or cellular debris) from the first solid phase collection medium (e.g., a nitrocellulose membrane) to a second solid phase medium, e.g., a fluid-containing reservoir. Typically, preliminary sample processing in this regard precedes final packaging of the collected sample for storage or shipment to a lab for further processing and analysis of the sample. In one example, whole cells or other cellular materials are separated from expressed mammary fluid onto a nitrocellulose membrane or a filter, which is typically secured in fluid connection with the breast engaging member by a fixed or removable support member mounted to the engaging member or sample collection housing. The cells are subsequently transferred or washed in fluid (e.g., cytology fluid) to a second solid phase sample collection medium, for example a removable fluid reservoir connected to, or integrated with, the breast engaging member or sample collection housing.

In relation with these methods, various sample collection devices and accessories for use therewith are provided within more detailed embodiments of the invention. Typically, breast fluid collection devices of the invention include a breast engaging member constructed of a non-porous material that is sized and dimensioned to receive at least a nipple portion of a human breast and form a suction seal therewith. One or more solid phase sample collection media are provided in fluid connection with the breast engaging member for receiving a sample of expressed breast fluid. A vacuum pump mechanism is provided in gaseous connection with the breast engaging member for generating negative pressure through the breast engaging member to facilitate breast fluid expression.

In specific embodiments of the collection device of the invention, a sample collection housing is fluidly connected with the breast engaging member. The solid phase sample collection medium is often removably supported within the housing in proximity to the nipple when the breast engaging member is applied to the breast and negative pressure is generated by the vacuum pump mechanism. The solid phase sample collection medium can be one or more microscopic glass slides, capillary tubes, collection tubes, vials, columns, micro-columns, wells, plates, membranes, filters, resins, inorganic matrices, beads, resins, particulate chromatographic media, plastic microparticles, latex particles, coated tubes, coated templates, coated beads, or coated matrices.

Optional features of the breast fluid collection device include removable coupling means for removably coupling said sample collection housing with said breast engaging member. In other embodiments, the solid phase sample collection medium may be supported by a support member integrally or removably mounted within the sample collection housing in fluid connection with said breast engaging member. Various types of support members, including disposable or reuseable discs, cartridges and cassettes are provided as an accessory for use within the invention. In yet additional embodiments, a reciprocating mechanism for reciprocally adjusting a position of the solid phase sample collection medium relative to the breast engaging member is incorporated within the device. The reciprocating mechanism may incorporate a support member or carrier reciprocatingly mounted relative to the breast engaging member, which support member or carrier supports the solid phase sample collection medium. Yet another optional feature of the device includes a breast pump adapter employing concepts of the invention for collection of mammary fluid samples and operable in combination with a conventional breast pump.

In other detailed embodiments of the invention, the sample collection device is a hand-held breast pump incorporating the breast engaging member and the vacuum pump mechanism in a compact, structurally integrated breast fluid collection apparatus suitable for manipulation and operation using only one hand. In certain embodiments, hand-held breast pump comprises a modular device made up of a plurality of components, each joined or securable in fixed structural interconnection with one another and capable of partial or complete disassembly from remaining components to facilitate operation, cleaning, servicing and/or storage of the device. The modular breast pump can include, for example, a separate breast engaging member detachable from one or more interconnecting components of the device for cleaning or to allow interchanging of different engaging members to accommodate breast anatomy differences among patients.

Within more detailed embodiments of the hand-held breast pump, the solid phase sample collection medium can be supported by a support member removably mounted in fluid connection with the breast engaging member. The support member can be a removable cassette for removable placement in fluid connection with the breast engaging member. The support member can house any of the above identified collection media, and may incorporate one or more air channels that pass through a body of the support member for passage of vacuum pressure and/or sample materials between the breast engaging member and a sample collection housing member of the hand-held breast pump.

Within other detailed embodiments, the hand-held device includes a fluid-retaining recess, well or reservoir integrated or fluidly connected with the support member or a sample collection housing member of the device. The fluid-retaining recess, well or reservoir may comprise an integral, defined compartment or enclosure within the sample collection housing for receiving the breast fluid and/or constituent samples thereof. Alternatively, fluid-retaining recess, well or reservoir comprises a removable fluid reservoir member of the sample collection housing, typically provided as a rigid sample collection tube or vial removably connected with an outer casing member of the housing. The removable reservoir member is optionally sealably connected with the outer casing member of the housing to form an airtight coupling therewith. In certain embodiments, the removable reservoir member features a circumferential ridge, fin, O-ring or other sealable engagement means to engage and make an airtight seal against a wall or other surface of the casing member when the vial is nested within the casing member.

In additional detailed embodiments, the removable reservoir member is gaseously and fluidly connected with the breast engaging member to facilitate sample collection. For example, the vacuum pressure from the vacuum pump means may be routed to the breast engaging member through the removable reservoir member of the housing, which is modified to include one or more air ports that form a gaseous connection between a lumen of the reservoir and the vacuum pump means. The reservoir member may function in this context as both a conduit for vacuum pressure transmission to the breast and a receptacle for fluid sample materials to directly collect expressed fluid or as a secondary collection medium to receive primarily collected sample materials washed or otherwise transferred from a primary solid phase sample collection medium into the reservoir. For example, a primary solid phase sample collection medium fluidly connected with the breast engaging member may be positioned to collect a primary sample of one or more breast fluid components which can thereafter be washed or otherwise transferred directly or indirectly into the removable reservoir member, without removal or disassembly of the breast engaging member and reservoir member.

The fluid collection reservoir may serve a dual purpose for collection, as well as for storage, transport and/or processing of collected breast fluid or breast fluid component samples. Relating to this purpose, the removable reservoir member further comprises closure means for closing the reservoir after sample collection is completed to prevent sample contamination and spillage. The closure means may comprises a cap adapted to sealably engage a top end of the removable reservoir member. Where the reservoir member is modified to include one or more air ports for transmission of vacuum pressure between the lumen of the reservoir and the vacuum pump means, the closure means include secondary closure means to sealably close the air port(s) after sample collection. For example, the secondary closure means may comprise an adhesive seal or sticker sized and constructed to adhere to an outer wall of the reservoir member surrounding an air port opening. Typically, the secondary closure means comprises a combined closure and labeling device which functions as a secondary closure mechanism to seal the air port(s) of the removable reservoir, and as a labeling template to provide a writing surface for sample labeling. The combined closure and labeling tab or sticker generally includes a first, closure-forming surface for application over the air port to form a seal by juxtaposition or adhesive contact with an outer wall of the removable reservoir, and a second, labeling surface opposite the closure-forming surface made of a blank template material suitable for receiving a stable, ink or graphite imprint. In more detailed aspects, the secondary closure means comprises a combined closure and labeling tab or sticker which is pre-attached to the removable reservoir member in a first, open configuration and which can be manually repositioned or otherwise manipulated after sample collection to a second, closed configuration to form a seal or closure against the air port(s).

In related aspects of the invention, a novel breast fluid collection reservoir, e.g., a modified cytology vial, is provided for use within a mammary fluid collection device of the invention, which reservoir incorporates the foregoing features of the removable reservoir member of the sample collection housing. The novel collection reservoir thus provided is useful within the breast fluid collection methods of the invention, as well as within sample processing and diagnostic assay methods performed in the laboratory subsequent to collection of a breast fluid sample.

In related aspects of the invention, methods are provided for determining the presence or amount of a breast disease marker, preferably a breast cancer marker, in biological samples obtained from a mammary organ of a mammalian patient. These methods may involve intranasal, intramuscular or intravascular administration of oxytocin or an oxytocin analog to mammalian patients in amounts effective to stimulate mammary fluid expression in the patient. Once a sufficient post-administration time period has elapsed to allow the oxytocin to reach and stimulate target alveolar-ductal tissues, mammary fluid is collected directly from the nipple or, alternatively, the breast is pumped, and a biological sample from expressed mammary fluid is collected, as above. After the sample is collected a bioassay is conducted on the sample to determine the presence and/or amount of the breast disease marker in the sample. Suitable bioassays in this regard include assays to detect known markers of breast disease, such as assays employing immunological or other suitable probes to detect specific antigens and other markers expressed by selected pathogens, including bacterial and viral pathogens. More preferred bioassays will detect individual markers or panels of markers of benign breast tumors, pre-cancerous breast disease, and/or breast cancer, such as assays employing immunological or other suitable probes to detect specific antigens and other markers expressed by benign, pre-cancerous and/or cancerous alveolar-ductal cells of the breast. Preferably, the assay will detect the presence or amount of multiple breast disease markers in the biological sample, for example by including a panel of immunological or molecular probe(s) that bind or react with multiple breast cancer markers.

In yet additional aspects of the invention, clinically useful kits are provided for determining the presence and/or amount of a breast disease marker, preferably a breast cancer marker, in biological samples obtained from a mammary organ of a mammalian patient. The kits include a mammary fluid collection device in the form of a general purpose or hand-held breast pump as described herein. Additional kits include one or more breast pump attachments (e.g., a detachable breast engaging member, or multiple such attachments for use with different patients), accessories (e.g., replaceable fluid-retaining reservoirs), solid phase media, and/or disposable or reusable support members, cartridges or cassettes for holding collection media, as described herein. These and other kit components may be provided, alone or in any combination, with or without inclusion of the basic breast pump apparatus in the kit. Yet additional kits include a pharmaceutical preparation of oxytocin or an oxytocin analog in a biologically suitable carrier for use in alternate mammary fluid collection methods of the invention. Still other kits include on or more preparative and/or diagnostic reagents selected from those disclosed herein, including one or more fixatives, probes, labels and the like in separate or common containers. In certain embodiments of the invention, kits include compositions and/or devices for detecting the presence or amount of one or more breast disease marker(s) in the biological sample, often including one or more immunological or molecular probe(s) that binds or reacts with one or more breast cancer marker(s). The foregoing kit components are generally assembled in a collective packaging unit, which may include written or otherwise user-accessible instructions detailing the sample collection, handling and/or processing methods of the invention.

BRIEF DESCRIPTION OF THE DRAWINGS

FIG. 1 is a partial sectional view of a breast pump employing the concepts of the invention.

FIG. 2 is a sectional view of a portion of the breast pump as indicated in FIG. 1.

FIG. 9 is a partial sectional view of a portion of a breast pump illustrating a support member and cartridge for containing a particulate solid phase sample collection medium.

FIG. 10 is a partial sectional view of a portion of a breast pump illustrating a support member and an exemplary solid phase sample collection template (coated tube).

FIG. 11 is a partial sectional view of a breast pump employing a reciprocating mechanism to adjust positioning of a solid phase sample collection medium within the pump.

FIG. 12 is a sectional view depicting a breast pump adapter employing the concepts of the invention.

DESCRIPTION OF THE SPECIFIC EMBODIMENTS

Figure 3:
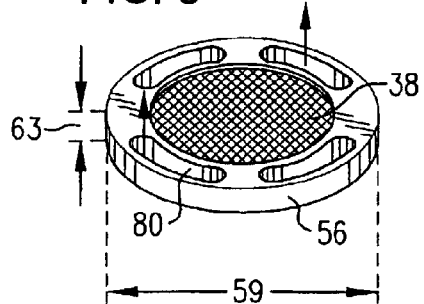
FIG. 3 is a perspective view of a support member for supporting a solid phase sample collection medium in fluid connection with a breast pump.

As noted above, the invention provides methods and devices 10, 10' for obtaining, handling, and processing biological samples from mammary fluid. Preferably, these methods are non-invasive, meaning they are non-surgical and do not involve penetration of the breast by needles or other intrusive devices. To practice the noninvasive sample collecting method, the invention provides specialized breast pump devices which feature a breast engaging portion or member coupled with a vacuum pump mechanism and fluidly connected with a solid phase sample collection medium. The mammary fluid collection devices and methods disclosed herein are related in certain aspects to mammary fluid collection devices and methods disclosed in U.S. patent application Ser. No. 09/435,131, filed Nov. 05, 1999, U.S. patent application Ser. No. 09/027,362, filed Feb. 20, 1998, and U.S. Pat. No. 5,798,266, issued Aug. 25, 1998, each incorporated herein by reference. The devices and methods of the present invention are effective to induce mammary fluid expression for sample collection, alone or in conjunction with oxytocin stimulation.

The mammary fluid collection devices of the invention are typically provided as a specialized breast pump 10, 10' which can be applied to a human or animal breast covering the nipple, and which typically receives expressed mammary fluid within a solid phase sample collection medium, and in some cases within a removable sample collection reservoir. During or after mammary fluid expression, a biological sample is collected from the expressed mammary fluid, which sample may consist of whole mammary fluid, whole cells, cell fragments, cell membranes, selected liquid, cellular or other solid fractions of the mammary fluid, as well as proteins, glycoproteins, peptides, nucleotides (including DNA and RNA polynucleotides) and other like biochemical and molecular constituents of the mammary fluid.

The breast pump devices 10, 10' of the invention function in part by generating negative pressure applied to the nipple area of the breast to induce mammary fluid expression. Fluid expression induced by these breast pump devices may optionally be facilitated by coordinate administration of the peptide hormone oxytocin, or a functional analog thereof, in an amount effective to stimulate or increase expression of mammary fluid induced by the breast pump device. The oxytocin or oxytocin analog (for example a long-acting oxytocin analog such as carbetocin) is administered in a manner (e.g., intranasally) and amount sufficient to reach and stimulate a target alveolar-ductal tissue of the breast, whereby the oxytocin stimulates myoepithelial contraction of the alveolar-ductal tissue to induce or facilitate mammary fluid expression.

During or after the mammary fluid expression step, a biological sample is collected from the expressed mammary fluid. A range of suitable biological samples are contemplated and will be useful within the methods of the invention, including whole mammary fluid, selected liquid or solid fractions of the mammary fluid, whole cells or cellular constituents, proteins, glycoproteins, peptides, nucleotides (including DNA and RNA polynucleotides) and other like biochemical and molecular constituents of the mammary fluid. Sample collection can be achieved simply by receiving the expressed mammary fluid within a suitable reservoir, such as an ordinary sample storage container or assay vessel.

In preferred embodiments of the invention, the expressed mammary fluid is contacted with a solid phase sample collection medium fluidly connected with the breast pump 10, 10', simultaneous with or subsequent to the time of breast fluid expression. Suitable solid phase media in this context include microscopic glass slides, capillary tubes, coated tubes, microtiter wells or plates, membranes, filters, affinity columns, dot blot matrices, beads, resins, and other like media that will selectively adsorb, bind, filter, partition or otherwise process desired components of the mammary fluid for convenient incorporation into a desired assay.

A wide range of sample collection procedures and materials known in the art are useful within the invention. Selected methods and materials will vary among different assays, as will be understood and readily practiced by those skilled in the art. For example, if the breast disease marker sought in a particular assay is a soluble protein, it will often be desired to immobilize the protein on a solid phase matrix or template by contacting the target protein with a reagent having high specificity for the protein, preferably a polyclonal or monoclonal antibody. The yields a complex, e.g., a ligand-protein complex, an antibody-antigen complex, or other complex in which the target protein is bound to a specific binding partner (i.e., wherein the complex is not dissociated upon addition of a non-specific binding partner conventionally used as a control to determine specific binding; and preferably wherein the binding partner binds with an affinity of kD 10-9 or greater). The binding partner that binds to the target protein is in turn immobilized to the solid phase medium, before or after complex formation with the target protein. Immobilization of the binding partner, e.g., by covalent binding to a solid phase template or matrix, can be achieved by a variety of conventional methods known in the art.

In this manner, the target protein/binding partner complex is adsorbed or otherwise bound directly to an insoluble matrix. Alternatively, a variety of secondary binding partners, e.g., anti-isotype antibodies, may be added to bind the complex to the insoluble matrix. The latter step depends on the nature of the first binding partner (i.e., the binding agent that specifically binds the target protein), for example whether the first binding partner is a primary antibody, ligand, etc.

Particularly useful within the invention are immunoassay which formats employ a combination of solid phase or immobilized reagents and labeled reagents whereby the association of the label with the solid phase is a function of the presence or absence of reactivity with the targeted antigen. In general, such a solid phase reagent comprises a binding substance such as an anti-antibody (e.g., anti-IgG), or other immunobinder or other binding agent according to the assay protocol involved, bound or attached, covalently or noncovalently, to the solid phase matrix or in an otherwise immobilized form.

Useful labeled reagents in solid phase immunoassays include a binding substance such as an anti-antibody (e.g., anti-IgG), or other immunobinder or other binding agent according to the assay protocol involved, which is chemically coupled with a detectable chemical moiety. Useful labels are conventional in the art and include fluorescers, chemiluminescers, radioisotopes, and enzymes. Enzyme labels are particularly useful and are generally selected from alkaline phosphatase, peroxidase, and $\beta$-galactosidase. Enzyme labels are readily detectable by addition of a corresponding chromogenic substrate and detecting the resulting color or fluorescent response.

A variation of this protocol uses a ligand-modified form of the targeted antigen(s) with immobilization to the solid phase being accomplished by using a solid phase bearing an immobilized (e.g., bound or adsorbed) binding partner to the ligand. For example, biotin or a hapten (e.g., fluorescein) can be used as the ligand and can be immobilized by contact with a solid phase form of avidin or anti-hapten antibody, respectively. The addition of the solid phase binding partner can occur at any convenient time in the assay, such as prior to contact of sample with the ligand-antigens(s) or thereafter.

Preferred solid phase matrices for use within the foregoing methods include *Staphylococcus aureus* or Protein A or G Agarose [e.g. Sepharose® (Pharmacia Biotech AB, Uppsala, Sweden)] beads. Protein A and protein G are cell wall proteins isolated from specific bacterial strains, and have specific binding sites for certain classes of immunoglobulins. Protein A binds (to varying degrees) most subclasses of IgG, plus IgM, IgA, and IgD. Protein G binds nearly all subclasses of IgG, but not other classes of immunoglobulins.

An alternative solid phase sample collection and/or assay method utilizes a specific anti-marker primary antibody that is covalently attached to the solid phase matrix, e.g., by covalent linking the antibody through its free amino groups to cyanogen-bromide-activated Sepharose particles. Insolubilized antibody can be used to pull the corresponding marker antigen out of solution by adsorption to its surface. In yet another alternative format, the marker protein can be treated with a cross-linking reagent (e.g. biotin or digoxigenin) that may be subsequently detected by a second binding partner. In the case of biotin, the second binding partner is avidin or streptavidin; for digoxigenin, the second reagent is an anti-digoxigenin antibody. Avidin and streptavidin may be coupled directly to the solid phase medium, e.g., to agarose beads. Because the initial biotinylation is not specific for the marker, samples are frequently electrophoresed on, e.g., SDS PAGE, transferred to nitrocellulose etc., and Western blotted with antibodies specific for the protein factor.

A preferred assay method for detecting protein markers is the well known, Enzyme Linked Immunosorbant Assay (ELISA) assay. According to this method, a variety of coating reagents can be adsorbed or otherwise bound directly onto a surface of a desired solid phase sample collection medium, e.g., a microtiter plate, well, tube, bead, test strip, plastic microparticle, latex particle, etc., to form a coated template or matrix. These coating reagents are typically a species-specific anti-isotype antibody (e.g., antimouse-IgG) but can also include an anti-marker primary antibody or an affinity reagent such as avidin or streptavidin. The target protein (e.g., a soluble protein marker) is contacted with a specific primary antibody or, alternatively, is crosslinked (e.g., to biotin) or otherwise modified to form a complex, and the resulting complex is adsorbed to the coated template or matrix and processed according to conventional assay methods.

Latex or particle agglutination methods are also to be mentioned. Particles are coated or covalently coupled with a target antigen, ligand, antibody or other binding partner. The particles are then incubated with a test sample and resulting agglutination of the particles, e.g., due to formation of ICA antibody linkages between particles, is detected. Detection can be accomplished by visual observation (e.g., a slide agglutination format) or quantified by measuring turbidity changes with a spectrophotometer or nephelometer. A well known variation of this general method based on inhibition of particle agglutination can also be employed. In addition, an agglutinator reagent can be prepared comprising multiple antigens, e.g., a water soluble polymer backbone to which are attached multiples of one or more antigens within a panel.

Alternative methods for collecting and analyzing samples within the invention include Western immunoblot and dot-blot methods. For application of these methods, the solid phase sample collection medium is preferably a membrane or filter, e.g., a nitrocellulose, polyvinylidene difluoride (PVDF), or nylon membrane. Proteins within the breast fluid sample may be processed (e.g., separated on SDS PAGE) or directly transferred to the membrane, and non-specific interactions may be blocked by incubating the membrane with, e.g., bovine serum albumin/ovalbumin or non-fat dry milk. A primary antibody with specificity for the protein marker is contacted with the membrane, and excess antibody is washed, e.g., with buffered detergent. A labeled isotype specific antibody is next contacted with the membrane, and target protein-primary antibody-secondary antibody ternary complexes are detected, e.g., calorimetrically.

Where the targeted protein factor includes a carbohydrate moiety, the factor can also be adsorbed to a solid phase template or matrix, e.g., a resin, by way of lectin-carbohydrate interactions. Various lectins are available for this purpose that differ in their carbohydrate binding specificity. For example, Lectin Con A binds to mannose-containing carbohydrate structures and with low affinity to $\alpha$-glucose and $\alpha$-N-acetylglucosamine. Lectin GNA binds to terminal mannose residues. Lectin MAA binds to $\alpha(2-3)$ Linked sialic acids. A variety of other lectins collectively providing a wide range of specificities are known in the art.

A particularly preferred solid phase sample collection medium for use within the invention is a filter, pad or membrane that can be directly contacted to a sample of expressed breast fluid to adsorb, absorb, bind, partition or otherwise facilitate sample processing or handling within a selected assay. For this purpose, several types of transfer membranes are known, including nitrocellulose which is the most commonly used transfer membrane. Several commercial sources now offer nitrocellulose impregnated with a synthetic support that improves its durability and flexibility without altering its performance. One preferred transfer membrane, polyvinylidene difluoride (PVDF), marketed by Millipore (Bedford, Mass.) under the trade name Immobilon®, has slightly lower protein-binding capacity than nitrocellulose but is mechanically stronger and compatible with many organic solvents. This allows direct protein staining with Coomassie Blue, and direct amino acid composition and sequence analysis of transferred proteins, without interfering with its subsequent use for antibody probing.

Membranes are not only useful within the invention for protein blotting, but also for immobilization of nucleic acids. Thus, nitrocellulose, reinforced nitrocellulose, diazotized membranes (paper or nylon), nylon, charged nylon, or PVDF, and DEAE-anion exchange membranes are useful for immobilizing DNA and RNA from expressed breast fluid. In this context, the most commonly used membranes are reinforced nitrocellulose and nylon. Nitrocellulose has a lower background but also a lower binding capacity than nylon and is chosen primarily when background, but not detectability, is the main concern. Nylon, in contrast, is ideal for lower copy number sequences, short target sequences (down to oligomers) or for reprobing. Membranes are also available with different pore sizes. For DNA blots, membranes with a pore size of 0.45 $\mu$m are usually chosen for large fragments, but 0.22 $\mu$m for fragments of <500 bases. For RNA blots, membranes with a pore size of 0.1 or 0.22 $\mu$m are most efficient. Membranes are available in different size specifications, including sheets, rolls, pre-cut circles, etc.

Methods for detecting DNA on nylon without DNA purification and processing of the samples, e.g., for detecting DNA from fluids or whole cells, have recently been developed (Reed and Matthaei, *Nucleic Acids Res.* 18:3093, 1990; and Hammermueller et al., *J. Virol. Methods* 31:47, 1991; each incorporated herein by reference). These procedures avoid enzymatic dispersion of cells, RNase and pronase treatments to hydrolyze cellular macromolecules, etc., and are typically based on the capacity of alkali and other reagents to disperse and solubilize cells and hydrolyze macromolecules including RNA and protein, but not DNA. Positively charged modified nylon membranes then irreversibly bind nucleic acid while remaining suitable for hybridization.

Nucleic acid extraction and processing steps may also be minimized by well known fast blot methods. In particular, fast blot methods that use nylon as a solid phase take advantage of the ability of NaOH to dissociate cells, denature DNA and immobilize DNA. Nitrocellulose membranes have a lower binding capacity and co-immobilization of nucleic acid and protein from neutral solutions can be a problem. Concentrated NaI can be used to inhibit protein immobilization, to denature DNA and to irreversibly bind the nucleic acid to nitrocellulose without a requirement for baking. This method can also be used for RNA.

Although it is possible to directly transfer proteins, nucleic acids and other markers to a solid phase matrix which is in turn directly incorporated in an assay, it may be desirable to concentrate the target marker, e.g., by chromatography, extraction, specific or nonspecific adsorption, etc., particularly when sensitivity is a problem. Thus, samples can be collected and initially processed by contacting breast fluid with a solid phase chromatographic medium, e.g., within a cartridge comprising a micro-column of Sepharose-coupled antibody. Up to 500-fold increases in immunoassay sensitivity with apparent recoveries of 85 to 95% can be achieved using this approach. This and other well known chromatographic procedures provide a powerful approach to the quantitation of substances too dilute to be measured by routine methods.

For sample collection and processing using chromatographic and related methods, a particulate solid phase sample collection medium is preferred. Various particulate media are known which selectively adsorb, absorb, bind, or partition components of biological samples, which media are readily adapted for collection and processing of breast fluid samples. These particulate can be coupled with various coating reagents known in the art, e.g., affinity reagents, to provided a coated medium, or may be used in an unmodified form.

Exemplary particulate sample collection media for use within the invention include beads, plastic microparticles, latex microspheres, glass materials such as controlled porous glass, granular agarose based materials, cross-linked dextran polymers, inorganic or organic ion exchanger materials, kieselsur and other silicate materials. Suitable materials additionally include cellulosic materials, e.g., diethylaminoethyl (DEAE) cellulose or diethylamino (DEA) cellulose. Also useful are natural polymeric carbohydrates and their synthetically modified, cross-linked or substituted derivatives, such as agar, agarose and cross-linked dextran polymers.

Synthetic polymers which can be prepared with suitably porous structures, such as vinyl polymers (e.g., polyethylene, polypropylene, polystyrene, polyvinylchloride, polyvinylacetate and its partially hydrolysed derivatives, polyacrylates, polyacrylamides, polymethacrylates), copolymers and terpolymers of the above vinyl monomers among themselves and with other monomers, polycondensates (e.g., polyesters and polyamides), and addition polymers, such as polyurethanes or polyepoxides are also useful.

Yet additional particulate media are prepared from inorganic materials having a suitably porous form, such as sulfates or carbonates of alkaline earth metals and magnesium. Examples include barium sulfate, calcium sulfate, calcium carbonate, magnesium carbonate, silicates of alkali and alkaline earth metals and/or aluminum and/or magnesium, and aluminum or silicon oxides or hydrates, such as clays, alumina, talc, kaolin, zeolite, among others.

Also included among useful solid phase sample collection media porous barrier materials suitable for use with breast pump and breast pump adapter devices of the invention, for example to enclose particulate solid phase media within a cartridge adapted for coupling in fluid connection with a breast pump or breast pump adapter. Such porous barrier materials are inert to and nonreactive with markers and other analytes and reagents used in assaying for breast disease markers, and are porous with respect to the passage of liquids and/or particulates of a pre-selected size. Suitable materials include various porous materials such as nylon fabric, polyethylene and other plastic films, membranes, filters, glass wool, sponge, styrofoam, ceramic and other porous materials.

In conjunction with sample collection, samples of expressed breast fluid may be exposed to other agents such as buffers, diluents, extraction or chromatographic media, cross-linking agents, blocking agents, denaturing agents, etc., to stabilize or otherwise prepare the sample for processing within a desired assay. For example, the sample may be diluted (e.g., by collecting the sample in a well or recess containing the solid phase medium wetted or suspended in a diluent) to minimize nonspecific binding effects, e.g., affecting a subsequent immunoassay. In the exemplary context of sample collection for immunoassays, the avidity of the antibody for the marker antigen is an important consideration, whereby providing more or less diluent during sample collection and incubation may optimize a particular antigen-antibody system being studied.

Commonly used buffers for dilution include phosphate, borate, or Tris-buffered saline. Usually, the choice of the buffer is not important. Nonetheless, a careful examination of the effect of buffer, pH, ionic strength, and divalent cations will facilitate use of a new sample collection/assay system in order to maximize sensitivity and resolve possible sources of interference within the assay. Although immunoassays are usually carried out at neutrality, doing so is not always optimal.

Nonspecific binding or adsorption, e.g., of antigens and haptens (especially hydrophobic haptens) to glass and plastic tubes or pipettes may markedly influence measured activity in a particular immunoassay. With some proteins and polypeptides, nonspecific binding in immunoassays is reduced if plastic tubes are used. The addition of protein to the medium may also minimize nonspecific adsorption and help avoid denaturation of highly diluted antigens and antibodies. Therefore, assays involving iodinated antigens are generally carried out in protein-containing buffers. Bovine serum albumin, gelatin, lysozyme, and ovalbumin are commonly used, usually at final concentrations of 1 to 5 mg/ml. In some systems diluted whole serum or proteins present in the sample itself are just as satisfactory. However, even though added proteins are often beneficial, they should not be used indiscriminately without making an evaluation for possible adverse effects, for example contaminating enzymes that may degrade the marker protein.

Other possible additives for improved sample collection and assay methods, apart from buffer and protein, include enzyme inhibitors and chelating agents. In assays lasting longer than 3 days, a bacteriostatic agent, such as sodium azide, 0.1 to 0.2%, may also be incorporated into the sample collection and/or assay medium to help avoid microbial growth.

Although a fundamental utility of the present invention lies in the novel, non-invasive methods for obtaining biological samples from mammary fluid, additional methods are disclosed herein that provide useful assays for detecting and/or measuring important breast disease markers in these samples. In this context, the invention provides a broad range of assay methods incorporating known procedures and reagents for determining the presence and/or expression levels of breast disease markers, particularly breast cancer markers, in biological samples. As incorporated within the invention, these methods involve application of a breast pump 10, 10' to mammalian patients, optionally coupled with oxytocin administration in amounts effective to facilitate mammary fluid expression in the patient. After the sample is collected, a bioassay is conducted on the sample to determine the presence and/or amount of a selected breast disease marker, preferably a breast cancer marker or panel of breast cancer markers, in the sample.

As used herein, the term breast disease marker refers to any cell, cell fragment, protein, peptide, glycoprotein, lipid, glycolipid, proteolipid, or other molecular or biological material that is uniquely expressed (e.g. as a cell surface or secreted protein) by diseased breast cells, or is expressed at a statistically significant, measurably increased or decreased level by diseased breast cells, or in association with breast disease (e.g. a protein expressed by an infectious agent associated with breast disease), or is expressed at a statistically significant, measurably increased or decreased level by diseased breast cells compared to normal breast cells, or which is expressed by non-diseased breast cells in association with breast disease (e.g. in response to the presence of diseased breast cells or substances produced therefrom). Breast disease markers can also include specific DNA or RNA sequences marking a deleterious genetic change, or an alteration in patterns or levels of gene expression significantly associated with breast disease. Preferred breast disease markers include markers of breast infections, benign neoplasia, malignant neoplasia, pre-cancerous conditions, and conditions associated with an increased risk of cancer.

As used herein, the term breast cancer marker refers to a subset of breast disease markers, namely any protein, peptide, glycoprotein, lipid, glycolipid, proteolipid, or other molecular or biological material that is uniquely expressed (e.g. as a cell surface or secreted protein) by cancerous cells, or is expressed at a statistically significant, measurably increased or decreased level by cancerous cells compared to normal cells, or which is expressed by non-cancerous cells in association with cancer (e.g. in response to the presence of cancerous cells or substances produced therefrom). Breast cancer markers can also include specific DNA or RNA sequences marking a deleterious genetic change, or an alteration in patterns or levels of gene expression significantly associated with cancer. In addition, breast cancer markers can include cytological features of whole cells present in mammary fluid, such as nuclear inclusions or cytoplasmic structures or staining attributes uniquely expressed by, or associated with, cancerous cells.

Among the breast cancer markers that are useful within the methods of the invention, a subset are described in representative review articles by Porter-Jordan et al., *Hematol. Oncol. Clin. North Amer.* 8:73–100, 1994; and Greiner, Pharmaceutical Tech, May, 1993, pp. 28–44, each incorporated herein by reference in its entirety. Other suitable markers are also widely known and can be readily incorporated into the methods of the invention using information and methods generally known or available in the literature. Preferred breast cancer markers for use within the invention include well characterized markers that have been shown to have important value for determining prognostic and/or treatment-related variables in human female patients. As noted previously, prognostic variables are those variables that serve to predict outcome of disease, such as the likelihood or timing of relapse or survival. Treatment-related variables predict the likelihood of success or failure of a given therapeutic program. Determining the presence or level of expression or activity of one or more of these markers can aid in the differential diagnosis of patients with malignant and benign abnormalities, and can be useful for predicting the risk of future relapse or the likelihood of response to a selected therapeutic option.

It is important to note, however, that the invention does not rely solely on breast disease markers that meet the stringent requirements of sensitivity and specificity that would render the marker immediately acceptable for clinical application to human patients. On the contrary, a number of breast disease markers contemplated within the invention fall short of these stringent criteria, and nonetheless provide useful information that can be of substantial benefit in detecting, differentially diagnosing or managing breast cancer. Such non-clinically accepted markers are useful for immediate application within the methods of the invention as basic research tools, and as adjunctive tools in clinical applications. Beyond these immediate applications, many such markers are expected to be further developed and refined according to the methods of the invention to the point of direct clinical applicability, particularly in assay methods that analyze combinations of markers to generate complementary data of greater predictive value than data yielded by individual markers alone.

The preferred assay methods of the invention particularly focus on breast cancer markers associated with tumorigenesis, tumor growth, neovascularization and cancer invasion, and which by virtue of this association provide important information concerning the risk, presence, status or future behavior of cancer in a patient. As noted previously, tumorigenesis and tumor growth can be assessed using a variety of cell proliferation markers (for example Ki67, cyclin D1 and PCNA). Tumor growth can also be evaluated using a variety of growth factor and hormone markers (for example estrogen, EGF, erbB-2, and TGF-α, receptors of autocrine or exocrine growth factors and hormones (for example IGF and EGF receptors), or angiogenic factors. In addition to tumorigenic, proliferation and growth markers, a number of markers provide information concerning cancer invasion or metastatic potential in cancer cells, for example by indicating changes in the expression or activity of cell adhesion or motility factors. Exemplary markers in this context include Cathepsin D, plasminogen activators and collagenases. In addition, expression levels of several putative tumor "suppressor" genes, including nm23, p53 and rb, provide important data concerning metastatic potential, or growth regulation of cancer cells. A large number and variety of suitable breast cancer markers in each of these classes have been identified, and many of these have been shown to have important value for determining prognostic and/or treatment-related variables relating to breast cancer.

Prior to or concurrent with each assay run of the invention, it may be preferable to perform a preliminary evaluation to verify sample origin and/or quality. The focus of such preliminary evaluations is to verify that the sample collected from expressed mammary fluid is indeed of mammary origin, and is not contaminated with other potential contaminants, such as sweat from skin surrounding the nipple. For these sample verification purposes, a variety of assays are available which identify mammary fluid markers known to be present in mammalian mammary fluid, and which are preferably highly specific markers for mammary fluid (i.e. markers which are typically always present in mammary fluid and which are absent from all, or most of, other potentially contaminating bodily fluids and tissues). However, an acceptable level of specificity for mammary fluid markers within the methods of the invention is provided by markers that are simply known to be present in mammary fluid, even though they may be present in other bodily fluids. One such marker is the enzyme lysozyme, which is a normal component of human serum, urine, saliva, tears, nasal secretions, vaginal secretions, seminal fluid, and mammary fluid. Lysozyme (muramidase) is an enzyme which hydrolyzes beta 1,4-glycosidic linkages in the mucopolysaccharide cell wall of a variety of microorganisms resulting in cell lysis. Quantitative measurement of lysozyme is readily accomplished by a well known agar plate diffusion method, described in detail in the instructions provided with the Quantiplate® lysozyme test kit, available from Kallestad, Sanofi Diagnostics (Chasta, Minn.), incorporated herein by reference in its entirety.

Other mammary fluid markers for sample verification that are more specific than lysozyme are preferred within the methods of the invention, and can be readily incorporated within the invention based on published and generally known information. The most preferred among these markers are proteins and other biological substances that are specifically expressed or enriched in mammary fluid. A diverse array of suitable markers in this context have been characterized and have already been used to develop specific antibodies, including affinity purified and monoclonal antibodies. These antibodies can in turn be employed as immunological probes to determine the presence or absence, and/or to quantify, selected mammary fluid markers to verify mammary fluid sample origin and quality. Mammary fluid markers of particular interest for use within the invention include specific cytokeratins that are characteristically expressed by normal and cancerous mammary epithelial cells, against which specific panels of antibody probes have already been developed. (See for example, Nagle, J., *Histochem. Cytochem.* 34:869–881, 1986, incorporated herein by reference in its entirety). Also useful as mammary fluid markers are the human mammary epithelial antigens (HME-Ags) corresponding to glycoprotein components of the human milk fat globulin (HMFG) protein, against which specific antibodies (e.g., anti HMFG1, Unipath, U.K.) are also available. (See Rosner et al., *Cancer Invest.* 13:573–582, 1995; Ceriani et al. *Proc. Natl. Acad. Sci. USA* 74:582–586, 1982; Ceriani et al., *Breast Cancer Res. Treat.* 15:161–174, 1990, each incorporated herein by reference in its entirety).

To conduct the breast disease marker assays provided within the invention, a collected biological sample from mammary fluid is generally exposed to a probe that specifically binds to a selected breast disease or breast cancer marker, or otherwise interacts with the marker in a detectable manner to indicate the presence or absence, or amount, of the breast disease or breast cancer marker in the sample. Selected probes for this purpose will generally depend on the characteristics of the breast disease marker, i.e. on whether the marker is a protein polynucleotide or other substance. In preferred embodiments of the invention, the breast disease marker is a protein, peptide or glycoprotein, all of which are effectively targeted in breast disease marker assays using specific immunological probes. These immunological probes can be labeled with a covalently bound label to provide a signal for detecting the probe, or can be indirectly labeled, for example by a labeled secondary antibody that binds the immunological probe to provide a detectable signal.

General methods for the production of non-human antisera or monoclonal antibodies (e.g., murine, lagormorpha, porcine, equine) are well known and may be accomplished by, for example, immunizing an animal with a selected breast disease marker protein, peptides synthesized to include part of the marker protein sequence, degradation products including part of the marker protein sequence, or fusion proteins including all or part of the marker protein linked to a heterologous protein or peptide. Within various embodiments, monoclonal antibody producing cells are obtained from immunized animals, immortalized and screened, or screened first for the production of an antibody that binds to the selected breast cancer marker protein or peptide, and then immortalized. It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397 (incorporated herein by reference in its entirety). Alternatively, a human monoclonal antibody or portions thereof may be identified by first screening a human B-cell cDNA library for DNA molecules that encode antibodies that specifically bind to the selected breast disease marker according to the method generally set forth by Huse et al. (*Science* 246:1275–1281, 1989 (incorporated herein by reference in its entirety). The DNA molecule may then be cloned and amplified to obtain sequences that encode the antibody (or binding domain) of the desired specificity.

Also contemplated within the invention are bifunctional antibodies having independent antigen binding sites on each immunoglobulin molecule (as disclosed for example in *Thromb. Res. Suppl.* X:83, 1990, and in *The Second Annual IBC International Conference on Antibody Engineering*, A. George ed., Dec. 16–18, 1991; each incorporated herein by reference in its entirety), as well as panels of individual antibodies having differing specificities. Bifunctional antibodies and antibody panels of particular use within the invention include antibodies and panels of antibodies that bind to two or more selected breast disease markers to generate complementary data of greater predictive value than data yielded by individual markers alone.

Monoclonal antibodies are particularly useful within the invention as labeled probes to detect, image and/or quantify the presence or activity of selected breast disease markers. In this context, monoclonal antibodies that specifically bind to selected breast disease markers are provided which incorporate one or more well known labels, such as a dye, fluorescent tag or radiolabel. By incorporating such a label, the antibodies can be employed in routine assays to determine expression, localization and/or activity of one or more selected breast disease markers in a biological sample including, or derived from, mammary fluid. Results of these assays to determine expression, localization and/or activity of a selected breast disease marker in a test sample taken from a patient at risk for breast disease, or known to have breast disease, can be compared to results from control studies detecting and/or quantifying the same marker in biological samples obtained from normal patients negative for breast disease. In this manner, baseline data and cutoff values can be determined according to routine methods to refine the assays of the invention and adapt them for direct clinical application.

Detection and/or quantification of breast disease markers in the biological samples of the invention can be accomplished using a variety of methods. Preferred methods in this regard include well known ELISA immunoassays, immunoprecipitation assays, and various solid phase immunoassays including Western blotting, dot blotting and affinity purification immunoassays, among other methods. Comparable methods are disclosed herein, or are elsewhere disclosed and known in the art, for using non-antibody probes to detect and/or quantify the expression and/or activity of breast disease markers. Suitable non-antibody probes for use within the invention include, for example, labeled nucleotide probes that hybridize at moderate or high stringency to DNA transcripts of oncogenes and other DNA sequences associated with elevated breast disease risk, or with mRNA transcripts encoding breast disease marker proteins. Preferably, the nucleotide probes hybridize with a target sequence under high stringency conditions. As used herein, "moderate stringency" and high stringency" refers to finite ranges of hybridization conditions that are well established in the literature. (See, for example: Sambrook et al., *Molecular Cloning: A Laboratory Manual*, Cold Spring Harbor, N.Y., Cold Spring Harbor Press, 1989; Hames and Higgins, eds., *Nucleic Acid Hybridization: A Practical Approach*, IRL Press, Washington D.C., 1985; Berger and Kimmel, eds, *Methods in Enzymology*, Vol. 52, Guide to Molecular Cloning Techniques, Academic Press Inc., New York, N.Y., 1987; and Bothwell, Yancopoulos and Alt, eds, *Methods for Cloning and Analysis of Eukaryotic Genes*, Jones and Bartlett Publishers, Boston, Mass. 1990; each of which is incorporated herein by reference in its entirety. Moderate or high stringency hybridization conditions are achieved, e.g., by adjusting the temperature of hybridization, adjusting the percentage of helix-destabilizing agents such as formamide in the hybridization mix, and adjusting the temperature and salt concentration of the wash solutions. Alternatively, stringency can be adjusted during post-hybridization washes by varying the salt concentration and/or the temperature. Stringency of hybridization may be reduced by reducing the percentage of formamide in the hybridization solution or by decreasing the temperature of the wash solution. Typical high stringency conditions require, for example, high temperature hybridization (e.g., 65–68° C. in aqueous solution containing 4–6×SSC, or 42° C. in 50% formamide) combined with a high temperature (e.g., 5–25° C. below the Tm) wash and a low salt concentration (e.g., 0.1×SSC). In contrast, moderate stringency conditions involve, for example, hybridization at a temperature between 50° C. and 55° C. and washes in 0.1×SSC, 0.1% SDS at between 50° C. and 55° C., which should be sufficient to identify polynucleotide molecules encoding I-mf from other species or to isolate isoforms of I-mf. In further contrast, low stringency conditions involve, for example, low hybridization temperatures (e.g., 35–42° C. in 20–50% formamide) and intermediate temperature (e.g., 40–60° C.) washes in a higher salt concentration (e.g., 2–6×SSC).

In certain preferred embodiments of the invention, cDNA and oligonucleotide probes are employed in well known Northern, Southern and dot-blot assays for identifying and quantifying the level of expression of a selected breast disease marker in cell samples collected from expressed mammary fluid.

Other suitable probes for use within the invention include labeled ligands, binding partners and co-factors of breast disease markers (e.g. growth factor receptor ligands, or substrates of breast cancer associated proteases such as cathepsin D).

Measuring the level of expression of breast disease markers according to the foregoing methods will provide important prognostic and treatment-related information for assessing a broad range of breast disease, including the genesis, growth and invasiveness of cancer, in mammals, particularly humans. For example, assays utilizing oligonucleotide probes will assist early screening to evaluate heritable genetic lesions associated with breast cancer, and to distinguish between pre-cancerous, early cancerous and likely metastatic lesions in patients.

In addition to the above mentioned sample collection and assay methods, the invention also provides kits and multi-container units comprising devices, components, accessories, reagents and other related materials for practicing the sample collection and assay methods of the invention. These kits are clinically useful for collecting, handling and/or processing mammary fluid samples, e.g., for determining the presence and/or amount of a breast disease marker, preferably a breast cancer marker, in the biological samples. The kits include a mammary fluid collection device having a breast engaging member, vacuum pump, and sample collection means incorporated in a general purpose or hand-held breast pump as described herein. Additional kits include one or more breast pump attachments (e.g., a detachable breast engaging member, or multiple such attachments for use with different patients), accessories (e.g., replaceable fluid-retaining reservoirs), solid phase media, and/or disposable or reusable support members, cartridges or cassettes for holding collection media, as described herein. These and other kit components may be provided, alone or in any combination, with or without inclusion of the basic breast pump apparatus in the kit. Yet additional kits include a pharmaceutical preparation of oxytocin or an oxytocin analog in a biologically suitable carrier for use in alternate mammary fluid collection methods of the invention. Preferably, the oxytocin preparation is provided in an intranasal spray applicator and contains approximately 40 USP units of oxytocin per ml of liquid carrier, which carrier is a simple, inexpensive buffered saline solution. Preferred applicators can be in any of a variety of pressurized aerosol or hand-pump reservoir forms, with a nozzle for directing a liquid spray of the oxytocin into a patient's nostril. Still other kits include on or more preparative and/or diagnostic reagents selected from those disclosed herein, including one or more fixatives, probes, labels and the like in separate or common containers. In certain embodiments of the invention, kits include compositions and/or devices for detecting the presence or amount of one or more breast disease marker(s) in the biological sample, often including one or more immunological or molecular probe(s) that binds or reacts with one or more breast cancer marker(s). The foregoing kit components are generally assembled in a collective packaging unit, which may include written or otherwise user-accessible instructions detailing the sample collection, handling and/or processing methods of the invention.

Kits for practicing the assay methods of the invention include a suitable container or other device for collecting, storing, handling and/or processing a biological sample from expressed mammary fluid. A range of suitable collection devices is contemplated corresponding to a wide range of suitable biological samples that may be collected from the expressed mammary fluid. For example, simple sterile containers or reservoirs are provided to collect whole mammary fluid. Alternatively, a variety of solid phase devices, including microscopic glass slides, membranes, filters, beads and like media, are provided to receive or partition selected liquid or solid fractions of the mammary fluid, to receive or partition cells or cellular constituents from the mammary fluid, or to receive or partition purified or bulk proteins, glycoproteins, peptides, nucleotides (including DNA and RNA polynucleotides) or other like biochemical and molecular constituents from the mammary fluid. A wide variety of such sample collection devices are disclosed herein, or are otherwise widely known or described in the literature, which can be readily adapted for use within specific embodiments of the invention. These collection devices may be provided as a component of the breast pump (such as a removable nitrocellulose filter placed within the pump, optionally coupled there with by a permanent or removable support member, to directly receive or contact the expressed mammary fluid as it is pumped), or may be provided separately (for example as a non-integral membrane, filter, affinity column or blotting material to which mammary fluid or mammary fluid components are exposed to collect a biological sample for assay purposes). In more detailed aspects, the collection device includes a removable, fluid-retaining reservoir as described herein below.

In certain embodiments of the invention, kits include reagents and/or devices for detecting the presence and/or amount of a breast disease marker in the biological sample, for example an immunological or molecular probe that binds or reacts with a breast cancer marker. Among these possible reagents immunological and non-immunological probes for detecting the presence or amount of a breast cancer marker in the biological sample. The kits may also contain suitable buffers, preservatives such as protease inhibitors, direct or sandwich-type labels for labeling the probes, and/or developing reagents for detecting a signal from the label. In one aspect, kits of the present invention contain monoclonal antibodies useful for detecting and/or measuring a breast cancer marker in a sample. Such antibodies may be pre-labeled, or may be detected by binding to a secondary antibody optionally included in the kit. The antibody reagents may be provided in a separate container, or may be provided in combination in a series of containers. Within yet another aspect of the invention, kits contain sequence-specific oligonucleotide primers for detecting polynucleotide molecules encoding breast cancer marker proteins. Such primers may be provided in separate containers, or may be provided in combinations of one or more primer pairs in a series of containers. A broad selection of other kits are provided within the invention based on general knowledge in the art and on the description herein, including kits that contain specific instructions for carrying out the assays of the invention.

Also provided within the invention are methods for obtaining a biological sample from a patient and/or determining the amount of a breast disease marker in a biological sample from breast fluid, which methods employ a novel breast pump 10 or breast pump adapter 12, as described herein below. These methods include a step of applying the breast pump to induce breast fluid expression, wherein a solid phase sample collection medium is fluidly connected with the breast pump. The solid phase sample collection medium may be integrated within the breast pump or otherwise fluidly connected with the pump, so that an expressed breast fluid sample contacts the collection medium while the pump remains applied to the breast.

To practice these aspects of the invention, the breast pump 10 (FIG. 1) and breast pump adapter 12 (FIG. 12) each have fluidly connected therewith a solid phase sample collection medium selected from any of the solid phase media described herein above. The breast pump may be generally constructed according to various conventional breast pump designs, for example according to the general design described in U.S. Pat. Nos. 4,929,229 and 5,007,899 to Larsson; U.S. Pat. No. 5,601,531 to Silver; U.S. Pat. No. 3,786,801 to Sartorius; or U.S. Pat. No. 5,295,957 to Aida et al.

As with other conventional breast pumps, the breast pump 10 of the invention includes a breast engaging portion 14 constructed of a non-porous material. The engaging portion is sized and dimensioned to receive at least a nipple 16 portion of a breast 17 and form a suction seal therewith. Preferably, the breast engaging portion is sized and dimensioned to receive at least an areolar portion of the breast, and more preferably a distal quarter to one-half or larger portion of the breast (e.g., as shown in FIG. 1), and form a suction seal therewith. Different sizes and dimensions of the breast engaging member may be selected, e.g., to receive human breasts of differing sizes. Alternatively, devices for veterinary use are provided wherein the breast engaging member is sized and dimensioned to receive a breast of a non-human mammal.

To form a suction seal with the breast 17 as described above, the breast engaging portion 14 of the pump 10 may be constructed in a variety of shapes and dimensions. In one embodiment the engaging portion is formed as a simple cylinder, tube or funnel shaped and dimensioned to engage the nipple 16 or areolar portion of the breast in a suction seal. Preferably, a terminal edge 18 of the engaging portion is rounded or flared so that the edge does not impinge uncomfortably against the skin of breast 17 when negative pressure is applied to the breast to form the suction seal. In preferred embodiments the engaging portion is roughly funnel shaped to comfortably engage a distal quarter to one-half or larger portion of the breast, as shown in FIG. 1 and form a suction seal therewith.

The breast engaging portion 14 of the breast pump 10 can be constructed of any suitable non-porous material which is inert to body fluids and which has sufficient rigidity to prevent collapse of the engaging portion when negative pressure is applied against its inner walls 20. Preferably, the engaging portion and other parts of the breast pump are autoclavable for sterilization purposes. Thus, the engaging portion may be constructed of a rigid material such as a polypropylene, polyurethane, polyvinyl plastic, polymethyl methacrylate, and the like. Alternatively, the engaging portion may be constructed of a semi-rigid material which prevents collapse but allows for manual compression of at least a base 22 of the engaging portion to massage the nipple 16 and/or areolar region of the breast 17 to facilitate breast fluid expression. Suitable materials in this context include rubber or synthetic elastomers, e.g., silicon plastic (silastic) and like materials. Preferably, the material that forms the engaging portion is transparent to allow a physician or technician using the breast pump to visualize the breast 17 to determine its positioning and condition during application of the pump and to observe fluid expression from the nipple.

The breast engaging portion 14 of the breast pump 10 is fluidly connected to a sample collection housing 30 made of a rigid material (preferably transparent plastic). The solid phase sample collection medium, as described above, is supported in fluid connection with the breast engaging portion, for example by anchoring the solid medium to, or within, the breast engaging portion or sample collection housing. Typically, the solid phase sample collection medium is affixed within an interior compartment or lumen 58 of the sample collection housing or corresponding, fluidly connected, interior space of the breast engaging portion—using any of a wide range of optional anchoring or positioning means. Preferably, the solid phase medium is removably supported in fluid connection with the breast engaging portion, e.g., by means of a closeable retainer or replaceable cassette (see below).

Figure 4:
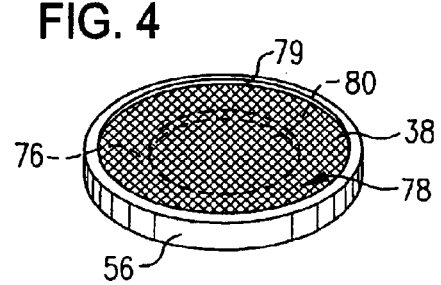
FIG. 4 is a perspective view of an alternative support member for supporting a solid phase sample collection medium in fluid connection with a breast pump.
Figure 5:
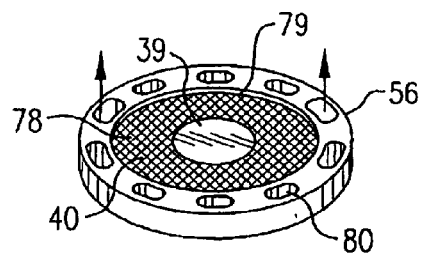
FIG. 5 is a perspective view of an alternative support member for supporting a solid phase sample collection medium in fluid connection with a breast pump.

In one aspect of the invention the sample collection housing 30 or breast engaging portion 14 supports a sample collection pad, or sheet, 38 of absorbent or adsorbent material, for example a membrane 39 or filter 40 pad or sheet (FIGS. 2-5). Multiple pads or sheets (of the same or different material) may be used in combination. For example, a membrane 39 (e.g., nitrocellulose) may be supported on a filter 40 (e.g., a paper filter) as shown in FIG. 5. In this manner, a first sheet may serve as a support member, a wetting member, a wicking member, or a partitioning member for a second sheet, or may introduce or remove a chemical reagent, probe, blocking agent, buffering agent, denaturing agent, etc. therefrom. In one aspect, the multiple sheet materials partition components of the breast fluid (e.g., by using different materials to retain different components of the breast fluid), thereby allowing for collection of different samples simultaneously.

In another aspect of the invention the housing 30 or breast engaging portion 14 supports a particulate solid phase sample collection medium 41, for example beads, resins, microspheres, particulate chromatographic media (e.g., agarose or silicate media), and the like (see, e.g., FIG. 9). In yet another aspect of the invention, the housing or breast engaging portion supports a non-particulate solid template for sample collection, for example one or more capillary tubes 42 (FIG. 6), coated tubes 43 (FIG. 10), plates, wells, slides and the like formed of glass, plastic or other suitable materials.

As shown in FIGS. 1 and 2, a preferred design of the breast pump 10 includes a removable coupling mechanism between the engaging portion 14 and the sample collection housing 30. A preferred coupling mechanism includes complementary threads 44, 46, disposed at mated connecting ends 48, 50 of the engaging portion, and housing, respectively. Alternatively, a simple pressure fit coupling may be provided to removably couple mated connecting ends 48, 50 of the engaging portion and housing, as shown in FIG. 9. In yet another alternative embodiment, the connecting ends 48, 50 are removably coupled by a hinge 52 and latch 54 that pivotally connects the two connecting ends (FIG. 10).

The sample collection housing 30 or breast engaging portion 14 can support the solid phase sample collection medium in several ways, as exemplified in the drawings and by a variety of equivalent designs and configurations that will be apparent to the artisan. In preferred embodiments of the invention, the solid phase medium is held on or within a support member 56 adapted to support the solid phase medium in fluid connection with the breast engaging portion, for example a support that is fixedly interposed between the engaging portion 14 and the sample collection housing.

Thus, in one exemplary design shown in FIGS. 1 and 2, the support member 56 is a removable disc spanning a lumen 58 of the housing and interposed between connecting ends 48, 50 of the engaging portion and housing. For use in conjunction with a variety of breast pump designs, a diameter 59 (FIG. 3) of the support member is between about ¼–3.0 inches, preferably about ½–2.0 inches, and more preferably about ¾–1 inches. In preferred aspects, the disc-shaped support member seats within a circumferential groove 60 in the connecting end 48 of the housing. A complementary circumferential groove 62 in the connecting end 46 of the engaging portion opposes the circumferential groove in the connecting end of the housing to sandwich the disc-shaped support member therebetween.

In this embodiment, prior to connecting the engaging portion 14 of the breast pump 30 with the housing 30, the support member is seated therebetween (e.g. by fitting the support member within the opposing circumferential grooves 60, 62 of the housing and engaging portion). The force of connection (i.e. threading, pivoting or pushing the engaging portion and housing relative to one another) firmly sandwiches the support member in position between the engaging portion and housing.

To facilitate this purpose, the thickness (i.e., sectional height) 63 of the support member 56 in the present embodiment is equal to or slightly greater than the height of a sidewall 64 of the circumferential groove 60 of the housing 30, whereby the support member is held in a friction fit and may be partially compressed when the engaging portion and housing are connected. Thus, the thickness of the support member is between about 2 mm to 5 cm, preferably about 3 mm to 2 cm, and more preferably about 4 mm to 1 cm. Consistent with this design, the support member can be made of a hard plastic material (e.g., a hard polyvinyl or polyurethane), but is preferably made of a resilient, moderately compressible material, e.g., soft plastic, rubber, or a waterproof fiber or composite material as used in conventional plumbing and automotive gaskets.

Figure 7:
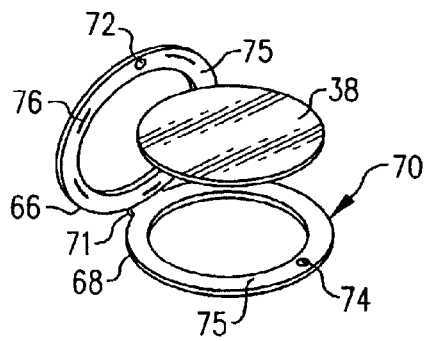
FIG. 7 is a perspective view of an alternative support member for supporting a solid phase sample collection medium in fluid connection with a breast pump.

A disc-shaped support member 56 is well suited to support a sheet 38 of absorbent or adsorbent material, such as a membrane or filter. As shown in FIGS. 2 and 7, the sheet is preferably sandwiched between an upper retainer ring 66 and a lower retainer ring 68 of the support member to hold the sheet in place against negative pressure that may pass through the filter when a vacuum is applied through the engaging portion 14 and housing 30 (see below), as well as when the nipple 16 impinges against the sheet. The upper and lower retainer rings may be integrally joined in a disposable refill as shown in FIG. 2, or the two retainer rings may be separable to provide a reusable cassette for removing and inserting replacement sheets. An example of the latter design is depicted in FIG. 7, where the upper and lower retainer rings are releasably interconnected, e.g., by a hinge 71 or other connecting means such as an interlocking threading or detent fit mechanism. In this embodiment the upper and lower rings can be opened or disconnected to allow insertion and removal of the sheet, and juxtaposingly closed, e.g., by a snap 72 on one ring adapted to form a detent fit within a receptacle 74 on the opposing ring, thereby holding the sheet in a fixed position between the two rings. To facilitate this purpose, opposing faces 75 of the upper and lower rings may have a rugose or otherwise decorated surface to facilitate retention of the sheet, for example a ridge 76 or ridges to engage the sheet and securely clamp the sheet between the two rings.

In an alternative design depicted in FIGS. 4 and 5, there is no upper retaining ring 72 and the sheet 38 simply rests upon the support member 56 or is removably retained against an upper surface 76 of the support member by alternative retaining means. For example, the sheet may be fitted within a recess 78 surrounding the upper surface of the support member that is shaped and dimensioned to receive the sheet. The sheet may be securely fitted within the recess, e.g., by appropriately sizing the sheet so an edge of the sheet frictionally engages a sidewall 79 of the recess. Alternatively, a retaining groove may be provided between the sidewall of the recess and the upper surface of the support member to receive the edge of the sheet and thereby retain the sheet by a detention fit within the recess during use. In yet another alternative design, the sheet simply rests atop the upper surface of the support member and is removably secured thereto, e.g., by wetting or gluing (preferably with an inert bonding agent) to create a temporary bond between the sheet and upper support member surface. In each of the foregoing designs, the sheet can be easily seated within or atop the housing for sample collection and removed thereafter for processing, e.g., by hand or using forceps or other conventional handling tools.

In preferred embodiments of the invention, the support member 56 includes a recess 78 which forms a fluid-retaining well, as shown in FIG. 5. The recess can thus be filled with a desired solution, such as a buffer, a solution containing a probe, cross-linking agent, blocking agent, denaturing agent, etc., to facilitate sample collection, handling, and/or processing.

Where the design of the support member 56 is such that it spans the lumen 58 of the sample collection housing 30 or corresponding interior compartment of the breast engaging member 14, or when the support member contains a recess 78 forming a well, it is generally desirable to provide air channels 80 in the support member 56 to allow negative vacuum pressure to pass from the housing through the air channels to the engaging portion 14 of the pump during operation, and to allow venting of the engaging portion and housing to permit disengagement of the engaging portion from the breast 17 after use. Preferably, one or more such air channels are located near the periphery of the support member, as shown in FIGS. 2, 3, 5, 6 and 9. Alternatively, one or more air channels may be centrally located, as shown in FIG. 4. The air channels may be positioned so that they do not communicate with the solid phase sample collection medium, as shown in FIGS. 2, 3, 5, 6 and 9, or they may communicate and form a gaseous connection therewith (provided that the solid phase medium is porous and has sufficient strength to withstand vacuum pressures transmitted through the air channel), as shown in FIG. 4.

Alternative designs and configurations of the housing 30, breast engaging member 14, and/or support member 56 are also provided which vary with the type of solid phase sample collection medium used. For example, when a particulate solid phase sample collection medium 41 (e.g. beads, resins, or microspheres) is used, the medium may be enclosed in a cartridge 82 removably mounted to, or integrated within, the support member or otherwise removably connected to the sample collection housing 30 or breast engaging portion. As shown in FIG. 9, preferred embodiments of the invention provide a removable engagement mechanism which allows the cartridge or other receptacle containing the solid phase medium to be removably engaged relative to the housing or breast engaging member, e.g., by engaging the cartridge with a support member so that a first end of the cartridge makes a fluid connection with the engaging portion 14 of the pump 10. In one embodiment, the first end of the cartridge is removably inserted through a mounting channel 86 which passes through the support member to provide a fluid connection between the engaging portion of the pump and the cartridge first end. Preferably, the channel is dimensioned to receive the first end of the cartridge in a friction fit (e.g., wherein a diameter of the channel is about 0.5 mm to 2 cm, preferably about 1 mm to 1 cm, and more preferably about 3–5 mm), whereby the cartridge can simply be pushed into the channel until the cartridge first end is flush with, or extends slightly above, the upper surface 76 of the support member and will remain in place during use. For this purpose it is also preferable to form at least the channel portion of the support member from a resilient, moderately compressible material so that the channel yieldingly receives and releases the cartridge in a moderate (i.e., readily hand removed) friction fit. Alternatively, the cartridge can be engaged relative to the housing by complementary threading or interlocking detent fitting (e.g., a conventional key and groove design) between the cartridge first end and the support member channel). In yet other alternative designs the cartridge can be permanently engaged with the support member or engaged directly to the housing.

Design and construction of the cartridge 82 will vary depending on the characteristics of the particulate solid phase medium used, including the size of the particles, the function of the particles (e.g., chromatography adsorption, affinity binding, etc.), and whether the particles are used dry or are contained in a solution, among other factors. Design and construction of the cartridge will further depend on the type of breast disease marker(s) which may be sought for detection in the sample (e.g., cells, proteins, lipids or nucleic acids).

In a preferred embodiment shown in FIG. 9, the cartridge is cylindrical and contains beads or microspheres. To enclose the beads or microspheres in the cylinder while maintaining a fluid connection with the engaging portion 14 of the pump 10, the first end 84 of the cylinder is covered by a semi-permeable cover 90 of a porous barrier material (e.g., a filter or membrane) which allows breast fluid (including or excluding selected components of the fluid, such as cells) to pass through the cover to contact the beads or microspheres, while preventing escape of the beads or microspheres from the cartridge. In this manner, the cover can partition components of the breast fluid into the cartridge, and can also separately retain different components on the cover, thereby allowing for collection of different samples simultaneously. The semi-permeable cover can be affixed to the cartridge by a variety of means, e.g., by bonding with a removable or permanent bonding agent, or by providing a removable or integral cover retaining ring 92 to secure the cover to the cartridge first end 84. A second end of the cartridge features a second end cover 96 which may be integral to or removable from the cartridge, and which may be impermeable to gas and fluids or semi-permeable as described above for the first end cover.

In another aspect of the invention, the housing 30 supports a non-particulate solid template for sample collection. This type of solid phase collection medium includes, e.g., one or more capillary tubes 42 (FIG. 6), coated tubes 43 (FIG. 10), plates, wells, slides and the like. These templates for receiving, adsorbing or binding a sample of breast fluid (or desired components thereof) are preferably formed of glass, plastic or like materials known in the art to be suitable for sample collection (e.g., inert plastics).

Figure 6:
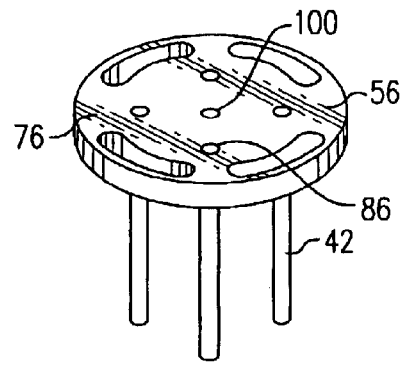
FIG. 6 is a perspective view of an alternative support member for supporting a solid phase sample collection medium in fluid connection with a breast pump.

To accommodate these various templates, yet additional alternative designs and configurations of the housing 30, breast engaging portion 14, and/or support member 56 are provided. For example, when capillary tubes 42 are used, these may be mounted to or integrated within the support member, or anchored by a variety of other comparable means with respect to the housing 30. As shown in FIG. 6, preferred embodiments of the invention utilize a support member with one or more mounting channels 86 to removably receive a first end of one or more capillary tubes 42, so that the end of the tube makes a fluid connection with the engaging portion 14 of the pump 10. Thus, the channels have a preferred diameter equal to or slightly less than a diameter of a standard capillary tube, i.e., about 0.5 mm to 3 mm, preferably about 1–2 mm and more preferably about 1.5 mm. Construction of the support member and mounting of the tube(s) is similar to support member construction and mounting of the cartridge as described above. When a single tube is used, it is preferably placed centrally relative to the housing. When multiple tubes are used they may be arrayed to collect multiple samples simultaneously, e.g., as shown in FIG. 6.

Another alternative solid template for sample collection provided within the invention is a coated tube 43 which is preferably mounted relative to the housing 30 in the same manner as described above for capillary tubes 42 (FIG. 10). The tube may be open at both ends, or may have a semi-permeable cover at one or both ends, as well as an impermeable second end cover, as described above for the cartridge 82.

The coated tube has a lumenal coating 100 adapted for adsorbing, binding, partitioning or otherwise processing the breast fluid sample. For example, the coating may be an affinity coating having an antibody, ligand, or other binding partner that specifically binds a selected breast disease marker, wherein the coating is covalently or otherwise bound to a lumenal wall of the tube. A wide variety of useful coatings are disclosed herein or are otherwise well known in the art. These coatings may also be used to coat other solid phase media for use within the invention, including templates such as wells, plates, slides, etc, including a well formed by a recess 78 in a support member 56.

Because only small droplets of breast fluid will typically be expressed at the surface of the nipple 16, it is generally preferred to directly contact the expressed fluid on the nipple with the solid phase sample collection medium. This requires positioning of the sample collection medium close to the base 22 of the breast engaging portion 14 of the pump as shown in the figures. Thus, when a support member 56 is provided it is positioned so that its upper surface 76 will directly contact the nipple during application of negative pressure through the engaging portion to the breast. Only approximate positioning is generally required in this regard, because the nipple will tend to be drawn toward the support member by the vacuum and thereby will abut the upper support member surface.

However, because breast pump designs and breast anatomy vary significantly, it is preferable to adjustably mount the solid phase medium relative to the housing 30 so that it can be moved closer to, or farther away from, the base 22 of the engaging portion 14 of the pump 10. Thus, in preferred embodiments of the invention a reciprocating mechanism is provided which adjustably moves the solid phase collection medium in closer, or more distant, proximity to the nipple when the breast pump is engaged therewith. At the beginning of the fluid expression procedure, the collection medium is retracted away from the nipple while negative pressure is applied to the breast to facilitate fluid expression. Fluid expression is visualized through a transparent engaging portion or housing, and the collection medium is then advanced proximal to the nipple to contact the expressed fluid.

As shown in FIG. 11, a preferred design for the reciprocating mechanism incorporates a support member 56 to support the solid phase collection medium, as described above. The support member is reciprocatingly mounted relative to a rotating member 109 of the housing 30, preferably on a reciprocating carrier 110. The support member may be removably mounted to the carrier, e.g., by friction fitting, detention fitting or threadedly engaging the support member to a first end 112 of the carrier, as described above for mounting the support member to the housing and/or engaging portion 14 of the pump 10. For example, the support member may be mounted by friction fitting within a circumferential groove 114 at the first end of the carrier. In conjunction with this design, the carrier is preferably in the form of an open cylinder so that negative pressure can be effectively transmitted through the carrier and support member to the engaging portion.

To reciprocatingly adjust the position of the carrier 110 and/or support member 56 relative to the engaging portion 14 of the pump 10, the rotating member 109 of the housing 30 is sealably, rotatably, and removably interconnected to the base 22 of the engaging portion. This interconnection may be accomplished by a variety of designs, one of which is to seat a first O-ring 116 in opposing circumferential grooves 118, 120 in the connecting ends 48, 50 of the engaging portion, and the rotating member of the housing, respectively. These grooves are sized and dimensioned to receive the O-ring in an airtight seal when vacuum pressure is applied through the housing and engaging portion of the pump, without substantially compressing the O-ring. The O-ring is also lubricated, e.g., with silicon grease. These features allow free rotation of the rotating member of the housing relative to the engaging portion of the pump, which rotation drives the reciprocating mechanism to advance the sample collection medium (e.g., by advancing the carrier and/or support member) to contact the expressed breast fluid on the nipple 16.

To complete the reciprocating mechanism for the above described embodiment of the invention, the rotating member 109 of the housing 30 is also sealably and rotatably interconnected to a stationary member 124 of the housing. This interconnection is preferably achieved by seating a second O-ring 126 in opposing circumferential grooves 128, 130 in a rear connecting end 132 of the rotating member of the housing and a front connecting end 134 of the stationary member 124 of the housing, respectively. These grooves are also sized and dimensioned to receive the O-ring in an airtight seal without substantially compressing the O-ring, and the O-ring is lubricated to facilitate free rotation of the rotating member relative to the stationary member.

To reciprocate the carrier 110 and/or support member 56 forward and backward relative to the engaging portion 14, the rotating member 109 of the housing 30 is provided with a lumenal, helically oriented groove 140 dimensioned to receive a riding peg 142 extending transversely from the carrier or support member. In addition, the rotating member of the housing is provided with a longitudinally oriented, lumenal groove 144 dimensioned to receive an angularly fixating keel 146 extending transversely from the carrier or support member. In accordance with this design, rotation of the rotating member 109 of the housing 30 drives rotation of the carrier or support member which is angularly fixed relative to the rotating member by the fixating keel engaged with the longitudinal groove of the rotating member. As the rotating member of the housing and carrier thus rotate (with the position of the engaging portion and stationary member of the housing angularly fixed by friction or manual or structural resistance), the riding peg rides along the helical groove, translating the peg in the direction of the groove and thereby causing the support member or carrier to reciprocate forward or backward relative to the engaging portion.

To insert and remove the solid phase medium and/or support member 56 from the rotating member 109 of the housing 30, a removable interconnection is provided between the rotating member and the base 22 of the engaging portion, as described above. To uncouple the rotating member and engaging portion, all that is required is that these parts be pulled in opposing directions, whereby the O-ring 116 will unseat from one of the opposing circumferential grooves 118, 120 in the connecting ends 48, 50 of the engaging portion and rotating member, respectively. To recouple the rotating member and engaging portion after loading or retrieval of the sample collection medium and/or support member, they are simply pushed back together. To facilitate reseating of the O-ring, it may be desired to make one of the opposing circumferential grooves deeper than the other, so that the deeper groove retains the O-ring when the rotating member and engaging portion are separated, and the shallower groove more readily accepts the O-ring when they are re-coupled.

Figure 15:
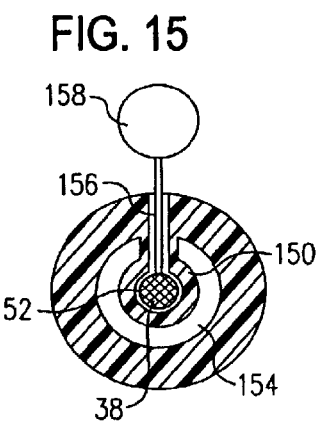
FIGS. 14 and 15 provide partial sectional views of a breast pump employing a sliding reciprocating mechanism to adjust positioning of a solid phase sample collection medium within the pump.
Figure 14:
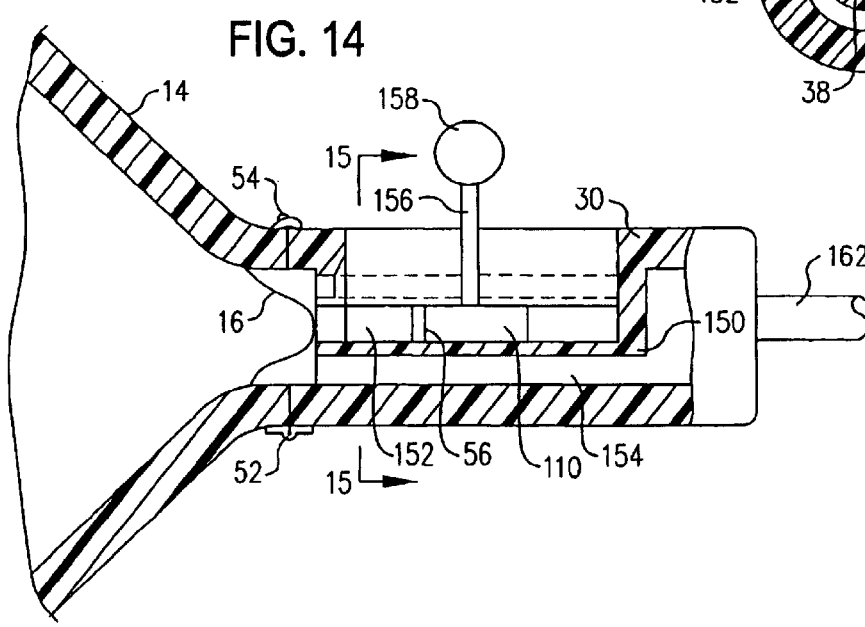

An alternative reciprocating mechanism is provided within the invention which uses a simple slide mechanism to reciprocate the sample collection medium relative to the engaging portion 14 of the pump 10, as shown in FIGS. 14 and 15. One embodiment of the slide mechanism features a manifold 150 defining an inner lumen 152 which is not in gaseous connection with an outer lumen 154 of the housing. This design provides for a manual slide lever 156 to extend to the outside of the housing so that a head portion 158 of the lever can be manually engaged by a pump operator. The slide lever is in turn connected to the support member 56 or carrier 110 which are sized and dimensioned to allow the carrier to reciprocate freely within the inner lumen.

In operation, the slide lever 156 is moved to a rearward position so that the solid phase sample collection medium (e.g., a pad or sheet 38 of absorbent material) is out of contact with the nipple 16, as shown in FIG. 14. Negative pressure is applied through the outer lumen 154 to the area of the breast surrounding the nipple, the tip of which is aligned with the inner lumen. Breast fluid expression is visualized through the transparent engaging portion and housing, at which time the lever is manually engaged by the head portion 158 and moved forward. Movement of the lever causes the support member and/or carrier to move forward until the sample collection medium contacts the expressed fluid at the tip of the nipple. The engaging portion and housing are removably connected, e.g., by a hinge 52 and latch 54 or other suitable connection means, thereby allowing for easy insertion and removal of the solid phase medium and/or support member.

Figure 8:
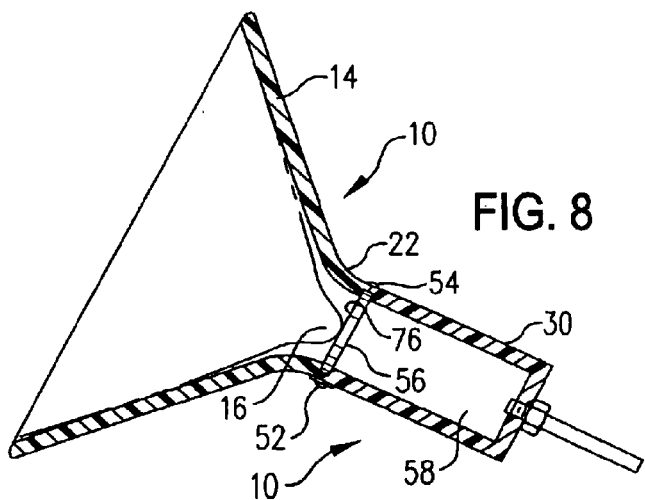
FIG. 8 is a partial sectional view of a breast pump device employing the concepts of the invention.

In each of the foregoing breast pump designs, the engaging portion 14 of the breast pump 10 is in gaseous connection with a vacuum pump 160 capable of generating sustained negative pressure in an area of the breast 17 surrounding the nipple 16 (see FIG. 1). Any of a large variety of vacuum pumps, which are well known for use in conjunction with breast pumps, can be used, including manual pumps (FIG. 1), mechanically driven pumps and electrically driven pumps. When activated, the pump generates negative pressures of between about 50–200 mm Hg. Typically the pump will be connected via a heavy vacuum hose 162 in connection with the engaging portion. Generally, the hose is connected to the housing 30 which will is in gaseous connection with the engaging portion (see, e.g., FIGS. 1, 8 and 11).

Pressure exerted upon the breast 17 by the pump can be varied in accordance with well known pressure modulating mechanisms (e.g., by providing a diaphragm or other mechanism to modulate a diameter of an in line, pressure modulating valve). In addition, the breast pump 10 includes a venting mechanism, e.g., a pressure release valve 164, which the user can selectively operate to close and vent the system before and after use, thereby selectively applying and releasing the vacuum pressure acting on the breast. In this regard, the system is generally vented as soon as sufficient breast fluid expression is observed by the operator. This also relieves pressure on seals (e.g., O-rings 116, 126), when the reciprocating mechanism relies on a sealable and rotatable connection between different parts of the pump (as in FIGS. 11 and 13), thereby facilitating respective rotation of the different parts to reciprocate the support member 56 and/or carrier 110.

Figure 13:
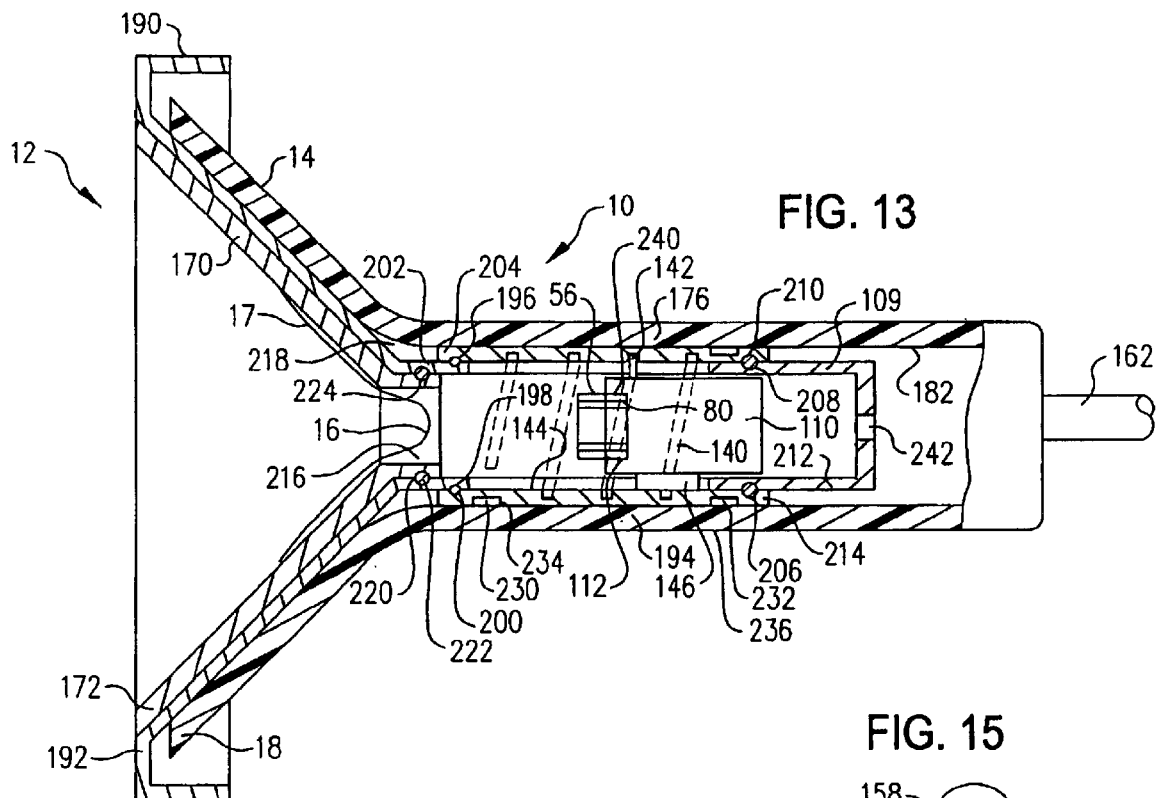
FIG. 13 is a sectional view depicting a breast pump adapter employing a reciprocating mechanism to adjust positioning of a solid phase sample collection medium within the adapter.

In yet another aspect of the invention, a breast pump adapter 12 is provided which couples a solid phase sample collection medium with a conventional breast pump (See FIGS. 12 and 13). As shown in FIG. 12, the adapter features a replacement breast engaging portion 170 sized and dimensioned for removable insertion within a breast engaging portion 14 of a conventional breast pump. In preferred embodiments, the replacement breast engaging portion is funnel shaped and nests within a funnel shaped breast engaging portion of an existing breast pump. When fully nested, a terminal edge 172 of the replacement breast engaging portion extends at least as far as the terminal edge 18 of the breast engaging portion of the existing breast pump.

The replacement breast engaging portion 170 can be removably connected to the breast engaging portion 14 of the existing breast pump 10 by a variety of means, e.g., by friction fitting, detention fitting or threadedly engaging the replacement engaging portion with the breast engaging portion of the existing pump. Preferably, the adapter 12 has a stem portion 174 that extends into a cylindrical, connecting portion 176 of the existing pump, and the stem portion cooperates with this part of the existing pump to provide a removable connection mechanism. Thus, in one preferred embodiment the stem portion features a circumferential groove 178 dimensioned to receive an O-ring 180, which O-ring impinges against an inner wall 182 of the connecting portion to create a friction fit to interconnect the replacement engaging portion with the breast engaging portion of the existing pump.

The adapter 12 supports a solid phase sample collection medium in fluid connection with the replacement engaging portion 170. Preferably, the solid phase medium is connected with the replacement engaging portion by a support member 56, as described above. The support member may be integrally or removably mounted to the adapter, e.g., by friction fitting, detention fitting or threadedly engaging the support member to the stem 174 of the replacement engaging portion, in a position that will allow contact between the nipple and solid phase medium during or after breast fluid expression. For example, the support member may be mounted by friction fitting within a circumferential groove 184 at a base of the stem (FIG. 12).

In preferred embodiments of the breast pump adapter 12, a reciprocating mechanism is provided to move the solid phase sample collection medium relative to the replacement engaging portion 172, in accordance with the concepts described above. As shown in FIG. 13, a preferred design for the adapter having a reciprocating mechanism features a replacement breast engaging portion 170 sealably and rotatably nested within a rotating dial member 190, which is in turn sized and dimensioned for removable insertion within a breast engaging portion 14 of an existing breast pump. The replacement breast engaging portion and rotating dial member are preferably funnel shaped to collectively nest within a funnel shaped breast engaging portion of a conventional breast pump. When fully nested, a terminal edge 172 of the replacement breast engaging portion and free edge 192 of the rotating dial member extend at least as far as the terminal edge 18 of the breast engaging portion of the existing breast pump.

The rotating dial member 172 is connected to a rotating member 109 of the housing 30, preferably as a unitary insert, whereby manual rotation of the dial member drives rotation of the rotating member of the housing. The rotating member of the housing is in turn rotatably coupled with an anchoring member 194 of the housing which anchors the entire housing within the existing pump, e.g., within a cylindrical, connecting portion 176 of the existing pump. As shown in FIG. 13, the anchoring member of the housing is preferably in the form of a sleeve which partially surrounds the rotating member of the housing and is sealably, rotatably connected therewith. The anchoring member is in turn non-rotatingly anchored within the cylindrical, connecting portion of the existing pump.

In one preferred embodiment the rotating member 109 of the housing is sealably, rotatably connected with the anchoring member 194 of the housing by seating a first O-ring 196 in opposing circumferential grooves 198, 200 at front connecting ends 202, 204 of the rotating member and the anchoring member 194 of the housing, respectively. These grooves are sized and dimensioned to receive the O-ring in an airtight seal between the rotating member and anchoring member, without substantially compressing the O-ring. The O-ring is also lubricated to facilitate free rotation of the rotating member relative to the anchoring member. A second, lubricated and non-compressingly seated O-ring 206 is seated in opposing circumferential grooves 208, 210 at rear connecting ends 212, 214 of the rotating member and anchoring member of the housing, respectively, to facilitate rotation of the rotating member relative to the anchoring member.

To align and facilitate rotation of the rotating member 109 of the housing, the rotating dial member 190 (which drives the rotating member of the housing) is sealably, rotatably connected with the replacement engaging portion 170 of the adapter 12. Preferably, the replacement engaging portion has a stem 216 which nests within a stem-shaped base 218 of the rotating dial member. Free rotation between these structures is achieved, e.g., by providing a third lubricated and non-compressingly seated O-ring 220 seated in opposing circumferential grooves 222, 224 in the stem and base of the replacement engaging portion and rotating dial member, respectively. This rotation is also facilitated by friction contact (by pressure and/or suction) between the replacement engaging portion and the breast 17 of the patient, which angularly secures the replacement engaging portion and prevents its co-rotation with the rotating dial member.

The anchoring member 194 of the housing is in turn anchored within the existing pump by an anchoring mechanism that angularly secures the anchoring member within the pump, e.g., against an inner wall 182 of the cylindrical connecting portion 176. For example, front and rear compressible anchoring sleeves 230, 232 may be mounted in front and rear circumferential anchoring sleeve retainer grooves 234, 236 surrounding the anchoring member. The anchoring sleeves are non-lubricated and are made of a semi-compressible material such as rubber or soft plastic. This construction creates a friction anchor between the anchoring member and the inner wall of the connecting portion, so that the anchoring member does not move angularly during rotation of the rotating member 109 of the housing. Both the anchoring sleeves and retainer grooves are preferably sharply angled at a position corresponding to the bases of the retainer grooves (i.e., they have a rectangular or triangular cross-section), to securely retain the anchoring sleeves in the grooves despite strong friction against the inner wall of the connecting portion when the anchoring member of the housing is being inserted into the connecting portion of the existing breast pump 10 to assemble the adapter 12 with the pump.

Because the replacement engaging portion 170 is anchored by friction against the breast 17, and the anchoring member 194 of the housing 30 is anchored by friction against the inner wall 182 of the connecting portion 176 of the existing pump 10, the rotating member 109 of the housing rotates freely with respect to both the replacement engaging portion and the anchoring member when an operator manually engages the rotating dial member 190 and turns it gently while maintaining pressure against the breast.

Relative rotation between the rotating member and anchoring member of the housing drives the reciprocating mechanism within the instant embodiment of the invention to advance the sample collection medium (e.g., by advancing a carrier 110 and/or support member 56 supporting the medium) toward the replacement engaging portion 170 to contact the expressed breast fluid on the nipple 16. As with previously described embodiments, the housing 30 preferably houses a support member 56 to support the solid phase collection medium, as described above. The support member is reciprocatingly mounted relative to the anchoring member 194 of the housing 30, preferably on a reciprocating carrier 110. The support member may be removably mounted to the carrier, e.g., by friction fitting, detention fitting or threadedly engaging the support member to a first end 112 of the carrier, as described above. In the embodiment shown in FIG. 13, the support member is removably engaged with the carrier by cooperative threading 140 between the support member and carrier. In addition, the support member may be sized and dimensioned for receipt within the stem 216 of the replacement engaging portion, because the replacement engaging portion and an inner (i.e., lumenal) diameter of the stem thereof are smaller than respective dimensions of the original engaging portion 14 and its base 22, so that the nipple may not fully extend through the stem to contact the collection medium within the housing. Also in conjunction with this design, the carrier is preferably in the form of an open cylinder and the rotating member 109 of the housing has a vacuum port 242 so that negative pressure can be effectively transmitted through the rotating member and carrier (and/or through air channels 80 of the support member) to the replacement engaging portion.

To reciprocatingly adjust the position of the carrier 110 and/or support member 56 relative to the replacement engaging portion 170 of the adapter 12, the anchoring member 194 of the housing is provided with a lumenal, helically oriented groove 140 dimensioned to receive a riding peg 142 extending transversely from the carrier or support member. In addition, the rotating member of the housing is provided with a longitudinally oriented, lumenal groove 144 dimensioned to receive an angularly fixating keel 146 extending transversely from the carrier or support member. Lastly, the rotating member is provided with a second, longitudinally oriented, lumenal groove 244 to allow access of the riding peg through the wall of the rotating member of the housing into the helically oriented groove and to allow reciprocating passage of the pin along the groove.

In accordance with this design, rotation of the rotating dial member 190 drives rotation of both the rotating member 109 of the housing 30 as well as the carrier 110 (or support member) which is angularly fixed relative to the rotating member by the fixating keel 146 engaged with the longitudinal groove 144 of the rotating member. As the rotating member and carrier thus rotate (with the position of the replacement engaging portion 170 and anchoring member 194 angularly fixed by friction or manual or structural resistance), the riding peg rides along the helical groove 140, translating the peg in the direction of the groove and thereby causing the support member or carrier to reciprocate forward or backward relative to the replacement engaging portion.

To insert and remove the solid phase medium and/or support member 56 from the adapter 12, removable connections can be uncoupled between the existing pump 10 and the entire adapter unit, between the rotating member 190 and anchoring member 194 of the housing, or between the rotating dial member and replacement engaging portion 170, among other access designs which will be readily apparent to those skilled in the art.

In more detailed aspects of the invention illustrated in FIGS. 16-26, selected features of a general purpose breast pump 10 for mammary fluid sample collection as described above are incorporated within a hand-held breast pump device 10'—adapted for greater fidelity and ease of sample collection. The hand-held sample collection pump is uniquely designed and constructed to incorporate the breast engaging member 14 and the vacuum pump mechanism 160 in a compact, structurally integrated breast fluid collection apparatus that can be manipulated and operated with one hand. As with the general-purpose breast pump 10, described above, the hand-held pump 10' incorporates the vacuum pump mechanism 160 in gaseous connection with the breast engaging element 14 to route suction pressure from the pump mechanism, through the engaging element, to apply negative pressure in the area of the nipple 16 of the patient. The solid phase sample collection medium (e.g., a membrane, filter, particulate medium, and/or a non-particulate solid collection template such as a plastic or glass tube, well, vial or slide) is likewise fluidly connected with the breast engaging member—to provide for direct or indirect transmission of the expressed breast fluid through the engaging member to contact the solid phase collection medium.

According to these aspects of the invention, novel breast fluid sample collection methods are provided wherein a doctor, technician or patient collecting a breast fluid specimen can grasp and operate the hand-held breast pump 10' to stimulate expression of the breast fluid and collect a specimen thereof while keeping one hand free for additional tasks, such as monitoring the patient and recording patient information. In this regard, the compact pump design allows the device to be picked up and manipulated with one hand—to seat the breast engaging element against the breast of the patient and thereafter apply vacuum pressure to the breast by manual operation of the vacuum pump 160 to stimulate expression of breast fluid. This action causes a suitable volume of breast fluid to be expressed at or near the nipple 16 for sample collection. In conjunction with these simple operation steps, the hand-held device also allows for simultaneous collection of the expressed breast fluid onto, or within, the solid phase sample collection medium that is fluidly connected with the engaging member, often without additional manual steps or a need to remove the device from the breast or otherwise engage two hands in the operation.

The hand-held breast pump device 10' can be employed for collection of breast fluid following oxytocin stimulation to facilitate breast fluid expression, as described above. Alternatively, the device can be used without oxytocin priming to achieve breast fluid expression by vacuum pressure alone, optionally coupled with mechanical breast stimulation, in a substantial percentage of subjects.

In using the hand-held breast pump 10' of the invention expressed breast fluid is typically transferred directly upon expression to the solid phase sample collection medium, without intervening manual steps or a requirement to remove the breast engaging member 14 from the breast 17 before the sample is collected. Sample collection in this manner is rapid and simple, and promotes sanitary application of the device to minimize the risk of patient infection and sample contamination. Thus, within certain methods of use for the hand-held breast pump, breast fluid is directly transferred to a solid phase collection medium, for example a membrane, filter, reservoir or vial, integrated within the hand-held pump. The sample may be collected as whole, undiluted breast fluid containing constituent proteins, particulates and/or cells. Alternatively, selected components of the expressed breast fluid may be simultaneously or subsequently removed from the fluid (e.g., by filtering, partitioning, or refining the breast fluid) to yield a processed fluid sample and/or to obtain a solid phase constituent sample. For example, various collection methods are provided which yield separated solid components (e.g., cells or other particulates) from the fluid. Alternate collection methods yield soluble, suspended, or solid phase captured proteins, lipids, carbohydrates, polynucleotides or other molecular/biochemical components from the expressed breast fluid. In certain embodiments, the hand-held pump device functions to separate or partition a desired protein, lipid, carbohydrate, or polynucleotide sample material into a solid phase collection medium, such as a membrane, filter, or chromatographic substrate (e.g., leptin-, antibody-, enzyme-, or ligand-coated vials, beads, etc.) In this regard, various alternative or additional steps from known collection/chromatographic methods can be employed during sample collection and processing according to the invention. In this manner, proteins, lipids, carbohydrates, polynucleotides, cells, and non-cellular particulates may be partitioned from liquid components of the breast fluid, or separated from one another, simultaneous with or subsequent to expression of the fluid, by various known methods, including membrane adsorption, filtering, affinity chromatography, chemical processing, centrifugation, etc. to yield a range of constituent or processed samples.

In certain collection methods of the invention, breast fluid expressed by use of the hand-held pump 10' is simultaneously or subsequently diluted, filtered, washed, admixed with fixative or other processing agents, or otherwise processed or modified to yield a collected fluid sample partially or completely devoid of cells, proteins and/or other selected components originally present in the expressed fluid, to provide a processed fluid sample for laboratory analysis. In other embodiments, particulate components of the breast fluid, for example, cells, cellular components and/or cellular debris, are collected after processing and/or modification, e.g., for cytological examination. These and other alternative collection methods involving preliminary sample processing in conjunction with use of the hand-held breast pump 10' are optionally performed simultaneously with, or closely following expression of the breast fluid. Often, sample collection is coincident with the fluid contacting one or more solid phase collection medium(a) fluidly connected with the breast engaging member 14. Depending on the type(s) of medium(a) used, preliminary sample processing can also be achieved directly by simple operation of the pump, without the need for additional processing steps or removal of the breast engaging member 14 from the subject's breast. For example, the expressed breast fluid may be sequentially transferred through multiple media, e.g., through a filter or membrane into a liquid-retaining reservoir or container, thereby separating certain components for further processing or analysis. Alternatively, the expressed fluid may be partially processed coincident with transfer to the solid phase medium(a) by chemical or physical reaction (e.g., adsorption, covalent or affinity linkage, enzymatic reaction, etc.) with the medium or a coating or secondary processing agent admixed or linked therewith.

In yet other alternative methods within the invention, preliminary sample processing involves additional steps following breast fluid expression. In certain embodiments, the breast engaging member 14 is removed from the breast after the breast fluid is expressed and the fluid is transferred to a first solid phase sample collection medium, typically a membrane or filter. This initial or primary stage of sample collection may be followed by washing or by manual transfer of selected breast fluid components (e.g., proteins, carbohydrates, cells, or cellular debris) from the first solid phase collection medium (e.g., a nitrocellulose membrane 39) to a second solid phase medium, e.g., a glass slide or fluid-containing reservoir. Typically, preliminary sample processing in this regard precedes final packaging of the collected sample for storage or shipment to a lab for further processing and analysis of the sample.

In more detailed embodiments of the invention, cells or other cellular materials useful for cytological examination are separated or partitioned simultaneous with or sequential to breast fluid expression onto or within a first solid phase collection medium. In one example, whole cells are separated from the expressed fluid onto a nitrocellulose membrane 39 or a filter 40, which is typically secured in fluid connection with the breast engaging member 14 by a fixed or removable support member 56 mounted to the engaging member or sample collection housing 30 or otherwise integrated with the hand-held breast pump 10'. The cells are subsequently transferred or washed in fluid (e.g., cytology fluid) to a second solid phase sample collection medium (e.g., a slide, well, tube or vial), which may also be connected to, or integrated with, the breast engaging member or sample collection housing as described.

Figure 16:
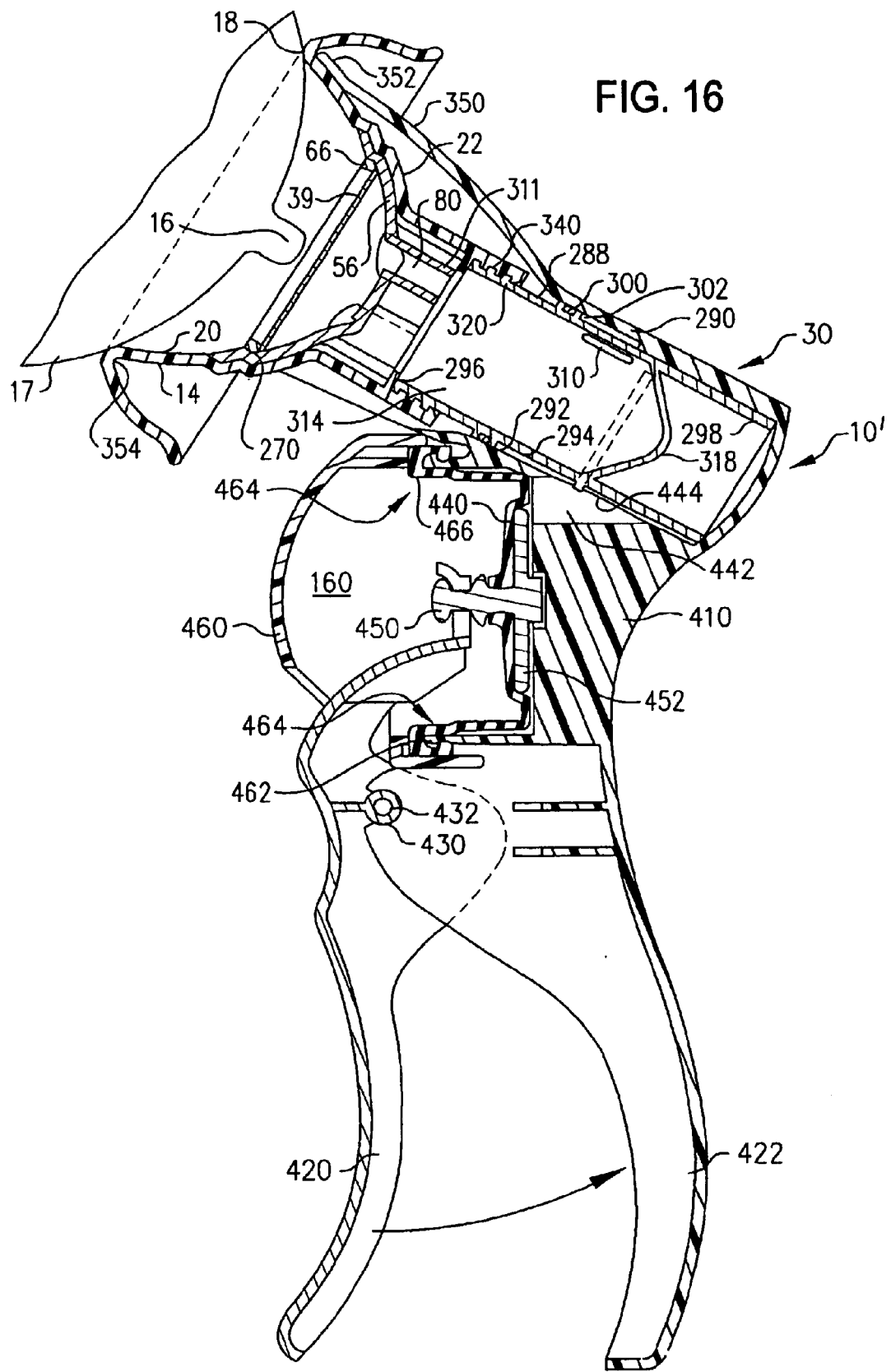
FIG. 16 is a sectional view illustrating a hand-held breast pump of the invention.

To facilitate sample collection according to the foregoing embodiments of the invention, the hand-held breast pump 10' is typically provided as a compact, handheld unit for ease of use and convenience of storage. As depicted in FIG. 16, certain embodiments of the hand-held pump comprise a modular device formed of a plurality of components that are joined or securable in fixed structural interconnection with one another. These components, which include a breast engaging member 14, vacuum pump 160 and solid phase sample collection component(s), may be partially or completely disassembled to remove or uncouple the individual components, or parts thereof, as desired for efficient operation, cleaning, servicing and/or storage.

As described above for the general-purpose breast pump 10 of the invention, the breast engaging portion 14 of the hand-held pump 10' is constructed of a rigid or semi-rigid, non-porous material and is sized and dimensioned to receive at least the nipple 16 of the subject's breast 17 and form a suction seal therewith (see, e.g., FIG. 16). The breast engaging portion may be constructed in a variety of shapes and dimensions to accommodate variations in breast anatomy. As also described above, the terminal edge 18 of the engaging portion is rounded or flared so that the edge impinges comfortably and forms an effective suction seal against the skin when negative pressure is applied to the breast. Typically, the engaging member is constructed of a rigid plastic material which is transparent to allow the operator to visualize the breast, determine positioning of the device, and observe expression of fluid from the nipple 16. Preferably, the engaging portion and other reusable components of the pump are autoclavable for sterilization purposes.

Figure 17:
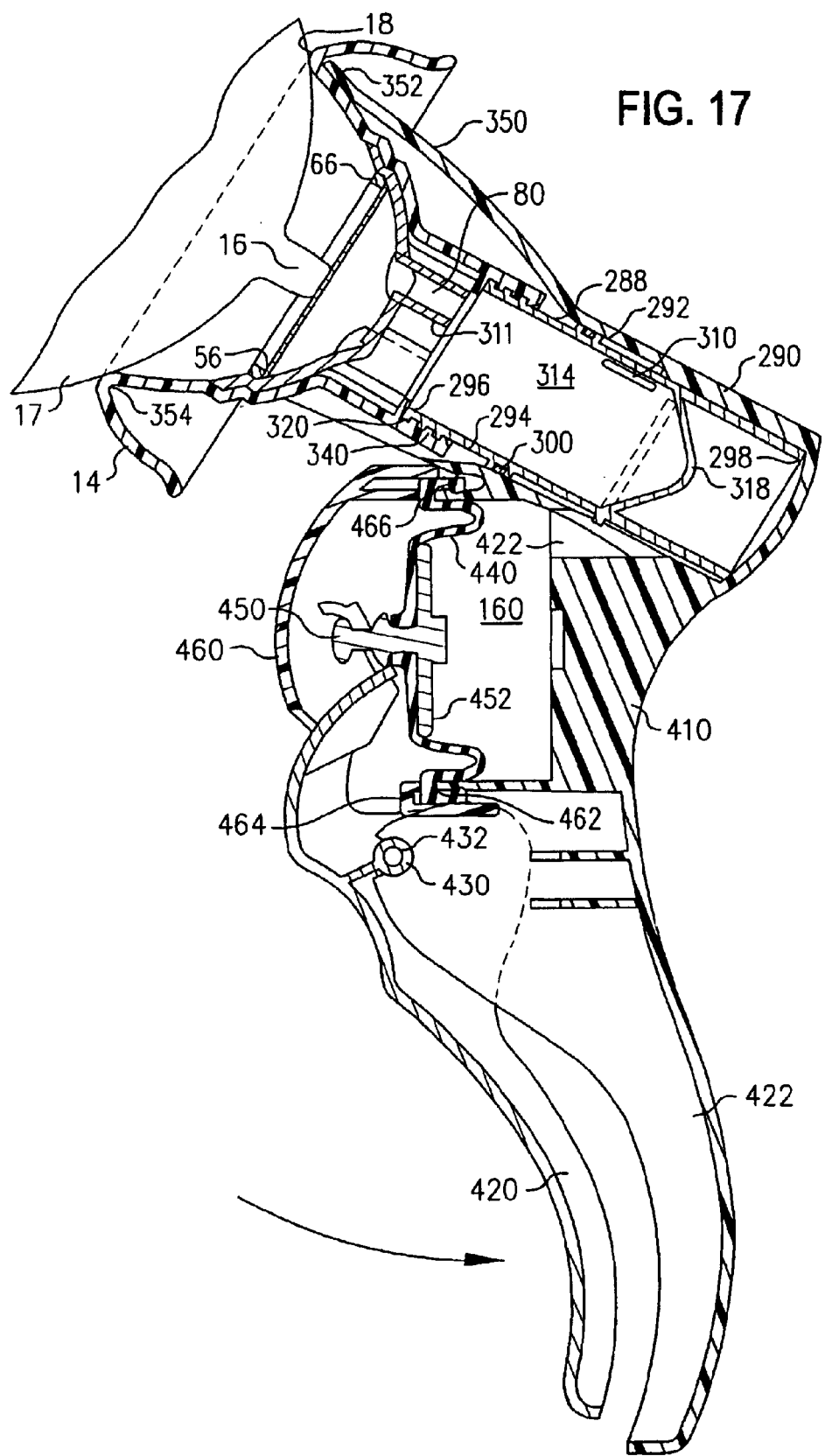
FIG. 17 is a sectional view illustrating a hand-held breast pump of the invention.
Figure 18:
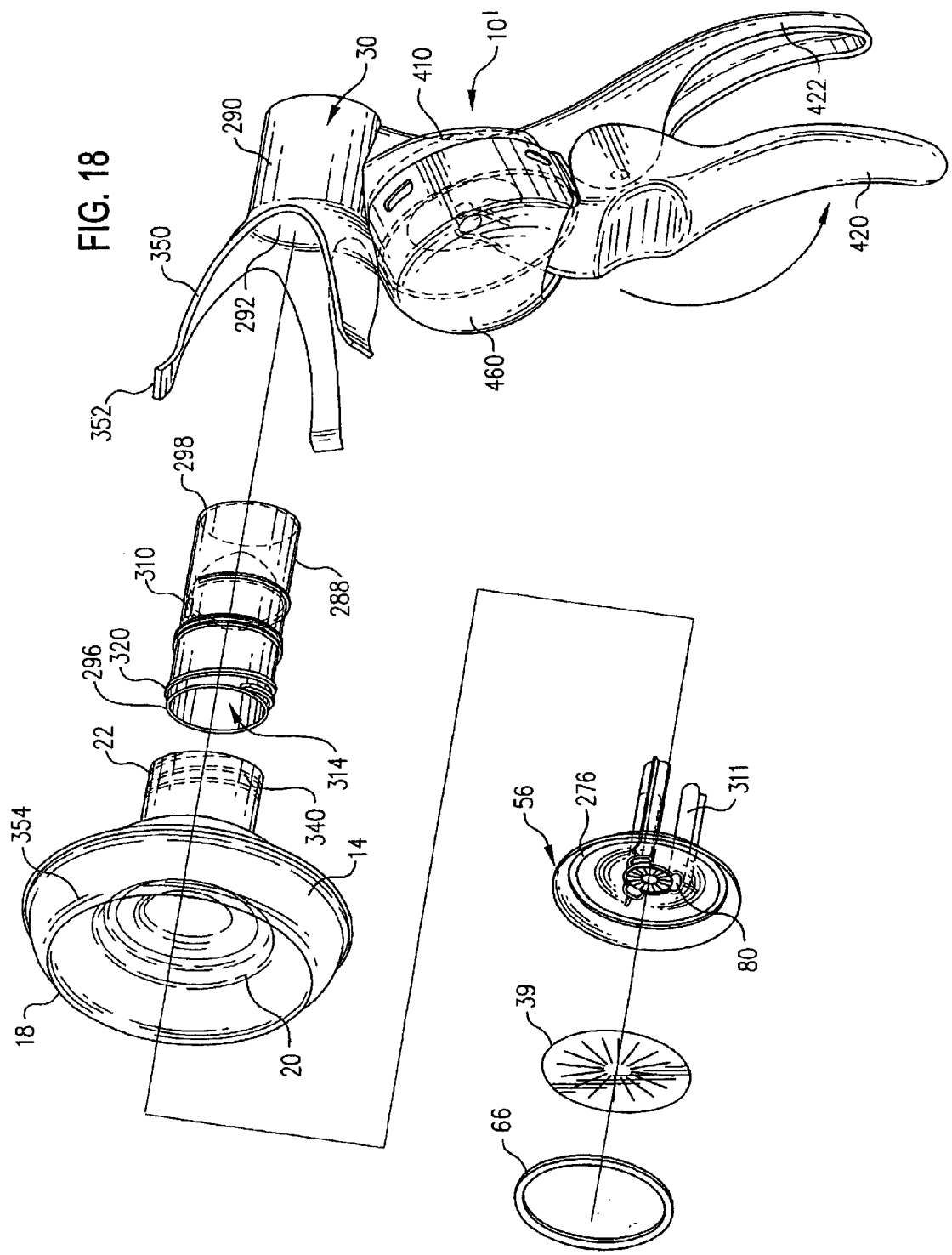
FIG. 18 is an exploded perspective view illustrating a hand-held breast pump of the invention employing a removable support member and removable fluid reservoir for primary and secondary sample collection.

In more detailed embodiments of the invention shown in FIGS. 16-18, the hand-held breast pump 10' is a modular device comprised of multiple, integrated components that are fixedly joined to one another when the pump is assembled, but can be readily detached or uncoupled from one another. This modular configuration of the device allows for interchanging of parts to adapt the pump for different patients and collection modes, and to facilitate storage, cleaning and/or servicing of the device. Thus, in one embodiment, the breast engaging portion 14 of the pump is provided as a separate, funnel shaped component that is detachable from one or more interconnecting components of the device (see, e.g., FIG. 18). In this manner, the engaging member can be removed from the rest of the device for cleaning and sterilization, or to allow for interchanging of different engaging members to accommodate breast anatomy differences among patients. Typically, the breast engaging member is removably coupled with a surface or member of the sample collection housing 30.

As illustrated in FIG. 18, the hand-held breast pump 10' of the invention incorporates the solid phase sample collection medium in fluid connection with the breast engaging member 14, typically by use of a support member 56 affixed to, or removably connected with, the engaging member. In selected embodiments, the support member encloses or supports one or more pads or sheets of absorbent or adsorbent material, for example a nitrocellulose membrane 39. Multiple pads or sheets of the same or different material may be used in combination (e.g., including a wetting member, a wicking member, or a partitioning member). Alternatively, the support member can incorporate or support a particulate solid phase sample collection medium, for example beads, resins, microspheres, particulate chromatographic media (e.g., agarose or silicate media), and the like. In yet additional aspects of the invention, the support member engages or supports a non-particulate solid template for sample collection, for example one or more capillary tubes, coated tubes, plates, wells, slides and the like formed of glass, plastic or other suitable materials. In certain embodiments, the support member may incorporate a compartment, well or reservoir to receive or introduce sample processing agents selected from chemical reagents, probes, blocking agents, buffering agents, denaturing agents.

The support member 56 for use in conjunction with the hand-held breast pump 10' is typically provided as a removable cassette that can be inserted within the engaging member 14, often to seat against the inner wall 20 thereof (see, e.g., FIGS. 16 and 18. In preferred aspects, the support member seats by a friction or compression fit against the inner wall of the engaging member, which may be facilitated by a complementary circumferential ridge and groove design between the support member and engaging member inner wall, as shown in FIG. 16.

In certain embodiments of the hand-held breast pump, a disc-shaped support member 56 is provided to support one or more sheets of absorbent or adsorbent material, such as a nitrocellulose membrane 39, in close proximity, or in contact with, the nipple 16 when the device is in use and suction is applied to the breast. As shown in FIGS. 16 and 18, the sheet is preferably secured by an upper retainer ring 66 fixedly or removably seated against an opposing surface (exemplified by a circumferential retainer groove 270) with the margin of the sheet sandwiched therebetween. This holds the sheet in place against negative pressure that may pass through the sheet when vacuum pressure is applied through the engaging member and to secure the sheet in position when the nipple impinges against it. The retainer ring may be integrally joined with the support member which may comprise a disposable refill, or the ring may be separable and the support member may comprise a reusable cassette for receiving replacement sheets. In an alternative design, there is no upper retaining ring and the membrane 39 or filter 40 simply rests upon the support member 56 or is removably coupled directly therewith (e.g., by wetting or gluing to create a temporary bond between the sheet and upper support member surface, or by appropriately sizing the sheet so that a peripheral edge of the sheet engages a surface of the support member in a friction or detent fit. Typically, the sheet is readily removable from the support member for processing, e.g., by hand or by using forceps or other conventional handling tools to disengage the filter or membrane.

Typically, the support member 56 for use with the hand-held breast pump device 10' includes air channels 80 that pass through the body of the support member to allow vacuum pressure applied from the vacuum pump 160 to reach the engaging member 14 of the pump during operation (i.e., by passing from the pump through the sample collection housing 30 and air channels to the engaging member). Likewise, the air channels allow venting of the engaging member for disengagement from the breast 17 after use. In certain embodiments, a plurality of two-three or more air channels are provided, which may be centrally located relative to a disc-shaped body of the support member as depicted in FIG. 18. The air channels can serve a dual purpose as channels for passage or transfer of fluids and/or fluid-suspended particles, including cells and cellular components, between the breast engaging member and the sample collection housing 30.

In one related aspect of the invention, cellular materials from expressed breast fluid are first collected on a primary solid phase sample collection medium (e.g., a membrane 39 or filter 40) mounted in fixed relation to the engaging member 14 (e.g., by a support member 56). In a secondary sample collection or processing step, the cellular materials are removed or flushed from the primary sample collection medium into a secondary solid phase sample collection medium (e.g., a solid phase sample collection template such as a plastic or glass slide, slip, tube, well or vial), optionally coupled with the support member and/or sample collection housing. The cellular materials can be directly transferred from the primary medium onto or into the secondary medium, for example by flushing the cellular materials from the primary medium (e.g., using physiological solutions, fixatives, etc.) directly into the secondary medium (e.g., a recess, well, vial or other receptacle coupled with or inserted into the support member or housing).

In one exemplary embodiment, cellular materials are collected from expressed breast fluid onto a primary sample collection medium comprising a filter, particulate medium, or nitrocellulose membrane 39. When a nitrocellulose membrane is used, the cellular materials are washed after primary collection from the membrane by a flushing rinse. For example, cytology fluid or another desired rinse liquid is used to transfer the cells from the primary collection medium into a secondary collection medium, typically a fluid-retaining well or reservoir integrated within, or coupled with, the support member 56 or the sample collection housing 30.

In more detailed embodiments of the invention, a nitrocellulose membrane 39 is employed for primary sample collection. The membrane is typically fluidly connected with the hand-held pump 10' by seating or mounting the filter on or within a support member 56, as described above. Nitrocellulose membranes are particularly well suited for collection of proteins, polynucleotides, or other soluble or suspended constituents of breast fluid. In preferred aspects, a nitrocellulose membrane is selected and employed within the device for collection of cytological specimens, particularly cells and cellular constituents. As illustrated in FIGS. 16-18, the filter (optionally supported by a support member) is positioned within the breast engaging member 14 near the base 22 of the engaging member proximate to the patient's nipple when the engaging member is seated against the breast. Comparing FIGS. 16 and 17, activation of suction pressure by manual operation of the device draws the nipple 16 into closer proximity to, or into actual physical contact with, the membrane, whereby the expressed fluid is efficiently transferred to the membrane.

Due to the fragility and fine porosity of nitrocellose membranes 39, it may be necessary to employ additional measures to protect the membrane against negative vacuum pressure and contact with the nipple 16 during operation of the pump 10'. In this regard, uniquely designed membranes and filters are provided for use within the device which feature perforations or slits that disrupt the planar surface of the membrane or filter to facilitate air passage therethrough and impart structural flexibility against mechanical perturbation. In one example, radial slits 280 emanate from a central disc portion 282 of the membrane or filter (FIG. 24) to allow passage of air through the membrane or filter during vacuum pressurization and to increase structural flexibility of the membrane or filter. Alternatively, one or more spiral perforations 284 (FIG. 25) or transverse slits 286 (FIG. 26) may be cut or stamped in the membrane or filter to achieve similar improvements in terms of permeability and flexibility.

Where the target constituent for collection from the expressed fluid is whole cells or cellular components, these materials may be partitioned onto the surface of a membrane or filter, typically a nitrocellulose membrane 39, for further processing and cytological examination. For this purpose, nitrocellulose membranes are employed that have a sufficiently small pore size to retain the cells or cellular debris on the outer (i.e., facing the nipple) membrane surface. For example, nitrocellulose membranes having a pore size of between about $0.5\mu$ and $5.0\mu$, preferably between about $1.0\mu$ and $2.0\mu$, are useful to partition whole cells on their surfaces.

As noted above, a fluid-retaining recess, well or reservoir may be fluidly connected to either the support member 56 or the sample collection housing 30 of the hand-held pump device 10' for primary and/or secondary sample collection. In certain embodiments, the fluid-retaining reservoir comprises an integral, defined compartment or enclosure within the sample collection housing for receipt of breast fluid and/or constituent samples thereof, including cytology specimens that may be washed into the reservoir after primary collection, as described above. Alternatively, the fluid well or reservoir can be a separable component of the sample collection housing, e.g., in the form of a flexible liner or rigid fluid reservoir member of the housing removably connected with a complementary housing member that partially or completely encloses or otherwise engages the fluid reservoir member.

Thus, as depicted in FIGS. 16 and 18, certain embodiments of the invention employ a removable fluid reservoir member 288 of the housing 30 for secondary sample collection of breast fluid components, including cytology specimens. In preferred embodiments, the removable reservoir member is provided in the form of a rigid sample collection tube or vial, exemplified by a standard cytology vial (i.e., a container having approximately the same general shape and dimensions as a standard cytology vial). The tube or vial is removably connected with a complementary housing member, for example an outer casing member 290 of the housing that partially or completely encloses the vial. Preferably, the tube or vial is sealably coupled with the outer casing member, for example by partially or completely nesting the vial within the outer casing member to form an airtight coupling therewith.

In various specific embodiments, the tube or vial engages an inner wall 292 of the casing member 290 and forms a generally airtight seal against it. For example, the casing member and vial may be complementarily sized and dimensioned to provide substantially airtight contact between the inner wall of the casing member wall and an outer wall 294, or a top end 296 or bottom end 298, of the vial when the casing member and vial are coupled to form the assembled housing. In certain embodiments, the outer wall of the vial features a circumferential ridge or fin 299 that engages and thereby makes a circumferential airtight seal against the inner wall of the casing member when the vial is nested with the casing member (see, e.g., FIGS. 16-20). In more detailed embodiments, the fin or ridge is replaced by a flexible O-ring 300 that seats in a circumferential O-ring groove 302 on the outer surface of the vial and forms a circumferential seal with the inner casing wall.

The purpose of the sealable coupling between the outer casing 290 and removable fluid reservoir 288 members of the housing 30 is to direct vacuum pressure from the vacuum pump 160 to the breast engaging member 14 in a path that includes the fluid reservoir member of the housing 30. In this manner, the removable reservoir is both gaseously and fluidly connected with the engaging member to facilitate secondary sample collection. To accomplish these objectives, the removable reservoir member is modified to include one or more air ports 310 that form a gaseous connection between the lumen of the reservoir (which is in turn connected to the engaging member, optionally via air channels 80 through a support member 56) and the vacuum pump. This allows the reservoir member to remain in place during primary and/or secondary sample collection, to function as both a conduit for vacuum pressure transmission to the breast and a receptacle for fluid sample materials (e.g., to directly collect expressed fluid or as a secondary collection medium to receive primarily collected sample materials washed or otherwise transferred from the primary sample collection medium).

In the latter context, the removable reservoir member 288 of the housing 30 may communicate for both fluid and gaseous transmission directly with the breast engaging member 14 of the device, or indirectly by way of the air channels 80 in the support member 56 optionally coupled with the engaging member. As noted above, the air channels can serve a dual purpose as channels for vacuum pressure transmission as well as transfer of fluids from the primary sample collection medium, through the air channels, into the removable reservoir (as exemplified by transfer of "wash" fluid containing cells and cellular components flushed from a primary collector, e.g., a nitrocellulose membrane, mounted in the support member, through the air channels, and into the secondary collection fluid reservoir). To facilitate this and related purposes, the channels may extend through tubular basal columns 311 or other fluid connection ports that extend from the support member toward, or into, a lumen 314 of the reservoir member of the housing.

Figure 19:
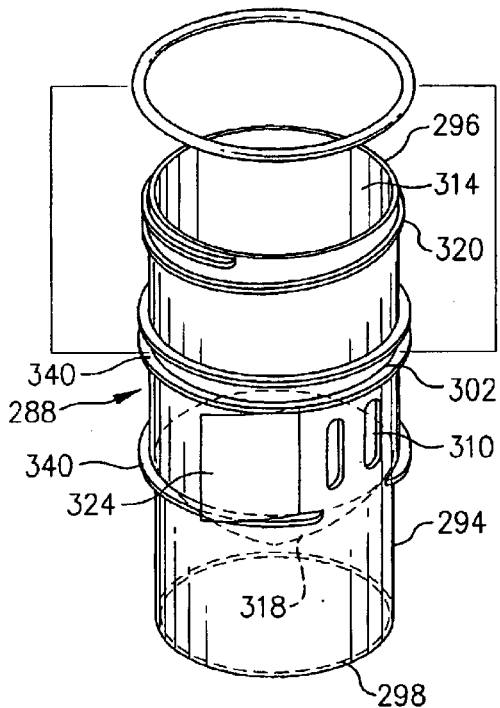
FIGS. 19 and 20 provide perspective views of alternative embodiments of a removable sample collection reservoir for use with the hand-held breast pump of the invention.
Figure 20:
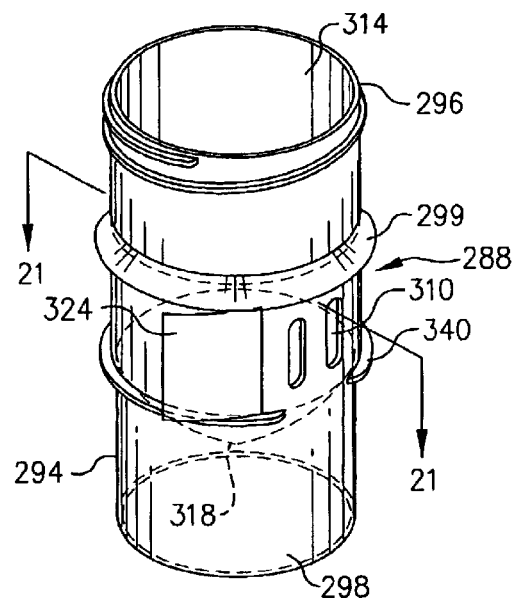

In the embodiment of a hand-held pump device 10' illustrated in FIGS. 16-20, the reservoir member 288 is a cytology vial removably, sealably coupled with the outer casing member 290 to form the assembled housing 30. To achieve this sealable coupling, the outer wall 294 of the vial features a circumferential fin 299, or a flexible O-ring 300 seated in a circumferential O-ring groove 302, that forms a circumferential seal with the inner wall 292 of the casing member (see, e.g., FIGS. 16, 19 and 20). The vial incorporates one or more air ports 310 that communicate between the outer wall and the inner lumen 314 of the vial to form a gaseous connection between the lumen of the vial, the vacuum pump 160, and the breast engaging member 14. Preferably, multiple air ports are provided, which are located on the side of the vial positioned below (i.e., toward the bottom end 298 of the vial) the ridge or O-ring that forms the gaseous seal with the wall of the casing member. Alternatively, the air ports can be located at other positions on the vial, e.g., in a lower side wall or floor wall 318, provided the position is suitable to maintaining the desired path of vacuum pressure flow and retaining fluids within the reservoir. In this context, it is noted that certain embodiments of the fluid reservoir member of the housing will dictate changes in the position of the air port(s). For example, where a cytology vial-shaped reservoir is selected, as shown in FIGS. 16 and 20, the floor wall may be raised relative to the bottom end 298 of the vial, to reduce the sample volume of the vial for handling and processing purposes. To accommodate this and other designs, the air ports are desirably positioned in the outer (side) wall 294 of the reservoir between the floor wall and the sealing flange 299 or O-ring 300.

Referring to FIGS. 19 and 20, further modifications of the removable fluid reservoir member 288 of the housing 30 provides for multi-purpose use of the reservoir member for sample collection in a clinical setting, as well as sample storage, transport and/or processing in a laboratory setting. To facilitate these latter purposes, the removable reservoir member may be provided with closure means for closure of the reservoir after sample collection is completed—to prevent sample contamination and spillage. Taking the cytology vial reservoir for example, the top end 296 of the vial may be adapted to provide a sealable primary closure for the main opening of the vial. For example, the vial top end can be provided with complementary threads 320 or other closure means to receive a conventional cap that is sized and dimensioned (e.g., complementarily threaded) to sealably engage the vial top end. In conjunction with this use, and further considering the novel adaptation of the fluid reservoir member to provide a secondary opening (i.e., the integral air port 310 that functions as a vacuum connection), the reservoir is also equipped with secondary closure means to sealably close the air ports after sample collection. A variety of air port configurations are contemplated, which can be sealed using a commensurate variety of closure mechanisms. For example, the air port or ports can be sealed using a flexible (e.g., rubber) stopper shaped and dimensioned to sealably plug into the port opening. Alternatively, the port can be closed by an adhesive seal or sticker that adheres to the outer wall 294 of the reservoir member surrounding the port opening.

Figure 21:
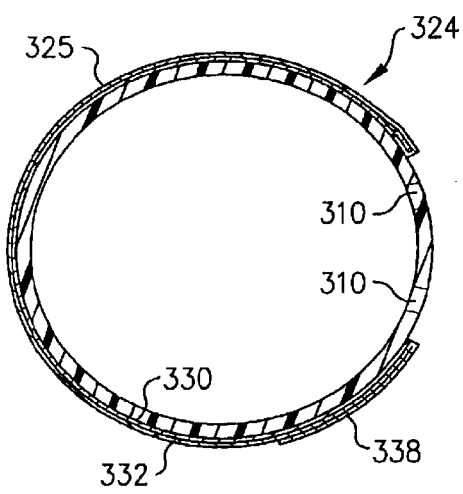
FIGS. 21-23 provide sectional views of the removable fluid reservoir of FIG. 19, illustrating operation of a closure/labeling strip to seal the reservoir and provide an exterior labeling surface for recordation of sample data.
Figure 22:
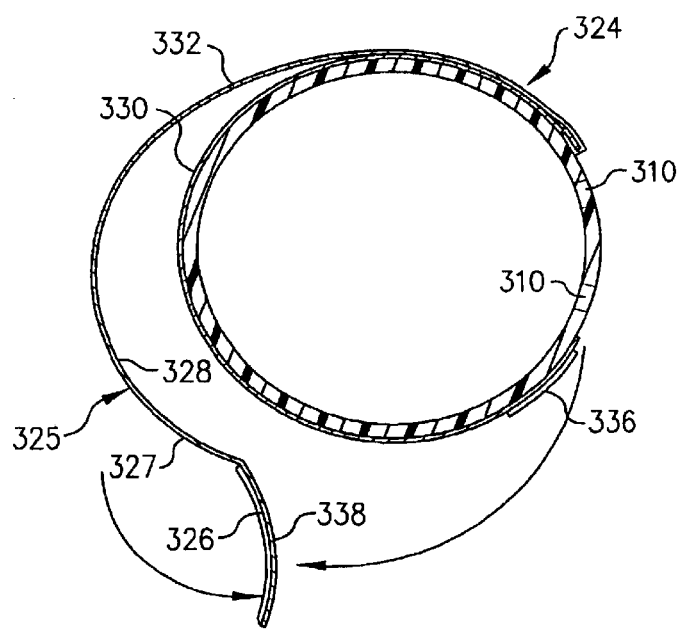

With respect to the latter secondary closure design, the invention provides a combined closure and labeling device 324 which functions both as a secondary closure mechanism to seal the air port 310 of the removable reservoir and as a labeling template to provide a convenient writing surface for sample labeling (see, e.g., FIGS. 21 and 22). This aspect of the invention may be achieved, for example, by providing any of a variety of adhesive closure/labeling tabs which may be directly applied to seal the air port after sample collection. This simple type of closure/labeling tab can, for example, be provided as a separate adhesive sticker having a first, closure-forming surface 325 bearing an adhesive coating 326 on at least a portion of said surface, for application over the air port to form a seal, e.g., by adhesive contact with the outer wall 294 of the removable reservoir. The adhesive coating preferably forms a seal that is resistant to disruption by contact with aqueous solutions and other materials present in the collected samples, for example buffers and fixatives. The adhesive coating is also preferably shielded before use by a protective tab or other protective surface 327 that covers the coating and is removed therefrom prior to use to expose the adhesive coating.

The closure/labeling device 324 has a second, labeling surface 328 opposite the closure-forming surface 325 that is made of a blank template material suitable for receiving a stable, ink or graphite imprint thereon. For example, the second surface may be made of cellulose or other fibrous material adapted for imprinting sample data upon the surface thereof using a pen, pencil or other writing implement. Alternatively, the second, labeling surface may be made of plastic or other material adapted for retaining data imprinted in permanent ink (e.g., using an alcohol-based marker). When the adhesive tab is applied over the air port, the blank template material of the second, labeling surface of the tab is facing outward and at least a portion of the surface covers a smooth portion of the outer wall of the removable reservoir 288, to allow the doctor or technician to imprint a clear data record on the labeling surface.

Figure 23:
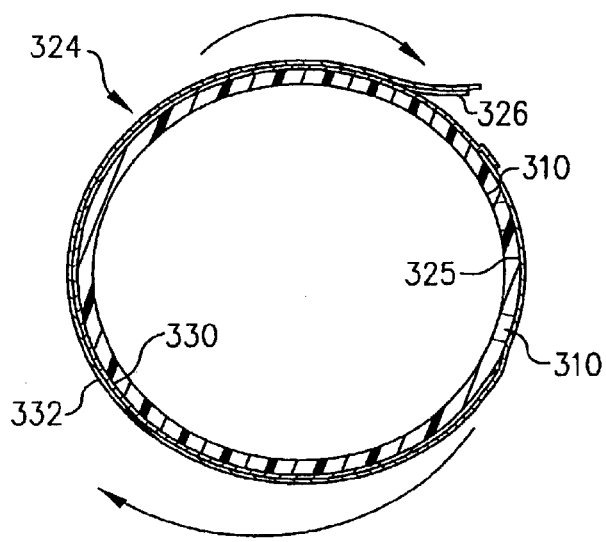
Figure 24:
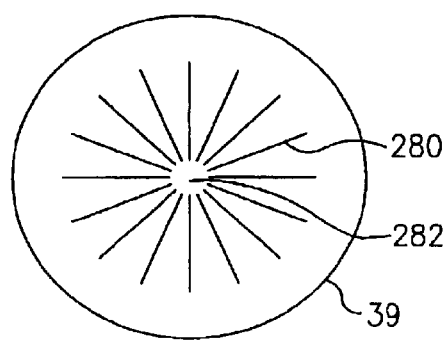
FIGS. 24-26 provide top plan views of a modified membrane or filter for use within the breast pump of the invention having perforations or slits for enhancing permeability and flexibility of the membrane or filter.
Figure 25:
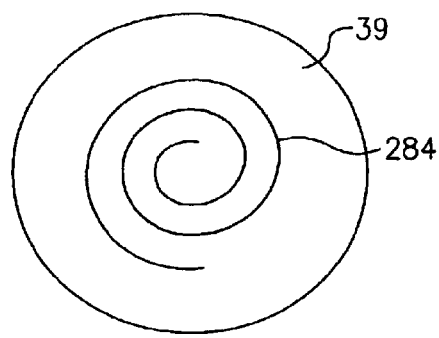
Figure 26:
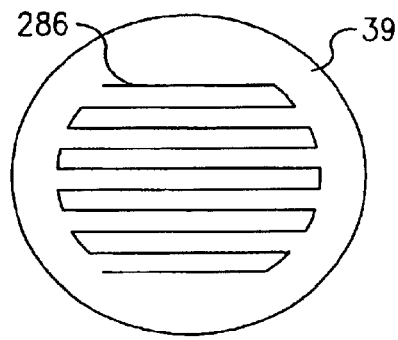

In more detailed embodiments, the closure/labeling device 324 is affixed to the removable reservoir 288 during operation of the hand-held breast pump 10' in a first, open configuration that leaves the air port 310 uncovered for transmission of vacuum pressure (see, e.g., FIG. 23). The closure/labeling device which is thus pre-attached to the reservoir can be manually repositioned, or otherwise manipulated, after sample collection to a second, closed configuration to form a seal or closure against the air port (see, e.g., FIG. 21). In the exemplary embodiment shown in FIGS. 19-23, the closure/labeling device comprises an adhesive strip that is folded in a first, open configuration (FIG. 21) to form two layers—an inner layer 330 that is affixed to the reservoir proximate to, but not covering, the air port, and an outer layer 332 that folds back over the inner layer in the open configuration. In this embodiment, the outer layer of the strip provides both the first, closure-forming surface 325 with the adhesive coating 326 for securing closure of the strip, and the second, labeling surface 328 formed of the blank template material opposite the closure-forming surface. In the open configuration, the outer layer is optionally secured in the folded-back position against the inner layer by engagement of the labeling surface with the inner layer, for example by a second adhesive coating 336 on the inner layer that holds the two layers together in the folded position. Also optionally, the adhesive coating 326 of the first, closure-forming surface may be protected in the open configuration by folding an end segment 338 of the outer layer 325 bearing the adhesive coating 326 for closure back on itself, so that the closure forming surface 325 provides the protective surface 327 to shield the adhesive prior to closure (as shown in FIGS. 21 and 22). To manipulate this closure/labeling device into the second, closed configuration, the end segment can then be lifted and pulled outward to release the outer layer 332 from the inner layer 330 and to unfold the end segment to separate the adhesive coating 326 on the closure-forming surface 325 from the protective surface 327. The outer layer 332 is then unfolded away from the inner layer and wrapped around the reservoir so that the closure-forming surface covers the air port to form a closure that is water-tight or water-resistant to effectively prevent sample spillage from the reservoir and contamination. In this context, closure is effectuated by direct apposition of the adhesive coating 326 to the outer wall 294 of the reservoir surrounding the air port, or by drawing the outer layer tight across the air port and annealing the adhesive surface back upon the inner layer. In either case, manipulation of the closure/labeling strip to the closed configuration positions the labeling surface 328 to face outward for easy recordation of sample data. In yet additional detailed embodiments, the closure/labeling strip can be better secured against dislodgement during loading and removal of the reservoir 288 by including one or more circumferential guide ridges 340 (see FIGS. 19 and 20) on the exterior of the reservoir, to shield the closure/labeling strip from mechanical dislodgement and/or to increase the fidelity of the closure against leakage.

In related aspects of the invention, a novel breast fluid collection reservoir is provided for use within a mammary fluid collection device of the invention, which incorporates the foregoing features of the removable reservoir member of the sample collection housing. The novel collection reservoir as described in the foregoing passages is useful within the breast fluid collection methods of the invention, as well as within various sample handling, processing, and diagnostic assay methods performed in the laboratory subsequent to collection of a breast fluid sample.

The novel breast fluid collection reservoir of the invention is typically provided in the form of a rigid tube or vial, for example in the form of a modified cytology vial, having a top end which defines a primary opening for access to the sample. The reservoir further comprises an outer reservoir wall, typically a cylindrical sidewall of a tubular reservoir closed at a bottom end thereof, e.g., by a floor wall, as described above. The outer reservoir wall defines one or more air ports that communicate between the outer wall and an inner lumen of the vial. In more detailed embodiments, the fluid-retaining reservoir comprises a removable fluid reservoir member of a sample collection housing of a mammary fluid collection device. Typically, reservoir member is a rigid sample collection tube or vial removably connected with an outer casing member of the sample collection housing of the collection device.

Within this aspect of the invention, the reservoir may be adapted for removable, sealable connection with the outer casing member of said housing, to form an airtight coupling therewith. In certain embodiments, the fluid-retaining reservoir is a cytology vial sealably connectable with the outer casing member to form the airtight coupling. For example, the fluid-retaining reservoir can be removably nested within the casing member to form a substantially airtight contact between an inner wall of the casing member wall and an outer wall, or a top or bottom end, of the reservoir member. To achieve this function, the outer wall of the fluid-retaining reservoir may be provided with a circumferential ridge, fin or O-ring adapted to engage and make a circumferential airtight seal against the inner wall of the casing member.

In more detailed aspects, the fluid-containing reservoir member for use within the devices and methods of the invention includes a closure device for closing the reservoir after the sample of mammary fluid is introduced therein, to prevent sample contamination and spillage. The closure may comprise a simple cap adapted to sealably engage a top end of the reservoir. The cap or similar "primary closure" may extend to cover the air port(s) of the reservoir, which may be contiguous with the top opening of the reservoir or separate therefrom. In alternative embodiments, secondary closure means may be provided which are specifically adapted for closure of the air port(s). The secondary closure means may comprise a plug, cap or adhesive seal or sticker sized and constructed to engage or adhere to the outer wall of the reservoir member at or surrounding the air port opening(s) to form the closure.

In certain embodiments, the secondary closure means comprises a combined closure and labeling device which functions as a secondary closure mechanism to seal the air port(s) of the reservoir and as a labeling template to provide a writing surface for sample labeling. Often, the secondary closure means comprise a combined closure and labeling tab or sticker for application to the outer wall of the reservoir to seal the air port after the sample is collected. The tab or sticker has a first, closure-forming surface for application over the air port to form a seal by juxtaposition or adhesive contact with the outer wall of the reservoir, and a second, labeling surface opposite the closure-forming surface made of a blank template material for imprinting written information thereon. The first, closure-forming surface typically has a water-insoluble adhesive coating on at least a portion of the surface. In more detailed embodiments, the tab or sticker is pre-attached to the removable reservoir member in a first, open configuration and can be manually repositioned or otherwise manipulated after sample collection to a second, closed configuration to form a seal or closure against the air port(s), as described in detail above.

In yet additional, related aspects of the invention, methods for breast fluid sample collection, sample handling, and/or sample processing are provided which incorporate the novel fluid-retaining reservoir adapted for use with a hand-held breast pump 10' of the invention. These methods include, generally methods for collecting breast fluid samples which involve collecting expressed mammary fluid in a modified fluid reservoir as described above. Additional methods involve loading and removal of a modified fluid-retaining reservoir within a hand-held breast pump, according to the above description. Related methods include an additional step of securing the primary and/or secondary closure means of the reservoir after a sample of mammary fluid, or a component thereof, is collected therein.

Related to these methods, the invention provides additional methods for handling or processing biological samples of mammary fluid, or components thereof, for use in a diagnostic assay to detect or quantify a breast disease marker in the sample. The methods generally involve providing or obtaining the biological sample of mammary fluid or a mammary fluid component in a specialized fluid-retaining reservoir according to the above description. The sample may be initially collected by oxytocin induction or by application of a breast pump 10, 10' of the invention without oxytocin priming. The reservoir is typically provided as a flask, vial, or tube that has a top end defining a primary opening for collection of, and later access to, the mammary fluid sample, and an outer reservoir wall that defines one or more air ports communicating between the outer wall and an inner lumen of the vial.

In more detailed handling and processing methods, the reservoir incorporates specialized closure means, for example a cap that secures the top end of the reservoir and secondary closure means to sealably close one or more air port(s) of the reservoir, to close the reservoir after the sample is collected and thereby prevent sample contamination and spillage. Typically, the fluid-retaining reservoir is a modified cytology vial adapted as a removable reservoir member integrated with a hand-held mammary fluid collection pump 10' as described above. More detailed handling/processing methods employing the novel reservoir include the step of accessing said sample within the reservoir to transfer or process the sample for detection or quantification of a breast disease marker. Additional methods include one or more steps of processing the sample to detect or quantify the breast disease marker.

In additional detailed embodiments, the step of processing the sample for marker detection comprises fixing or staining cells or cell fragments in the sample, before or after transfer of the sample from the reservoir, e.g., for cytological analysis. Yet additional methods involve exposing the sample in the reservoir or after transfer to a processing reagent, e.g., a fixative, labeling reagent, buffer, etc., to prepare sample components, including whole mammary fluid, whole cells, cell fragments, cell membranes, purified proteins, bulk proteins, glycoproteins, peptides and/or polynucleotide components, for further processing, which may include detection or quantification as the selected breast disease marker(s).

As noted above, certain modular designs for the hand-held breast pump 10' of the invention feature a separate breast engaging member 14 provided as a funnel shaped component adapted for removable coupling to one or more interconnecting components of the device for cleaning and interchanging of parts. Typically, the breast engaging member is removably coupled with the sample collection housing 30. In one embodiment shown in FIGS. 16-18, the housing is comprised of multiple members, exemplified by an outer casing member 290 and a removable, fluid reservoir member 288. As illustrated in FIG. 18, the engaging member may be directly coupled to the fluid reservoir member, which is in turn engaged by a sealable connection (e.g., a sealable compression fit) with the outer casing member of the housing as described above. In this context, one alternative coupling design is for the engaging member to be fitted with mounting threads 340 or other coupling means to couple with complementary threads 320 or other closure means on the top end 296 of the removable reservoir (e.g., cytology vial). In this manner, the closure means of the removable reservoir, adapted to receive a conventional cap that sealably engages the reservoir top end, serves the dual purpose of coupling the engaging member 14 with the remaining modular components of the device. Alternative coupling means are of course contemplated as well, as exemplified by a simple pressure fit coupling to removably couple mated ends of the engaging member and reservoir member. To facilitate stable coupling of the engaging member with the sample collection housing 30, the housing may be further elaborated to include flared extensions 350 terminating in outwardly reflected feet 352 collectively shaped and dimensioned to engage an inner, circumferential groove 354 underlying the flared or reflected terminal edge 18 of the engaging member (see, e.g., FIG. 18).

In addition to the foregoing features, the hand-held breast pump 10' of the invention may optionally include any of the alternative features described above for the general-purpose breast pump 10, including different solid phase sample collection media and support member 56 designs. Thus, the support member for use with the hand-held pump can also include a fluid-retaining well which may be optionally filled with a desired solution, such as a buffer, a solution containing a probe, cross-linking agent, blocking agent, denaturing agent, etc., to facilitate sample collection, handling, and/or processing. Alternative designs and configurations of the housing 30 and/or support member 56 are also provided which vary with the type of solid phase sample collection medium used. For example, when a particulate solid phase sample collection medium 41 (e.g. beads, resins, or microspheres) is used, the medium may be enclosed in a cartridge 82 removably mounted to, or integrated within, the support member or otherwise removably connected to the sample collection housing 30, as described in detail above. It is also contemplated to adjustably mount the solid phase medium relative to the housing 30 of the hand held pump device, so that the collection medium can be moved closer to, or farther away from, the base 22 of the engaging portion 14 of the pump 10. In this regard, various designs are contemplated commensurate with the above description to provide a reciprocating mechanism that adjustably moves the solid phase collection medium in closer, or more distant, proximity to the nipple when the hand-held breast pump is engaged therewith.

Within more detailed aspects of the invention, the hand-held breast pump 10' typically incorporates a compact vacuum pump housing 410 which structurally and functionally integrates the vacuum pump 160 with the sample collection housing 30 and, in turn, with the engaging member 14 (see, e.g., FIGS. 16-18). The vacuum pump housing is in turn coupled with, or is modified to include, a vacuum pump actuating mechanism. The actuating mechanism may be in the form of a switch, button, lever or other actuation device suitable for use with the selected vacuum pump. As noted above, a variety of vacuum pumps may be incorporated within the breast pump device, including any manual or electric, piston, hydraulic or diaphragm pump of suitable size and dimension for incorporation in the hand-held pump vacuum housing. In the exemplary embodiment depicted in FIGS. 16-18, the vacuum pump is a conventional diaphragm pump, and the pump actuation mechanism is a simple hand lever 420 pivotally connected to the pump housing or other suitable connection point.

Exemplifying this aspect of the invention, the pump housing is optionally coupled with, or extended to include, an opposing handle 422 to facilitate depression of the hand lever by gripping and manual closure of the lever toward the handle (compare FIGS. 16 and 17). The handle is preferably molded or cast as an integral extension of the vacuum pump housing. In more detailed embodiments, exemplified in FIGS. 16-18, the vacuum pump housing and handle are molded or cast together as an integral unit or modular component with the outer casing member 290 of the sample collection housing 30. The handle defines a pivot recess 430 or detent that pivotally receives a pivot head 432 or shaft joined or integrated with the pump actuation lever (as shown in FIGS. 16 and 17).

In this manner the pump actuating lever 420 is pivotally connected to the pump housing 410 or handle 422 by a pivotal connection 430, 432 that joins the actuation lever and pump housing in an easily assembled fashion, e.g., by snap fitting the pivot head 432 of the lever into the pivot recess 432 of the handle. The actuation lever easily and effectively actuates the vacuum pump 160 by depressing the lever to draw a flexible diaphragm member 440 downward, away from a primary vacuum chamber 442 connected with, or integrated within, the sample collection housing. In the embodiment shown in FIGS. 16-18, the primary vacuum chamber is integrally formed as a channel within the vacuum pump housing proximate the flexible diaphragm member and extending to a communicating port 444 opening to the inner wall 292 of the outer casing member 290 of the housing. The remainder of the vacuum path (i.e., through the outer casing member to the air port 310 of the removable fluid reservoir member 288 of the housing into the lumen 314 of the reservoir, optionally through air channels 80 of the support member 56, and to the breast engaging member) is described above.

To engage and move the flexible diaphragm member 440 in this fashion, the actuation lever engages a diaphragm retraction mechanism, for example comprising a reciprocating shaft 450 or piston sealably connected through the diaphragm to a diaphragm-engaging head 452, to collectively translate depression movement of the lever to downward retraction of the flexible diaphragm member (compare, e.g., FIGS. 16 and 17). These components of a diaphragm pump are conveniently housed within a protective pump cover 460 which engages a complementary rim 462 or other coupling surface of the pump housing 410 by a complementary engagement fitting (arrows 464). This coupling may optionally serve to sealably anchor the flexible diaphragm member, e.g., by sandwiching a peripheral edge 466 of the diaphragm between the cap and housing as shown in the figures. Optional pump devices, actuation mechanisms, and pump housing designs are contemplated within the invention, which are within the level of skill in the art to engineer for use with the hand-held breast pump devices disclosed herein.

As noted above, mammary fluid expression and collection using the devices of the invention may be facilitated in certain instances by prior or concurrent administration of the peptide hormone oxytocin, or an analog thereof, in an amount that is effective to stimulate myoeptithelial contraction in the alveolar gland ducts of the breast to facilitate expression of the mammary fluid from the nipple. Preferably the oxytocin preparation is administered intranasally and is administered in an amount that is intranasally effective to stimulate expression of mammary fluid from the nipple. Alternatively, an intramuscular or intravascular injection of oxytocin can effect the same myoepithelial contraction response as the intranasal administration route. The amount, timing and/or mode of oxytocin administration may be adjusted on an individual basis depending on such factors as menstrual cycle stage, use of birth control or hormone replacement therapy, pregnancy history, age of onset of menarche, ethnicity and other factors known to affect an individual's propensity for breast fluid expression.

Oxytocin is a peptide hormone of pituitary origin that is naturally released into the bloodstream of lactating women in response to suckling, and stimulates contraction of myoepithelial cells in the mammary alveoli and ducts to cause milk ejection (Cobo, *J. Perinat. Med.* 21:77–85, 1993). The drug has also been widely used for stimulating labor in pregnant women, due to its activity of stimulating uterine contractions (Satin et al., *Am. J. Obstet. Gynecol.* 166:1260–1261, 1992). For these reasons, the pharmacology of oxytocin has been thoroughly investigated, including detailed studies of effective dosages, half-life and potential side effects.

For use in the present invention, an oxytocin preparation is provided for intranasal, intramuscular, or intravenous administration that contains oxytocin in a biologically suitable, liquid carrier. As used herein, "oxytocin" refers to natural or synthetic oxytocin and biologically active derivatives and analogs thereof. Naturally occurring oxytocin from mammalian sources is of course suitable, as are other known, naturally occurring oxytocin-like peptide analogues and their synthetic counterparts having similar activities for stimulating alveolar-ductal myoepithelial contraction. Preferably, the oxytocin used within the invention is a simple peptide hormone comprising a cyclic peptide, the peptide having a well defined ring portion (Cys-Tyr-Ile-Gln-Asn-Cys) and tail portion (Pro-Leu-Gly). However, numerous derivatives and analogues are known, or readily obtainable, in the art, e.g., derivatives or analogues having amino acid truncations, deletions or substitutions at one or more residues of the peptide and which exhibit substantially the same activity as naturally occurring oxytocin (i.e., having at least 75%, and preferably 85%–95% or more, activity compared to that of native oxytocin for stimulating alveolar-ductal myoepithelial contraction). The most economic oxytocin preparations for use within the invention contain a synthetic oxytocin (e.g. Pitocin® or Syntocinon® available from various providers, for example Sandoz (Basel, Switzerland) and United States Pharmacopeia. Alternate benefits may be obtained with the use of a long-acting oxytocin analog within the methods of the invention. The utility and pharmacokinetics of such analogs, exemplified by the peptide analog carbetocin, are described in detail in U.S. patent application Ser. No. 09/481,058 filed Jan. 11, 2000 (incorporated herein by reference).

For use with the methods, devices and kits of the invention, a preferred oxytocin preparation contains approximately 40 USP units of oxytocin per ml of liquid carrier. Preferred liquid carriers are biologically compatible solutions, such as a lactated Ringer's solution or other physiologically balanced, sterile, non-toxic and non-irritative solution. To administer the oxytocin intranasally, a standard nasal squeeze bottle is used, which delivers approximately 0.5 ml of the oxytocin preparation into the patient's nostril when squeezed. The oxytocin is absorbed by the nasal mucosa into the systemic circulation where it reaches and acts specifically on the myoepithelial cells surrounding the alveoli of the breast and making up the walls of the lactiferous ducts, causing their smooth muscle fibers to contract and force any fluids present into the large ducts or sinuses where it can be expressed from the nipple spontaneously onto a sample collector or by the further action of a breast pump. Intranasal application of the spray preparation is therefore a practical and effective method of administration. The half-life of oxytocin in the human bloodstream is extremely short, estimated to be about 10–15 minutes or less, due to its rapid removal from plasma by the kidney, liver, and mammary gland, and the time to pharmacokinetic and clinical steady state is readily determined depending on the mode of administration (e.g. bolus dosage, repeat administration, or steady infusion). (See for example, Gonser, *Arch. Gynecol. Obstet.* 256:63–66, 1995; and Orhue, *Obstet. Gynecol.* 83:229–233, 1994, each incorporated herein by reference in its entirety). It is therefore a routine matter to determine an appropriate concentration and dose of the oxytocin preparation to administer an effective amount (either intranasally effective, intravenously effective, or intramuscularly effective) of the oxytocin to cause expression of mammary fluid with or without the assistance of a breast pump. (See for example, Newton, *Ann. N.Y. Acad. Sci.* 652:481–483; Mena, *Neuroendocrinology* 61:722–730, 1995; Gonser, *Arch. Gynecol. Obstet.* 256:63–66, 1995; Orhue, *Obstet. Gynecol.* 83:229–233, 1994; Satin et al., *Am. J. Obstet. Gynecol.* 166:1260–1261, 1992; and Satin et al, *Obstet. Gynecol.* 83:234–238, 1994, each incorporated herein by reference in its entirety).

Although not all female patients are expected to be responsive to intranasal oxytocin stimulation, an intranasally effective amount of oxytocin for the purposes of the invention can be readily determined. As used herein, an intranasally effective amount of oxytocin is an amount of oxytocin sufficient to intranasally stimulate the expression of at least 3 $\mu$l of mammary fluid in at least 50% of non-lactating female patients with the aid of negative pressure to the nipple of between 50–200 mm Hg applied by the breast pump (up to 45 min after a first administration of the oxytocin spray). It may be necessary, and indeed preferred, to administer a low, preliminary dose of oxytocin to the patient, for example a single spray of a 40 Unit/ml oxytocin solution in each nostril, or multiple sprays of a lower concentration oxytocin preparation, and thereafter wait to determine a particular patient's sensitivity. If there is no reaction with an initial application of the breast pump after a short post-administration period of 2–15 minutes, and preferably 2–5 minutes, a booster dose of the oxytocin spray may be administered and the pump reapplied. In this way, the clinician can modulate the dosage to each patient's varying sensitivity, and thereby minimize potential adverse side effects. Alternatively, an effective dose of intramuscular or intravenous oxytocin can be used according to the same dosage determination and administration principles in patients where intranasal administration fails or is otherwise contra-indicated as a preferred mode of administration.

As noted above, the amount, timing and/or mode of oxytocin administration may be adjusted based on specific factors known to render individuals more or less sensitive to induction of breast fluid expression. These factors are generally well known in the art, and include, for example, menstrual cycle stage, use of birth control or hormone replacement therapy, pregnancy history, age of onset of menarche, and ethnicity, among other factors.

Thus, in one aspect of the invention, methods for obtaining a biological sample from a patient and/or determining the amount of a breast disease marker in a biological sample from breast fluid are provided which include a step of determining a menstrual stage of the patient. Based on the determined menstrual stage, a drug administration protocol is selected having a predetermined oxytocin dosage, timing and/or frequency of oxytocin delivery, and/or mode of oxytocin administration.

According to these methods, one or more variables of oxytocin dosage, timing and/or frequency of oxytocin delivery, and/or mode of oxytocin administration are selected depending on whether the patient is staged within one of five approximate menstrual phases. These phases include 1) a proliferative phase (characterized by a tight configuration of the alveolar lumena); 2) a follicular phase (characterized by a defined configuration of the alveolar lumena); 3) a luteal phase (characterized by an open configuration of the alveolar lumena, with some secretion by the alveolar cells); 4) a secretory phase (characterized by an open configuration of the alveolar lumena, with secretion by the alveolar cells); and 5) a menstrual phase (characterized by a distended configuration of the alveolar lumena, with secretion by the alveolar cells).

It is generally not desired to conduct the methods of the invention for patients staged in the proliferative or follicular stage of their menstrual cycle (approximately 3–7 days and 8–14 days, respectively). However, in some circumstances sample collection can be performed for these individuals using high and/or repetitive doses of oxytocin and otherwise optimizing the breast fluid expression response by selecting a particular mode of oxytocin administration, or combination thereof (e.g., intravenous administration followed by intranasal administration). For patients staged in the luteal or secretory stage of their menstrual cycle (approximately 15–20 days and 21–27 days, respectively), intermediate dosages of oxytocin are selected and repetitive administrations are reduced or eliminated. For patients staged in the menstrual phase, dosages of oxytocin and repetitive administrations are reduced even further while still providing an effective administration protocol to yield sufficient breast fluid expression.

Determination of effective administration protocols for patients of different menstrual stages can also be readily achieved within the invention. As used herein, an effective administration protocol yields at least 3 $\mu$l of expressed mammary fluid in at least 50% of non-lactating female patients at an equivalent menstrual stage with the aid of negative pressure to the nipple of between 50–200 mm Hg applied by a breast pump up to 45 min after a first administration of the oxytocin spray. Various combinations of oxytocin dosage, timing and/or frequency of oxytocin delivery, and/or mode of oxytocin administration are contemplated, as can be readily determined by the skilled artisan in accordance with the teachings herein. Likewise, it will often be preferred to administer a low, preliminary dose of oxytocin to the patient and thereafter wait to determine a particular patient's sensitivity, even when an individual's menstrual stage has been determined and a particular administration protocol selected. Thus, if there is no reaction with an initial application of the breast pump after a short post-administration period, a booster dose of the oxytocin may be administered and the pump reapplied. In this way also, the clinician can apply a first, stage specific dose of oxytocin and thereafter modulate the dosage, period of time between booster administrations, and/or mode of administration, to each patient's varying sensitivity.

In other, related aspects of the invention, methods for obtaining a biological sample from a patient and/or determining the amount of a breast disease marker in a biological sample from breast fluid are provided which include a step of determining a non-menstrual stage patient sensitivity index. Examples of such indices include 1) patient use of hormone based birth control; 2) patient use of hormone replacement therapy; 3) patient pregnancy history; 4) patient age of onset of menarche; and 5) patient ethnicity. Other indices associated with sensitivity to induction of breast fluid expression are also contemplated. These factors can be determined by such routine steps as patient consultation, evaluation of patient records, and clinical or laboratory-based analysis (e.g., physical screening, measurement of sex-steroid hormone levels, etc.).

Based on a determined non-menstrual stage sensitivity index, an effective drug administration protocol is selected having a predetermined oxytocin dosage, timing and/or frequency of oxytocin delivery, and/or mode of oxytocin administration, in accordance with the methods described above. In yet additional methods an effective drug administration protocol is selected by first determining both a patient's menstrual stage and at least one non-menstrual stage sensitivity index specific to the patient, and thereafter selecting an effective oxytocin administration protocol based on these combined indices.

In yet additional methods within the invention, it may be preferred to conduct the foregoing sample collection methods in conjunction with a conventional mammographic procedure. In this manner, costs, time and patient discomfort can be minimized. Further, by conducting the sample collection immediately following a mammogram it is expected that breast fluid expression may be facilitated by breast manipulation during the initial procedure. Additional steps to facilitate breast fluid expression include manual breast massage and application of heat packs to the breast.

For mammary fluid collection using a breast pump 10, 10' of the invention, alone or in conjunction with oxytocin stimulation, the breast pump is applied and negative pressure is generated on the breast to facilitate the expression of mammary fluid. Within the methods of the invention, negative pressures of 50–200 mm Hg are preferred, and these pressures are maintained, preferably intermittently, for approximately 1–15 minutes, depending on the sensitivity of individual patients, oxytocin dosage and other factors. The volume of expressed mammary fluid will vary depending on a variety of factors, including the time and pressure of breast pump administration, and other factors. For the least sensitive breast marker assays of the invention, a volume of expressed mammary fluid of 300–500 $\mu$l is preferred to provide ample material for conducting the assay, and these volumes will be obtainable from a substantial proportion of women treated according to the above methods. To express 300–500 $\mu$l of mammary fluid, some women will require repeated stimulation treatments, perhaps requiring pooling of mammary fluid samples obtained during multiple patient visits. However, for more sensitive assays of the invention, e.g. solid phase immunoassays, much smaller samples of 3 $\mu$l or less will be suitable to carry out the assays, particularly in the case of breast cancer markers that are naturally secreted into the mammary fluid and are therefore expected to be present in very high concentrations compared to, for example, breast epithelial cell surface antigens or intracellular antigens that are not secreted.

The following examples are offered by way of illustration, not by way of limitation.

EXAMPLE 1

Induction of Mammary Fluid Expression by Application of a Novel Breast Pump/Mammary Fluid Sample Collection Device Within the present example, a hand-held breast pump device 10' is employed to collect a primary sample of mammary fluid components comprising whole cells and cell fragments for cytological examination. The doctor, technician or patient collects the breast fluid specimen by grasping and operating the hand-held pump as described above to stimulate expression of the mammary fluid and collect a specimen thereof. This operation is a one-handed procedure, leaving the physician or technician free to conduct additional activities with the other, free hand. In this regard, the compact hand-held pump design allows the device to be picked up and manipulated with one hand, to seat the breast engaging element against the breast, apply sufficient vacuum pressure to the breast by manual operation of the vacuum pump to cause a suitable volume of breast fluid to be expressed at or near the nipple, and to simultaneously collect at least a primary sample of expressed breast fluid onto, or within, the solid phase sample collection medium (e.g., a nitrocellulose filter) without additional manual steps or the need to remove the device from the breast or engage two hands in the operation.

In the present example, the hand-held pump device 10' is employed to collect a primary sample of a selected mammary fluid component comprising cells and other cellular materials, that are retained (e.g., by retaining cells on a nitrocellulose membrane 39 or filter 40 coupled with the breast engaging member 14 or sample collection housing 30) for further processing. The primary collected sample of cells and other materials is then transferred (e.g., by washing or manual transfer) to a reservoir or other solid phase template, for further storage, processing and/or analysis. In more specific protocols, whole cells are separated from expressed mammary fluid onto a nitrocellulose membrane 39 or a filter 40 secured in fluid connection with the breast engaging member 14 a removable support member 56 mounted to the engaging member or sample collection housing 30.

The cells are subsequently transferred or washed in fluid (e.g., cytology fluid) to a second solid phase sample collection medium (e.g., a slide, well, tube or vial), which may also be connected to, or integrated with, the breast engaging member 14 or sample collection housing 30 as described above. In one protocol, the breast engaging member is removed from the breast and a jet of cytological fluid is directed against the filter on which the cells are retained. This flushes the cells off of the filter into an awaiting reservoir, typically a removable fluid-retaining reservoir. In this regard, uniquely designed membranes and filters are provided for use within this protocol which feature perforations or slits that disrupt the planar surface of the membrane or filter to facilitate air passage therethrough, to impart structural flexibility against mechanical perturbation, and to allow cells flushed from a first side (facing the breast) of the filter to a second side (facing internally, e.g., toward the sample collection housing, when the filter is mounted with the device) for secondary sample collection. For example, radial slits 280, spiral perforations 284 or transverse slits can be made in the filter to allow passage of air and for cells partitioned onto the first surface of the membrane to be flushed through the membrane into the removable, fluid-retaining reservoir 288 seated in the sample collection housing 30, for storage, shipment, and/or further processing directed toward cytological examination of the secondary collected sample.

EXAMPLE 2

Cytology in Biological Samples From Mammary Fluid

This example describes the use of conventional cytological techniques to identify and classify breast diseases from samples obtained as described in Example 1. Following collection of the sample, e.g., in a fluid-retaining reservoir member, the sample may be further processed (e.g., by centrifugation wherein the reservoir member is in the form of a modified cytology vial). Processed samples are then transferred to the central region of a clean glass microscopic slide, and a cover slip is slid over the sample to spread it along the surface of the slide. The slide is allowed to air dry and then is fixed, for example in absolute alcohol, and stained with standard cytological stains, such as methylene blue, hematoxyln and eosin, and other suitable stains.

The slides are then examined by light microscopy for evidence of atypical growth of cells and clumps of cells, using well known methods, including those described in *Diagnosis of Non-Palpable Breast Lesions: Ultrasonographically Controlled Fine-Needle Aspiration: Diagnostic and Prognostic Implications of Cytology* by Jacqueline Mouriquand, S. Karger Pub., July 1993; *Breast: Guides to Clinical Aspiration Biopsy* by Tilde S. and Irwin K. Kline, Igaku-Shoin Medical Pub., May 1988; *Cytopathology of the Breast* (*Asop Theory and Practice of Cytopathology* 5 by Shahla Masood, American Society of Clinical Pathology, November 1995; *Fine Needle Aspiration Cytology and Its Clinical Applications: Breast and Lung* by Philip S. Feldman, American Society of Clinical Pathology, November 1984; each incorporated herein by reference in its entirety.

EXAMPLE 3

Stimulation of Mammary Fluid Expression for Sample Collection by Coordinate Administration of Intranasal Oxytocin in Conjunction with Application of a Novel Breast Pump/Mammary Fluid Sample Collection Device The foregoing sample collection protocol in Example 1, as well as other sample collection methods within the invention, may be practiced solely by the use of a novel breast pump 10, 10' of the invention. Alternatively, these sample collection procedures may be practiced in conjunction with the use of oxytocin or oxytocin analogs to facilitate or increase mammary fluid expression induced by operation of the breast pump. As incorporated within the invention, these methods involve application of the breast pump 10, 10' to the breast, optionally coupled with oxytocin administration in amounts effective to facilitate mammary fluid expression in the patient. After the sample is collected, a bioassay is conducted on the sample to determine the presence and/or amount of a selected breast disease marker, preferably a breast cancer marker or panel of breast cancer markers, in the sample.

Oxytocin nasal solution acts specifically on the myoepithelial elements surrounding the alveoli of the breast and making up the walls of the lactiferous ducts, causing their smooth muscle fibers to contract and thus force any fluids present into the large ducts or sinuses where it can be expressed from the nipple by the further action of a breast pump. The nasal spray is promptly absorbed by the nasal mucosa to enter the systemic circulation. Intranasal application of the spray preparation is a practical and effective method of administration. Half-life of oxytocin in the human circulation is extremely short, approximately 10–15 minutes, and oxytocin is then rapidly removed from plasma by the kidney, liver, and mammary gland.

Because of the known effects of oxytocin to cause uterine contractions, pregnant women should not be treated by the methods contained herein unless the benefits of testing outweigh the risk of inducing premature labor.

The oxytocin nasal solution contains a concentration of natural or synthetic oxytocin, or a functional analog thereof such as carbetocin, that is intranasally effective in a selected volume of administered spray to stimulate expression of mammary fluid from a nipple of the patient when a breast pump is applied to the nipple to assist mammary fluid expression. In the present example, a preferred oxytocin preparation containing approximately 40 USP units of oxytocin per ml of lactated Ringer's solution is administered into the nose with the squeeze bottle held in the upright position while the patient is in a sitting position. One or two sprays are administered into each nostril from a standard nasal squeeze bottle, which delivers approximately 0.5 ml of the oxytocin solution per spray in a fine mist when the bottle is squeezed. The number and volume of sprays administered, as well as the concentration of oxytocin in the solution, can be adjusted according to well known pharmacokinetic principles (See for example, Newton, *Ann. N.Y. Acad. Sci.* 652:481–483; Mena, *Neuroendocrinology* 61:722–730, 1995; Gonser, *Arch. Gynecol. Obstet.* 256:63–66, 1995; Orhue, *Obstet. Gynecol.* 83:229–233, 1994; Satin et al., *Am. J. Obstet. Gynecol.* 166:1260–1261, 1992; and Satin et al., *Obstet. Gynecol.* 83:234–238, 1994, each incorporated herein by reference in its entirety) to ensure that the amount of oxytocin administered to the patient corresponds to an intranasally effective amount to stimulate the expression of at least 3 µl of mammary fluid in at least 50% of non-lactating female patients upon activation of the breast pump. For example, adjustments may be desired in the number of sprays delivered to the patient, and/or the timing of spray delivery, so that the clinician can modulate the dosage to each patient's varying sensitivity, and thereby minimize potential adverse side effects. In the present example, a preliminary dose of a single spray of the 40 Unit/ml oxytocin solution is delivered into each nostril of the patient, and the administering clinician waits for a short post-administration period of 2–3 minutes. After this period the breast pump is applied, and the clinician determines whether or not the amount of oxytocin delivered was sufficient to facilitate or increase breast pump-induced expression of mammary fluid. If additional fluid expression is desired at this stage a booster dose of 1 or 2 additional sprays of the oxytocin solution can be administered in each nostril, and the pump reapplied after a 5–10 minute post-booster administration period.

After the intranasally effective dose of the oxytocin is administered and the clinician has allowed a suitable post-administration period to elapse for the oxytocin to reach and stimulate the target alveolar-ductal tissue, the breast pump is applied. Negative pressures of 50–200 mm Hg are applied in the area of the nipple and are maintained, intermittently or continuously, for approximately 1–15 minutes, depending on the sensitivity of individual patients, oxytocin dosage and other factors. Alternatively, oxytocin can be administered by intramuscular or intravascular routes by well known means (Oxytocin Injection (synthetic), USP; Wyeth-Ayerst Laboratories) to effect the same response as intranasal administration.

EXAMPLE 4

Verification of Sample Quantity, Origin and Quality

Using either of the above methods of Example 1 or Example 3, volumes of at least 3 µl of expressed mammary fluid can be collected in a substantial population of non-lactating female patients. During or after the mammary fluid expression step, a biological sample is collected from the expressed mammary fluid as described above. For example, a nitrocellulose filter may be placed within the breast pump in line with a path of the expressed mammary fluid into the pump, so that the expressed fluid contacts the filter. Upon contact of the primary sample of expressed mammary fluid with the filter, cells, proteins and other desired components of the mammary fluid adhere to the filter to form a filter-bound or filter-retained biological sample for subsequent analysis. Other suitable biological samples, including whole mammary fluid samples, cytological samples of whole cells, membranes or other cellular components, and samples containing proteins, glycoproteins, peptides, nucleotides and other constituents of the primary mammary fluid sample can be collected with appropriate modifications of the above procedures, according to well known principles and methods.

To ascertain that the sample of mammary fluid is of mammary origin and is not corrupted by likely contaminants, one or more constituents of normal mammary fluid are assayed for. In the present example, an enzyme that is ordinarily present in mammary fluid, lysozyme, is assayed in the mammary fluid sample to help confirm that the sample is of mammary origin. Lysozyme (muramidase) is an enzyme which hydrolyzes beta 1,4-glycosidic linkages in the mucopolysaccharide cell wall of a variety of microorganisms, which activity can be readily detected and quantified using a routine, inexpensive assay. In the present example, Lysozyme is measured in the primary mammary fluid sample using the Quantiplate Lysozyme Test kit (Kallestad, Chasta, Minn.). The assay employs the reagents and procedures provided by the manufacturer and specified in detail in the manufacturer's instructions, with the exception that a mammary fluid sample is substituted in place of serum, urine or tears. Analysis of these results establishes that the sample contains lysozyme, which is a normal component of human serum, urine, saliva, tears, nasal secretions, vaginal secretions, seminal fluid, and mammary fluid.

More specific assays are used in place of the lysozyme assay, or to supplement lysozyme assay results, particularly where clinical data for human patients are being gathered. Other mammary fluid markers for sample verification that are more specific than lysozyme can be readily incorporated within the invention, based on published and generally known information. In one example, the presence of cathepsin D is assayed using the monoclonal antibodies and methods disclosed in Vetvicka et al., *Biochem. Mol. Biol. Int'l.* 30:921–928, 1993, incorporated herein by reference in its entirety). In another example, one or more human mammary epithelial antigens (HME-Ags) corresponding to glycoprotein components of the human milk fat globulin (HMFG) protein are detected in the primary mammary fluid sample, or in the biological sample that is used in the breast cancer marker assay, using specific antibody probes, as described by Rosner et al., *Cancer Invest.* 13:573–582, 1995; Ceriani et al., *Proc. Natl. Acad. Sci. USA* 74:582–586, 1982; Ceriani et al., *Breast Cancer Res. Treat.* 15:161–174, 1990, each incorporated herein by reference in its entirety). In many cases, the sample verification assay can be incorporated within the breast cancer marker assay in a single procedure, for example as described below in Example 4, an assay for HME-Ags (wherein the HME-Ag findings are indicative of sample origin/quality, and also of the presence and/or quantity of a specific breast cancer marker in the sample). In another example, sample verification is achieved through a combinatorial (i.e. multiple marker) immunoassay targeting various cytokeratins, which can be detected as a panel of cytokeratins specifically expressed in mammary tissue sample. (See, Nagle, J., *Histochem. Cytochem.* 34:869–881, 1986, incorporated herein by reference in its entirety). One or more of these cytokeratins (e.g. K5, K8, K18 and K19) can be simultaneously or independently measured in the context of a breast cancer assay, and the level of expression of the subject cytokeratin(s) can yield information concerning the presence or status of breast cancer in a patient. (See for example, Focus, Harvard University News Office, Mar. 21, 1991, pp. 2–3; and Lee, *Proc. Natl. Acad. Sci. USA* 88:1991, each incorporated herein by reference in its entirety).

EXAMPLE 5

Immunoassay for Human Mammary Epithelial Antigens in Biological Samples From Mammary Fluid Human mammary epithelial antigens (HME-Ags) are glycoprotein components of the human milkfat globule (HMFG) and of the membrane of the breast epithelial cell, which are released by breast tumors and not by normal breast tissue. (Ceriani et al., *Proc. Natl. Acad. Sci. USA* 74:582–586, 1977, incorporated herein by reference in its entirety). In the present example, several HME-Ags, having molecular weights of 150, 70, and 45 kilodaltons, are detected and measured using specific anti-HMFG or anti-human mammary epithelial ($\alpha$-HME) probes prepared and employed as described by Ceriani et al., *Proc. Natl. Acad. Sci. USA* 79:5420–5425, 1982 (incorporated herein by reference in its entirety).

To begin the assay, biological samples from mammary fluid collected on nitrocellulose filters coupled with a breast pump 10, 10' as generally described above are eluted electrophoretically into phosphate buffered saline to provide a test sample, according to standard methods. Alternatively, whole mammary fluid or other types of biological samples obtained from mammary fluid can be constituted in an appropriate medium or mixture to provide a test sample for the assay. Once the test sample is thus provided, it is then assayed according to the HME-Ags radioimmunoassay (RIA) methods described in Ceriani et al., *Breast Cancer Res. Treat.* 15:161–174, 1990 (incorporated herein by reference in its entirety).

Briefly, the RIA includes two preliminary treatments of the biological samples to separate interfering factors: a centrifugation step to separate out any fat present, and a second, precipitation step to precipitate potential immuno-complexes using polyethyleneglycol (PEG). The next steps comprise the assay proper, where HMFG antigen bound to a solid support (microtiter plates) is presented to stoichiometric or lesser amount of the $\alpha$-HME antibody probe, and binding of the $\alpha$-HME is competed by the biological samples from mammary fluid preliminarily treated as above. The amount of $\alpha$-HME bound to HMFG antigen on the solid phase is determined in a final step by detection of the $\alpha$-HME antibody probe by radioiodinated, affinity-purified rabbit anti-mouse immunoglobulin.

Solutions used in the assay are as follows: i) Phosphate buffered saline (PBS): 176 ml 0.05M $KH_2PO_4$, 608 ml 0.05M $Na_2HPO_4$, and 8 g NaCl brought up to 1000 ml in $H_2O$ (pH 7.4). ii) RIA buffer: 0.1% BSA, in 0.3% Triton-X-100 (Research Prod. International Corp., Mount Prospect, Ill.) plus 0.05% sodium azide in PBS. iii) Detergent buffer:

0.3% Triton-X-100 plus 0.05% sodium azide in PBS. iv) Buffered polyethylene glycol (PEG): 6.6% PEG (M.W. 8000) (Sigma) plus 0.05% sodium azide in PBS) $^{125}$I-labeled affinity-purified rabbit anti-mouse immunoglobulin (Rα-mouse Ig) (Antibodies, Inc., Davis, Calif.), radioiodinated by the chloramine-T procedure as reported (Ceriani et al., *Proc. Natl. Acad. Sci. USA* 79:5420–5425, 1982) and diluted to $4 \times 10^6$ cpm/ml, in RIA buffer. Rabbit polyclonal anti-HMFG antibodies or rabbit anti-human mammary epithelial antibodies (α-HME) were prepared and assayed as described (Id.).

To prepare a standard curve for evaluating assay results, control samples from normal human mammary fluid (exposed to nitrocellulose filters and eluted in the same manner as the nitrocellulose adsorbed, eluted test sample, or alternatively provided as normal whole mammary fluid or other selected type of sample obtained from normal mammary fluid, constituted in an appropriate medium or mixture to provide a suitable control assay sample) are centrifuged for 7 min at 10,240 rpm at 10° C. The upper white band formed at the top of the sample (if there is one) is discarded. Fresh 100 µg protein/ml solution of lyophilized dilipidated HMFG (Ceriani et al., *Proc. Natl. Acad. Sci. USA* 74:582–586, 1977) in detergent buffer is prepared and sonicated at 10 second intervals for a total of 4 minutes (10 sec. of sonication, followed by a 10 sec. silent period) using a double step micro tip horn at 25 watts on a Sonifier Cell Disrupter 185 (Branson, Danbury, Conn.) at 4° C. HMFG solutions at concentrations of 0, 10, 33.3, 100, 333.3, and 1000 ng protein/ml are prepared in spun female sera, and 3 aliquots of 180 µl of each HMFG level in normal female sera are pipetted into 400 µl polyethylene microcentrifuge tubes (West Coast Sci. Emeryville, Calif.). 150 µl of 6.6% PEG solution is added to each microcentrifuge tube, and the tubes are incubated overnight on a rotating shaker at room temperature.

Test samples are processed in a comparable manner, by centrifuging 300–350 µl of the eluted nitrocellulose filtrate in solution (or, alternatively, of mammary fluid or other assay sample alternative) in a 400 µl microcentrifuge tube for 5–7 min. at 10,240 rpm at 10° C. The microcentrifuge tubes are then cut with a razor blade below the white band formed by the sera (if there was one) and 180 µl of remaining sera is transferred to a new microcentrifuge tube. 150 µl of a 6.6% PEG solution is then added to each microcentrifuge tube, and the tubes are incubated overnight on a rotating shaker at room temperature.

Day Two (1) α-HME is diluted to its appropriate concentration in detergent buffer. The antibody solution has stoichiometric or lesser amounts of α-HME to 6 ng HMFG protein equivalent (prot. eq.). Six ng of HMFG is covalently bound to microtiter plates by the methylated BSA procedure previously described by Ceriani, in *Monoclonal Antibodies and Functional Cell Lines*, pp. 398–402, Kennet et al. (eds), Plenum Press, New York, 1984, incorporated herein by reference in its entirety.

(2) To process test samples and control samples on the second day, microcentrifuge tubes are centrifuged for 7 min. at 10,240 rpm at 10° C. in a SHMT rotor with a Sorvall RC5C centrifuge. In triplicate, 55 µl of supernatant is pipetted into empty microtiter plate wells (Dynatech, Alexandria, Va.), and any precipitate pelleted is left undisturbed. 25 µl of 6.6% PEG solution is added to each well. 30 µl of α-HME diluted in detergent buffer is also added to each well, and a non-porous Scotch® tape is placed over the wells to avoid evaporation. The microtiter plate is then incubated overnight at room temperature on a rotary shaker.

Day Three

The microtiter plates are centrifuged (3000 r.p.m.) for 30 minutes at room temperature to decant suspended perceptible matter. 50 µl of RIA buffer is added to wells of microtiter plates containing 6 ng HMFG and aspirated off after 5 minutes.

The total contents of microtiter plates from 1), save for any precipitation induced by the PEG and already pelleted, are carefully transferred to the wells of another set of microtiter plates containing 6 ng HMFG per well (Day 2,1), above.

The microtiter plates are incubated for 3 hours with rotating agitation at room temperature. The plates are washed 5 times with RIA buffer using Dynadrop SR-1 automatic dispenser form Dynatech. 50 µl of the radioiodinated affinity-purified rabbit anti-mouse immunoglobulin diluted in RIA buffer is then adder per well. The plate is covered with tape and incubated with rotating agitation for 2 hours at room temperature. The plate is washed 5 times with RIA buffer. Wells are cut and counted in a gamma counter.

The results of these assays will yield important information concerning the presence and/or status of cancer in patients, comparable in scope and value to the data provided by serum assays conducted for the HME-Ag breast cancer marker by Ceriani et al., *Breast Cancer Res. Treat.* 15:161–174, 1990. By selecting patient and control samples and developing and evaluating comparative data according to the procedures followed by Ceriani and his coworkers, the assay methods of the invention will also be readily adapted for use in direct clinical applications to determine both prognostic and treatment related variables in breast cancer patients. Reagents and conditions for the assays can of course be substituted or adjusted depending on a variety of anticipated variables, by applying well known immunological methods and principles.

EXAMPLE 6

Competitive Radioimmunoassay for Non-Penetrating Glycoprotein in Biological Samples From Mammary Fluid This competitive radioimmunoassay is based on the displacement by breast epithelial antigens contained in biological samples from mammary fluid obtained according to the methods of the invention of the binding of stoichiometric or lesser quantities of the monoclonal antibody Mc5 to a solid-phase-bound antigen known as non-penetrating glycoprotein (NPGP) contained in HMFG. HMFG is bound to a solid support and exposed to the Mc5 antibody during an incubation period allowing the antibody to bind the NPGP antigen in solid phase-bound HMFG. The presence and/or level of NPGP in the biological sample is ultimately examined by ability of the sample to compete for Mc5 binding to the NPGP antigen in the solid phase-bound HMFG, as detected and/or measured using a radiolabeled goat anti-mouse antibody to bind and label the Mc5 antibody probe.

Buffer and other solutions and reagents in this example are generally the same as those used for the HME-Ags polyclonal antibody radioimmunoassay described in Example 4, above. To provide test samples for the assay, biological samples from mammary fluid contained on nitrocellulose filters are eluted electrophoretically into phosphate buffered saline, according to standard methods. Alternatively, whole mammary fluid or other types of biological samples obtained from mammary fluid can be constituted in an appropriate medium or mixture to provide a test sample for the assay. Once the test sample is thus provided, it is then assayed according to the NPGP/Mc5 radioimmunoassay (RIA) methods described in Ceriani et al., *Breast Cancer Res. Treat.* 15:161–174, 1990 (incorporated herein by reference in its entirety), as follows:

400 µl of pooled normal female mammary fluid (exposed to nitrocellulose filters and eluted in the same manner as the nitrocellulose adsorbed, eluted test sample, or alternatively provided as normal whole mammary fluid or other types of biological samples obtained from normal mammary fluid constituted in an appropriate medium or mixture to provide a test sample) to provide a suitable control sample, which is diluted to 2.4 ml using RIA buffer at a 1:6 concentration.

A 500 µg/ml solution of lypholized HMFG is prepared in 1×PBS with 0.3% Triton-X-100, 0.05% sodium azide, and sonicated using a double step micro tip horn at 25 watts on a Sonifier Cell Disrupter 185 (Branson, Danbury, Conn.) for 4 minutes (10 sec. sonication, 10 sec. silent period, at 4° C.).

Solutions to prepare a standard curve are prepared using the 2.4 ml 1:6 normal female serum and increasing amounts of HMFG (0, 0.25, 2.5, 25, 50 µg/ml HMFG, as described above in Example 4).

Each test assay sample is diluted 1:6 with RIA buffer (40 µl of serum to 200 µl RIA buffer) to form a diluted test assay sample, and vortexed.

Mc5 stock solution is prepared so that it contains less than stoichiometric amounts of antibody to 100 ng protein/well of HMFG covalently bound to microtiter plates prepared as previously described by Ceriani, in *Monoclonal Antibodies and Functional Cell Lines*, pp. 398–402, Kennet et al. (eds), Plenum Press, New York, 1984, incorporated herein by reference in its entirety.

200 µl RIA buffer are added to each well of 100 ng HMFG and then aspirated after 5 minutes.

To prepare a standard curve, 30 µl of HMFG standardizing solutions (as in 3 above) are added in quadruplicate to a 100 ng protein/well HMFG microtiter well.

30 µl of diluted test assay sample (or, alternatively, of mammary fluid or other assay sample alternative) are added in triplicate to 100 ng/well HMFG microtiter wells.

To each well 20 µl of the Mc5 stock solution is added.

Microtiter plates are covered with nonporous Scotch® tape and incubated overnight at room temperature on a rotating agitator.

The next day the wells are aspirated and washed 5 times with RIA buffer.

To each well 50 µl of 200,000 cpm/50 µl $^{125}$I-goat anti-mouse antibody are dispensed. The wells are covered with nonporous tape and placed on a rotating agitator for 3 hours at room temperature.

Wells are washed 5 times with RIA buffer.

Each well is cut and the radioactivity is counted using a gamma counter.

The results of these assays will yield important information concerning the presence and/or status of cancer in patients, comparable in scope and value to the data provided by serum assays conducted for the NPGP breast cancer marker by Ceriani et al., *Breast Cancer Res. Treat.* 15:161–174, 1990. By selecting patient and control samples and developing and evaluating data according to the well known procedures followed by Ceriani and his coworkers, the assay methods of the invention will be readily adapted for use in direct clinical applications to determine both prognostic and treatment related variables in breast cancer patients. As will be understood by those skilled in the art, reagents and conditions for the assays can be substituted or adjusted depending on a variety of anticipated variables, according to well known immunological methods and principles.

EXAMPLE 7

Solid Phase Immunoassay for Mucinous Carcinoma Associated Antigen in Mammary Fluid This example uses a sensitive, solid phase immunoassay to detect the mucinous carcinoma associated antigen (MCA) in biological samples from mammary fluid obtained according to the methods of the invention. MCA concentrations are determined using an antibody-bead immunoassay kit provided by Hoffman-La Roche (Basel, Switzerland), and using the reagents and procedures provided by the manufacturer and described in further detail in Eskelinen et al., *Anticancer Res.* 9:437–440, 1989. Briefly, test assay samples of whole mammary fluid and standards are first incubated with MCA monoclonal antibody beads and then, after appropriate washings, enzyme (horseradish peroxidase) labeled secondary antibody is added. During the second incubation the anti-MCA enzyme conjugates are attached to the antibody antigen complex on the beads. Excess conjugates are removed by washing and, finally, enzyme substrate is added and the color formed is recorded.

The solid phase assay format presented in this example can be adapted for use in a wide array of other assays to detect and/or measure other cancer markers besides the MCA marker, with enhanced sensitivity. In addition, the results of these assays can be evaluated along with those of complementary assays detecting and/or measuring different markers to yield more precise information concerning the presence and/or status of cancer in patients, as exemplified by the combinatorial MCA/CA 15-3 assays described by Eskelinen et al., *Anticancer Res.* 9:437–440, 1989; see also Eskelinen et al., *Anticancer Res.* 8:665–668, 1988, each incorporated herein by reference in its entirety.

EXAMPLE 8

Western Analysis of Proteins From Cellular Fractions of Human Mammary Fluid Using Polyclonal and Monoclonal Antibody Probes to Detect Vasopressin A variety of assays are provided by the present invention that focus on cellular samples from human mammary fluid. In general, these assays rely on isolation by standard separation methods (e.g. centrifugation, sucrose gradient, etc.) of cells, membranes or other cell components from whole mammary fluid expressed according to the above methods. Biological samples containing whole cells from expressed mammary fluid are particularly useful for cytological and cytochemical examination to detect and evaluate breast cancer in patients. Biological samples containing purified cell membrane fractions from human mammary fluid are particularly useful in this context, for example to detect and/or measure breast cancer markers that are expressed by alveolar-ductal cells as intracellular or membrane bound proteins and are therefore not as readily detected in liquid fractions of mammary fluid as secreted proteins.

The present example focuses on assays for detecting the peptide hormone vasopressin in biological samples from mammary fluid, using methods adapted from North et al., *Breast Cancer Res. Treat.* 34:229–235, 1995. Specifically, this assay uses a test sample of crude protein isolated from a pooled sample of cells obtained from expressed mammary fluid. The cells are separated from whole mammary fluid according to standard methods, and crude protein is extracted from the cells by sonication in 100 volumes of 0.1 M HCl. The resulting protein suspensions are then centrifuged at 1500×g for 10 min. at ambient temperature, and soluble protein is precipitated with 40% TCA. This protein is pelleted by centrifugation at 10,000×g for 2 min. TCA is then removed from pellets by washing (×2) with ether. Protein is resuspended in 0.1 M Tris HCl (pH 8.7), reduced with mercaptoethanol at 100° C. for 5 min. (and in some cases S-alkylated with N-ethyl maleimide), and subjected to SDS-PAGE electrophoresis on 15% gels at pH 9.3 using the method of Laemeli, *Nature* 227:680–685, 1970, incorporated herein by reference in its entirety. Separated proteins are then electrophoretically transferred with 20 mM Tris glycine (pH 8.0) to Immobilon PVDF membranes (Millipore, Bedford, Mass.). These membranes are blocked with a 5% non-fat milk solution, washed (1×15 min., 2×5 min.) with PBS containing 0.5% Triton, and incubated with preparations of mouse monoclonal antibody to VP-HNP, with rabbit polyclonal antibodies to VP, with rabbit polyclonal antibodies to VAG, or with ubiquitous mouse or rabbit IgG (negative controls) (for description of antibodies and antibody preparation see North et al., *Breast Cancer Res. Treat.* 34:229–235, 1995, incorporated herein by reference in its entirety), for 1 h at ambient temperature. Following a second wash in PBS-Triton (1×15 min., 2×5 min.), the membranes are treated, respectively, with goat anti-mouse IgG-horseradish peroxidase conjugate or goat anti-rabbit IgG-horseradish peroxidase conjugate for 1 h, and then washed with PBS-Triton (1×15 min., 4×5 min.). Immunoreactive proteins are visualized using an ECL Western Blotting Detection System with exposure of x-ray film from 10 seconds to 5 min. Prestained SDS-PAGE standard proteins are employed as molecular size markers.

Recent studies suggest that vasopressin is universally expressed in breast carcinoma and is absent from normal breast cells. North et al., *Breast Cancer Res. Treat.* 34:229–235, 1995. These and other results indicate that vasopressin and its relatives are important breast cancer markers that can be readily detected using immunological assays of proteins isolated from breast tumor cells. Accordingly, the results of the present example using cell samples isolated from human mammary fluid are also expected to yield important information concerning the presence and/or status of cancer in patients.

EXAMPLE 9

Quantification of Carcinoembryonic Antigen in Biological Samples From Mammary Fluid by Dot Immunoblotting Assay Among the more sensitive assays of the invention, useful for measuring low levels of breast cancer markers and for detecting markers when only small volumes of expressed mammary fluid are available, is the dot immunoblotting assay. In the present example, carcinoembryonic antigen (CEA) is measured in whole mammary fluid using an Elmotech anti-CEA monoclonal antibody kit (Mochid Pharmaceutical Co., Tokyo, Japan) in a dot blot assay format. Briefly, anti-CEA monoclonal antibody is diluted to appropriate concentrations and coated on the plastic film. Aliquots (5 $\mu$l) of either standard CEA solution (0, 100, 200, and 500 ng/ml), or of the whole mammary fluid assay sample, are smeared on the immobilized film. Assay standards are prepared from purified antigen preparations, in accordance with the Elmotec kit manufacturer's instructions. If necessary, 1000 ng/ml CEA solution is also used as a standard. After drying at room temperature, the film is exposed to peroxidase-conjugated anti-CEA antibody for 20 min at room temperature. The film is then washed extensively with 1 M saline containing 0.5% (v/v) Tween 20. The enzyme reaction is visualized using tetramethylbenzidine as a chromogen. The developing solution consists of 0.05 mM tetramethylbenzidine and 0.01% hydrogen peroxide in McIlvain buffer (0.1% M phosphate-citrate buffer), pH 5.0, containing 10% methanol. The concentration of CEA in the mammary fluid assay sample is determined by comparing the color intensities with a corresponding standard.

The assay disclosed in the present example, and related assays incorporating antibodies to other tumor markers besides CEA, are particularly useful for measuring low levels of breast cancer markers and for detecting markers in limited sample volumes. The results of these assays will yield important information to determine both prognostic and treatment related variables in breast cancer patients. As will be understood by those skilled in the art, reagents and conditions for the assays can be substituted or adjusted depending on a variety of anticipated variables, according to well known immunological methods and principles.

EXAMPLE 10

Detection of Procathepsin D and Cathepsin D Activity in Biological Samples From Mammary Fluid Cathepsin D is a lysosomal aspartic proteinase that has been studied intensively as a marker for cancer processes necessary for metastasis. In the present example, polyclonal antibodies against procathepsin D are used to immunoprecipitate and immunochemically detect proteins from whole mammary fluid or cell lysates from mammary fluid, generally according to the methods disclosed in Vetvicka et al., *Biochem. Mol. Biol. Int'l.* 30:921–928, 1993 (incorporated herein by reference in its entirety). Alternatively, or as a complementary assay, the protease activity of cathepsin D is detected, also according to the methods disclosed in Vetvicka et al. (Id.). Briefly, pooled whole mammary fluid (preferably 3 ml if available) is diluted with 3 ml of buffer A (50 mM Tris.HCl, 5 mM $CaCl_2$, 1 mM $MgCl_2$, 500 mM NaCl pH 7.2). The suspension is centrifuged for 30 minutes at 10,000 g. The resulting water phase is centrifuged again under the same conditions. The soluble part (total of approximately 4.5 ml) is loaded on a 1 ml column of Concanavalin A Sepharose (Pharmacia, Uppsala, Sweden) equilibrated in buffer A, and after washing with buffer A the retained proteins are eluted using 0.75 M methyl a-D-mannopyranoside. The fractions (250 $\mu$l) are analyzed for cathepsin D activity using the $^{14}C$ hemoglobin assay as described by Lin et al., *J. Biol. Chem.* 264:4482–4489, 1989 (incorporated herein by reference in its entirety), by western blots and by silver-stained electrophoresis. The inhibition of human milk procathepsin D is accomplished by adding 2 $\mu$l of 1 mM pep statin A (Boehringer Manheim, Germany) dissolved in methanol to the reaction mixture.

This assay provides but one example of many possible embodiments of the invention that incorporate known biochemical assays, in addition to, or supplemental to immunological assays, to evaluate biological samples from mammary fluid to determine cancer related variables. The fundamental methods provided herein for obtaining samples from human mammary fluid render these assays readily adaptable for widespread clinical application to detect and/or measure the activity of a subject breast cancer marker within a non-invasive screening protocol.

Those with ordinary skill in the art will appreciate that other embodiments and variations of the invention are possible which employ the same inventive concepts described above. Most particularly, a wide and rapidly expanding array of useful breast cancer markers (including proteins, DNA and RNA sequences and other markers) and probes (including immunological, nucleotide and biochemical probes) are readily available for adaptation and use within the methods and kits of the invention. These markers and probes are described or referenced to a large extent in the literature cited and incorporated within the present disclosure, or are elsewhere published in the literature or well known in the art. Among these known and emerging markers and probes, useful examples within the invention include Her 2 (also known as erbB-2 and neu). Her 2 is a transmembrane glycoprotein growth factor receptor of the EGF receptor family encoded by a gene located on chromosome 17q, a region of frequent amplification in breast cancer cell lines. This marker is highly predictive of breast cancer and can be detected in cellular samples of the invention using known nucleotide probes to detect genetic defects in Her 2, or to detect and/or measure mRNA to determine overexpression of Her 2 linked to increased proliferation of cancer cells. (See for example, Visscher et al., In Weinstein and Graham (eds) Advances in Pathology and Laboratory Medicine, vol. 5, St. Louis, Mosby Yuear Book, 1992, pp. 123–161; Barbareschi et al., *Am. J. Clin. Pathol.* 98:408–418, 1992; Slamon et al., *Science* 235:177–182, 1987; each incorporated herein by reference in its entirety). Protein levels of Her 2 are also readily detected using available immunological probes. (For review see Porter-Jordan et al., *Hematol. Oncol. Clin. North Amer.* 8:73–100, 1994 and articles cited on page 80 therein, each incorporated herein by reference in its entirety). Additional markers for use within the invention include EGF and the EGF receptor, for which immunological and non-immunological probes and assay methods readily adaptable within the invention are characterized in detail at page 80–81 of Porter-Jordan et al., *Hematol. Oncol. Clin. North Amer.* 8:73–100, 1994 and in the references cited therein, each incorporated herein by reference in its entirety. Additional examples of proliferation markers, growth factors and receptors, proteases, adhesion factors, angiogenic factors, oncogenes and tumor suppressor genes that provide useful breast disease markers and probes within the methods and kits of the invention include Ki67 Growth Factor, Cyclin D1, Proliferating Cell Nuclear Antigen, Transforming Growth Factor, Tissue Plasminogen Activator, Insulin Growth Factor Receptors, Collagenase Type IV, Laminin Receptor, Integrins, p53, rb, nm23, ras, c-myc, c-myb, Heat Shock Proteins, Prolactin, Neuron-Specific Enolase, IR-14, KA 1, KA 14, Alpha-Lactalbumin, Actin, IL-10, S-100 protein, Vimentin, Epithelial Membrane Antigen, bcl-2, CA15-3, CA 19-9, In Antigen, Alpha-lactalbumin, LASA, Gal-GalNAC, GCDFP-15, Le(y)-Related Carbohydrate Antigen, CA 125, uPA, uPA related antigens and complexes, uPA Receptor, PAl-1 and PAl-2, Beta-glucuronidase, CD31, CD44 splice variants, blood group antigens including ABH, Lewis, and MN, and genetic lesions or altered expression levels of CCND1, EMS 1, BRCA1 and BRCA2 genes, and many others, for which immunological and non-immunological binding partners, probes and assay methods are known and readily adaptable within the invention.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation.

What is claimed is:

1. A sample collection device for collecting a biological sample from a mammary organ of a patient, comprising:
    a breast engaging member constructed of a non-porous material sized and dimensioned to receive at least a nipple portion of a breast of said patient and form a suction seal therewith;
    a solid phase sample collection medium in fluid connection with said breast engaging member for receiving a sample of expressed breast fluid;
    vacuum pump means in gaseous connection with said breast engaging member for generating negative pressure through the breast engaging member to facilitate breast fluid expression; and
    a hand-held breast pump incorporating said breast engaging member and vacuum pump means in a compact, structurally integrated breast fluid collection apparatus that can be manipulated and operated with one hand, wherein the hand-held breast pump comprises a fluid-retaining well comprising an integral, defined compartment or enclosure within a sample collection housing for receipt of breast fluid and/or constituent samples thereof within a removable fluid reservoir member of the sample collection housing.

2. The sample collection device of claim 1, wherein the removable reservoir member is a rigid sample collection tube or vial removably connected with an outer casing member of the housing that partially or completely encloses the tube or vial.

3. The sample collection device of claim 1, wherein the removable reservoir member is a rigid sample collection tube removably, sealably connected with an outer casing member of the housing to form an airtight coupling therewith.

4. The sample collection device of claim 1, wherein the removable reservoir member is a cytology vial sealably connected with an outer casing member of the housing to form an airtight coupling therewith.

5. The sample collection device of claim 4, wherein the removable reservoir member and outer casing member of the housing are coupled to form an assembled sample collection housing, wherein the reservoir member is removably nested within the casing member to form a substantially airtight contact between an inner wall of the casing member and an outer wall of the reservoir member.

6. The sample collection device of claim 5, wherein an outer wall of the removable reservoir member features a circumferential O-ring that engages and makes a circumferential airtight seal against the inner wall of the casing member when the vial is nested within the casing member.

7. The sample collection device of claim 1, wherein the removable reservoir member is gaseously and fluidly connected with the breast engaging member to facilitate sample collection.

8. The sample collection device of claim 1, wherein vacuum pressure from the vacuum pump means is routed to the breast engaging member through the removable reservoir member of the housing.

9. The sample collection device of claim 8, wherein the removable reservoir member is modified to include one or more air ports that form a gaseous connection between a lumen of the reservoir member and the vacuum pump means.

10. The sample collection device of claim 1, wherein the removable reservoir member functions as both a conduit for vacuum pressure transmission to the breast and a receptacle for fluid sample.

11. The sample collection device of claim 1, further comprising a support member coupled with the breast engaging member, wherein the removable reservoir member communicates for fluid and gaseous transmission directly with the breast engaging member by way of air channels in a the support member.

12. The sample collection device of claim 1, wherein the solid phase sample collection medium fluidly connected with the breast engaging member is positioned to collect a primary sample of one or more breast fluid components which can thereafter be washed or otherwise transferred directly or indirectly into the removable reservoir member without removal or disassembly of the breast engaging member and reservoir member.

13. The sample collection device of claim 12, wherein the solid phase sample collection medium is a nitrocellulose membrane for retaining cells and other cytological materials on a surface of the membrane.

14. The sample collection device of claim 12, wherein the primary sample collection medium is supported in fluid connection with the breast engaging member by a support member, and wherein the support member includes one or more sample transfer channels for transfer of the primary sample from the primary sample collection medium, through the channels into the removable reservoir.

15. The sample collection device of claim 14, wherein the sample transfer channels extend through connection ports that extend from the support member toward, or into, a lumen of the fluid reservoir member.

16. The sample collection device of claim 1, wherein the removable reservoir member is a cytology vial having one or more air ports that communicate between an outer wall and inner lumen of the vial to form a gaseous connection between the lumen of the vial, the vacuum pump means, and the breast engaging member.

17. The sample collection device of claim 1, wherein the removable reservoir member further comprises closure means for closing the reservoir member after sample collection is completed to prevent sample contamination and spillage, whereby the removable reservoir member serves a multi-purpose function for sample collection as a component of the breast pump device as well as for storage, transport and/or processing of the sample upon removal of the reservoir member from the device.

18. The sample collection device of claim 17, wherein the closure means comprises a cap adapted to sealably engage a top end of the removable reservoir member.

19. The sample collection device of claim 17, wherein the reservoir member is modified to include one or more air ports that form a gaseous connection between a lumen of the reservoir member and the vacuum pump means when the reservoir member is engaged with the pump device, and wherein the closure means further comprises secondary closure means to sealably close the one or more air ports after sample collection.

20. The sample collection device of claim 19, wherein said secondary closure means comprise an adhesive seal or sticker sized and constructed to adhere to an outer wall of the reservoir member surrounding an air port opening.

21. The sample collection device of claim 19, wherein said secondary closure means comprises a combined closure and labeling device which functions as a secondary closure mechanism to seal the one or more air ports of the removable reservoir member and as a labeling template to provide a writing surface for sample labeling.

22. The sample collection device of claim 19, wherein said secondary closure means comprises a combined closure and labeling tab or sticker which is adapted to be directly applied to seal the one or more air ports after sample collection having a first, closure-forming surface for application over the air port to form a seal by juxtaposition or adhesive contact with an outer wall of the removable reservoir member, and a second, labeling surface opposite the closure-forming surface made of a blank template material suitable for receiving a stable, ink or graphite imprint thereon.

23. The sample collection device of claim 22, wherein said first, closure-forming surface bears an adhesive coating resistant to disruption by contact with aqueous solutions.

24. The sample collection device of claim 19, wherein said secondary closure means comprises a combined closure and labeling tab or sticker which is pre-attached to the removable reservoir member in a first, open configuration and is adapted to be manually repositioned after sample collection to a second, closed configuration to form a seal or closure against the one or more air ports.

25. The sample collection device of claim 24, wherein said secondary closure means comprises an adhesive tab or strip folded in the open configuration to form an inner layer affixed to the reservoir proximate to the air port and an outer layer folded over the inner layer, said outer layer providing a first, closure-forming surface and a second, labeling surface, wherein the outer layer can be unfolded away from the inner layer and wrapped around the reservoir member so that the closure-forming surface covers the one or more air ports to form a fluid-resistant closure and the labeling surface faces outward for recordation of sample data.

26. The sample collection device of claim 25, wherein the outer layer is optionally secured in a folded-back position against the inner layer by adhesive engagement of the labeling surface with the inner layer.

27. The sample collection device of claim 26, wherein said first, closure-forming surface bears an adhesive coating that is protected in the open configuration by folding of an end segment of the outer layer bearing the adhesive coating back, so that the closure forming surface provides a protective surface to shield the adhesive prior to closure, whereby the end segment is adapted to be lifted and pulled outward to unfold the end segment to separate the adhesive coating on the closure-forming surface from the protective surface and to release the outer layer from the inner layer for closing of the one or more air ports.

28. The sample collection device of claim 1, wherein the breast engaging member includes removable coupling means for removable coupling of the breast engaging member with a complementary coupling surface of the sample collection housing.

29. The sample collection device of claim 28, wherein the sample collection housing includes an outer casing member and a removable, fluid reservoir member, and wherein the breast engaging member is adapted to be directly coupled to the fluid reservoir member.

30. The sample collection device of claim 29, wherein the breast engaging member has coupling threads to engage complementary threads of an open end of the removable reservoir member, said complementary threads of the reservoir adapted to interchangeably receive a cap that sealably engages the reservoir member open end.

31. The sample collection device of claim 30, wherein the removable reservoir member is a modified cytology vial.

32. The sample collection device of claim 1, wherein the vacuum pump means comprises a vacuum pump actuating mechanism connected to a vacuum pump housing of the vacuum pump means, wherein the vacuum pump actuating mechanism comprises an actuating lever pivotally connected to the vacuum pump housing.

33. The sample collection device of claim 32, wherein the vacuum pump housing includes an integral handle opposing an actuating lever pivotally connected to a base portion of the handle.

34. The sample collection device of claim 1, wherein the vacuum pump means comprises a flexible diaphragm member and pump actuating means to draw the diaphragm member away from a primary vacuum chamber connected with, or integrated within, the sample collection housing.

35. The sample collection device of claim 34, further comprising a vacuum pump housing, wherein the primary vacuum chamber is integrally formed within the vacuum pump housing proximate the flexible diaphragm member and extends to a communicating port opening to the sample collection housing.

36. The sample collection device of claim 35, further comprising a removable fluid reservoir member of the sample collection housing modified to include one or more air ports that form a gaseous connection between a lumen of the reservoir member and the communication port to gaseously connect the lumen of the reservoir member to the primary vacuum chamber.

* * * * *

UNITED STATES PATENT AND TRADEMARK OFFICE
CERTIFICATE OF CORRECTION

PATENT NO. : 6,887,210 B2
DATED : November 8, 2005
INVENTOR(S) : Steven C. Quay

It is certified that error appears in the above-identified patent and that said Letters Patent is hereby corrected as shown below:

Column 66,
Line 15, add -- and -- after the semi-colon to read "fluid; and".
Line 19, delete the ";" after "expression" and add -- wherein the sample collection device is --.
Line 24, after "wherein the", delete "hand-held breast pump comprises a".
Line 26, after "within" delete "a".

Column 67,
Line 20, add -- primary -- before "solid".
Line 28, delete "sample" after "primary".
Line 42, delete "member" after "reservoir".

Column 68,
Line 65, delete "member" after "reservoir".

Column 69,
Line 2, delete "means comprises a vacuum pump" after "vacuum pump".
Line 3, delete "connected to a vacuum pump housing of the vacuum pump means, wherein the vacuum pump" after "mechanism".

Signed and Sealed this

Twenty-fourth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,887,210 B2
DATED : May 3, 2005
INVENTOR(S) : Steven C. Quay

It is certified that error appears in the above-identified patent and that said Letters Patent is hereby corrected as shown below:

Column 66,
Line 15, add -- and -- after the semi-colon to read "fluid; and".
Line 19, delete the ";" after "expression" and add -- wherein the sample collection device is --.
Line 24, after "wherein the", delete "hand-held breast pump comprises a".
Line 26, after "within" delete "a".

Column 67,
Line 20, add -- primary -- before "solid".
Line 28, delete "sample" after "primary".
Line 42, delete "member" after "reservoir".

Column 68,
Line 65, delete "member" after "reservoir".

Column 69,
Line 2, delete "means comprises a vacuum pump" after "vacuum pump".
Line 3, delete "connected to a vacuum pump housing of the vacuum pump means, wherein the vacuum pump" after "mechanism".

This certificate supersedes Certificate of Correction issued January 24, 2006.

Signed and Sealed this

Seventh Day of March, 2006

JON W. DUDAS
*Director of the United States Patent and Trademark Office*